United States Patent
Kurtis et al.

(10) Patent No.: US 11,692,026 B2
(45) Date of Patent: Jul. 4, 2023

(54) ANTIBODIES TO PFGARP KILL PLASMODIUM FALCIPARUM MALARIA PARASITES AND PROTECT AGAINST INFECTION AND SEVERE DISEASE

(71) Applicant: Rhode Island Hospital, Providence, RI (US)

(72) Inventors: Jonathan Kurtis, Providence, RI (US); Dipak K. Raj, Providence, RI (US); Alok Das Mohapatra, Providence, RI (US); Jenna Zuromski, Providence, RI (US)

(73) Assignee: RHODE ISLAND HOSPITAL, Providence, RI (US)

( * ) Notice: Subject to any disclaimer, the term of this patent is extended or adjusted under 35 U.S.C. 154(b) by 121 days.

(21) Appl. No.: 17/146,423

(22) Filed: Jan. 11, 2021

(65) Prior Publication Data
US 2021/0230258 A1    Jul. 29, 2021

Related U.S. Application Data

(60) Provisional application No. 62/959,851, filed on Jan. 10, 2020.

(51) Int. Cl.
| *A61K 39/395* | (2006.01) |
| *C07K 16/20* | (2006.01) |
| *A61K 45/06* | (2006.01) |
| *A61P 33/06* | (2006.01) |
| *A61K 39/00* | (2006.01) |

(52) U.S. Cl.
CPC ............ *C07K 16/205* (2013.01); *A61K 45/06* (2013.01); *A61P 33/06* (2018.01); *A61K 2039/505* (2013.01)

(58) Field of Classification Search
CPC .................................................... C07K 16/205
See application file for complete search history.

(56) References Cited

U.S. PATENT DOCUMENTS

| 2010/0260748 | A1 | 10/2010 | Elkins et al. | |
| 2017/0209571 | A1* | 7/2017 | Kanapuram | ........... A61K 47/10 |
| 2017/0326219 | A1 | 11/2017 | Kurtis et al. | |

FOREIGN PATENT DOCUMENTS

| WO | 2011123489 A2 | 10/2011 |
| WO | 2013126746 A2 | 8/2013 |
| WO | 2018165720 A1 | 9/2018 |
| WO | 2019236875 A1 | 12/2019 |

OTHER PUBLICATIONS

Paul (Fundamental Immunology, 3rd Edition, pp. 292-295) (Year: 1993).*
Bendig et al (Methods: A companion Methods in Enzymology vol. 8, pp. 83-93) (Year: 1995).*
MacCallum et al (J. Mol. Biol. vol. 262, pp. 732-745) (Year: 1996).*
Casset et al (Biochemical and Biophysical Research Communications vol. 307, pp. 198-205) (Year: 2003).*
Wu et al (Journal of Molecular Biology vol. 294, pp. 151-162) (Year: 1999).*
Skolnick et al (Trends in Biotechnology vol. 18, pp. 34-39) (Year: 2000).*
Vajdos et al (Journal of Molecular Biology vol. 320, pp. 415-428) (Year: 2002).*
"International Search Report and Written Opinion received for PCT Patent Application No. PCT/US2021/012961, dated Jun. 11, 2021", 14 pages.
Absalon , et al., "An Essential Malaria Protein Defines the Architecture of Blood-Stage and Transmission-Stage Parasites", Nature Communications, vol. 7, 2016, pp. 1-11.
Agnandji , et al., "First Results of Phase 3 Trial of RTS,S/AS01 Malaria Vaccine in African Children", The New England Journal of Medicine, vol. 365, No. 20, Nov. 17, 2011, pp. 1863-1875.
Almukadi , et al., "Human Erythrocyte Band 3 is a Host Receptor for Plasmodium falciparum Glutamic Acid-Rich Protein", Blood, vol. 133, No. 5, Jan. 2019, pp. 470-480.
Boddey , et al., "Export of Malaria Proteins requires Co-Translational Processing of the PEXEL Motif Independent of Phosphatidylinositol-3-Phosphate Binding", Nature Communications, vol. 7, 2016, pp. 1-14.
Ch'ng , et al., "A Programmed Cell Death Pathway in the Malaria Parasite Plasmodium falciparum has General Features of Mammalian Apoptosis but is Mediated by Clan CA Cysteine Proteases", Cell Death and Disease, vol. 1, 2010, pp. 1-13.
Daily , et al., "In Vivo Transcriptome of Plasmodium falciparum Reveals Overexpression of Transcripts that Encode Surface Proteins", The Journal of Infectious Diseases, vol. 191, Apr. 1, 2005, pp. 1196-1203.
Davies , et al., "Expansion of Lysine-Rich Repeats in Plasmodium Proteins Generates Novel Localization Sequences that Target the Periphery of the Host Erythrocyte", The Journal of Biological Chemistry, vol. 291, No. 50, Dec. 9, 2016, pp. 26188-26207.
Engelbrecht , et al., "Turning up the Heat: Heat Stress Induces Markers of Programmed Cell Death in Plasmodium falciparum in Vitro", Cell Death and Disease, vol. 4, 2013, pp. 1-11.
Ghorbal , et al., "Genome Editing in the Human Malaria Parasite Plasmodium falciparum using the CRISPR-Cas9 System", Nature Biotechnology, vol. 32, 2014, pp. 1-5.
Gunjan , et al., "Mefloquine Induces ROS Mediated Programmed Cell Death in Malaria Parasite: Plasmodium", Apoptosis, vol. 21, 2016, 10 pages.
Korde , et al., "A Prodomain Peptide of Plasmodium falciparum Cysteine Protease (Falcipain-2) Inhibits Malaria Parasite Development", Journal of Medicinal Chemistry, vol. 51, No. 11, 2008, pp. 3116-3123.

(Continued)

*Primary Examiner* — Albert M Navarro
*Assistant Examiner* — Mark Navarro
(74) *Attorney, Agent, or Firm* — Adler Pollock & Sheehan P.C.

(57) ABSTRACT

Provided herein are methods, compositions and kits for preventing and treating malaria. Also included herein are kits for preventing and treating malaria.

12 Claims, 47 Drawing Sheets
(40 of 47 Drawing Sheet(s) Filed in Color)
Specification includes a Sequence Listing.

(56) References Cited

OTHER PUBLICATIONS

Lang, et al., "Triggers, Inhibitors, Mechanisms, and Significance of Eryptosis: The Suicidal Erythrocyte Death", BioMed Research International, vol. 2015, 2015, pp. 1-16.

Matthews, et al., "Variation in Apoptosis Mechanisms Employed by Malaria Parasites: The Roles of Inducers, Dose Dependence and Parasite Stages", Malaria Journal, vol. 11, No. 297, 2012, pp. 1-12.

Murray, et al., "Global Malaria Mortality between 1980 and 2010: A Systematic Analysis", Lancet, vol. 379, Feb. 4, 2012, pp. 413-431.

O'Donnell, et al., "A Genetic Screen for Improved Plasmid Segregation Reveals a Role for Rep20 in the Interaction of Plasmodium falciparum Chromosomes", The EMBO Journal, vol. 21, No. 5, 2002, pp. 1231-1239.

Okie, Susan, "Betting on a Malaria Vaccine", The New England Journal of Medicine, vol. 353, No. 18, Nov. 3, 2005, pp. 1877-1881.

Raj, et al., "Antibodies to Plasmodium Falciparum Glutamic Acid Rich Protein (PfGARP) Inhibit Parasite Growth by Arresting Trophozoite Development", International Journal of Infectious Diseases, vol. 45, Apr. 1, 2016, pp. 3776.

Raj, et al., "Anti-PfGARP Activates Programmed Cell Death of Parasites and Reduces Severe Malaria", Nature, vol. 582, Jun. 4, 2020, 28 pages.

Ralph, et al., "Transcriptome Analysis of Antigenic Variation in Plasmodium falciparum—Var Silencing is not Dependent on Antisense RNA", Biology, vol. 6, No. 11, 2005, pp R93.1-R93.12.

Rathore, et al., "Disruption of a Mitochondrial Protease Machinery in Plasmodium falciparum is an Intrinsic Signal for Parasite Cell Death", Cell Death and Disease, vol. 2, 2011, pp. 1-12.

Rathore, et al., "Disruption of Cellular Homeostasis Induces Organelle Stress and Triggers Apoptosis like Cell-Death Pathways in Malaria Parasite", Cell Death and Disease, vol. 6, 2015, pp. 1-13.

Triglia, et al., "Structure of a Plasmodium falciparum Gene that Encodes a Glutamic Acid-Rich Protein (GARP)", Molecular and Biochemical Parasitology, vol. 31, No. 2, 1988, pp. 199-201.

Vignali, et al., "NSR-Seq Transcriptional Profiling Enables Identification of a Gene Signature of Plasmodium falciparum Parasites Infecting Children", The Journal of Clinical Investigation, vol. 121, No. 3, Mar. 2011, pp. 1119-1129.

Viswanathan, et al., "High-Performance Probes for Light and Electron Microscopy", Nature Methods, vol. 12, 2015, pp. 1-13.

Zhang, et al., "Uncovering the Essential Genome of the Human Malaria Parasite Plasmodium falciparum by Saturation Mutagenesis", Science, vol. 360, No. 6388, May 2018, pp. 1-26.

* cited by examiner

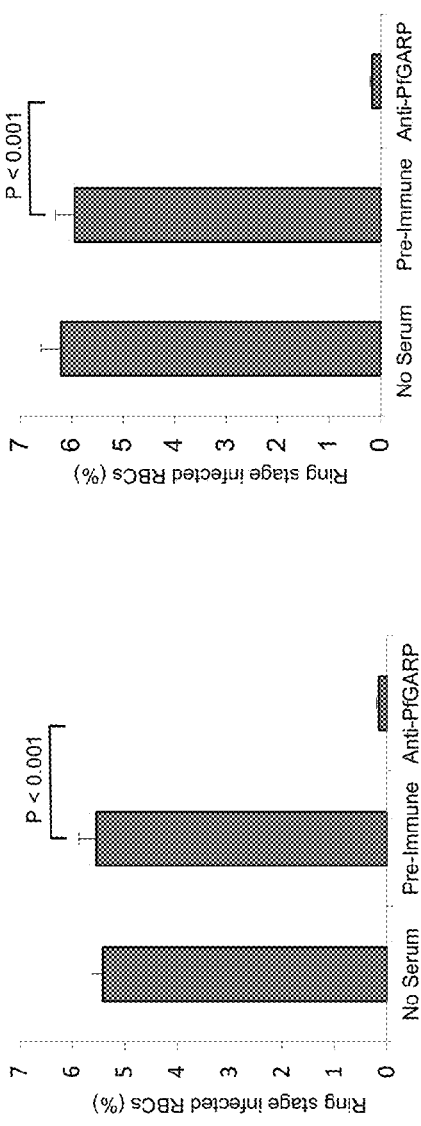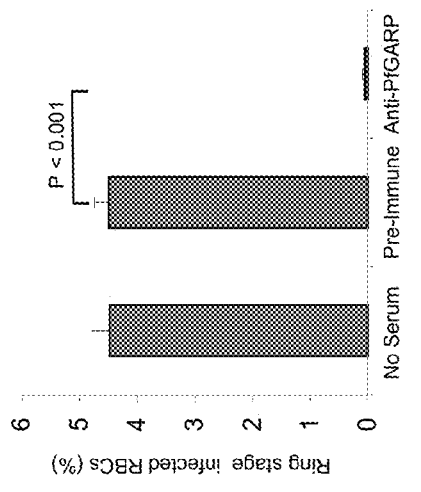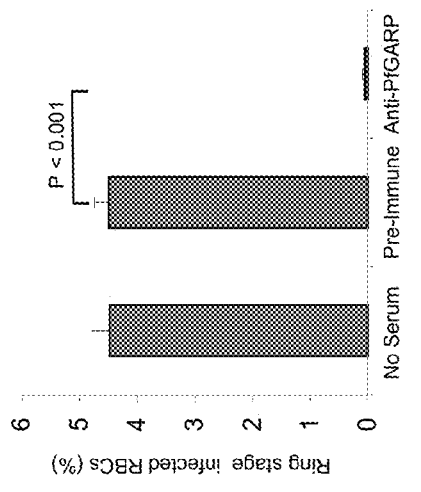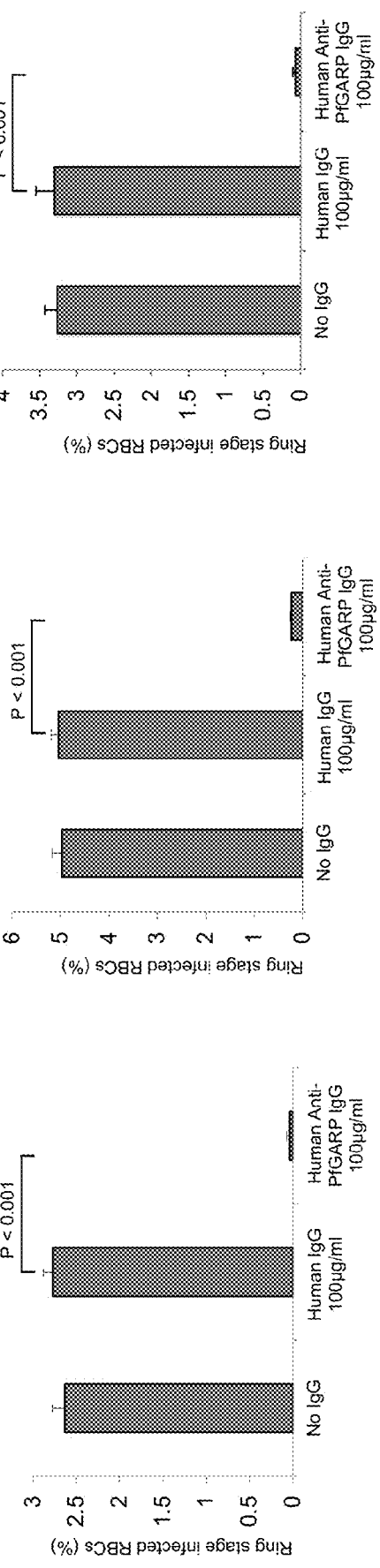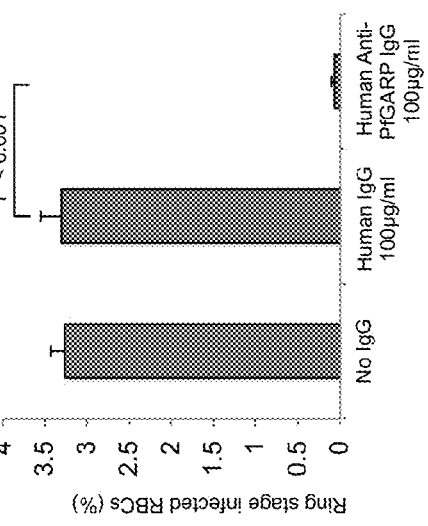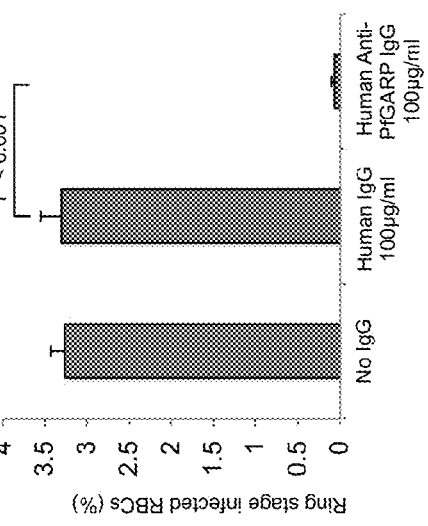

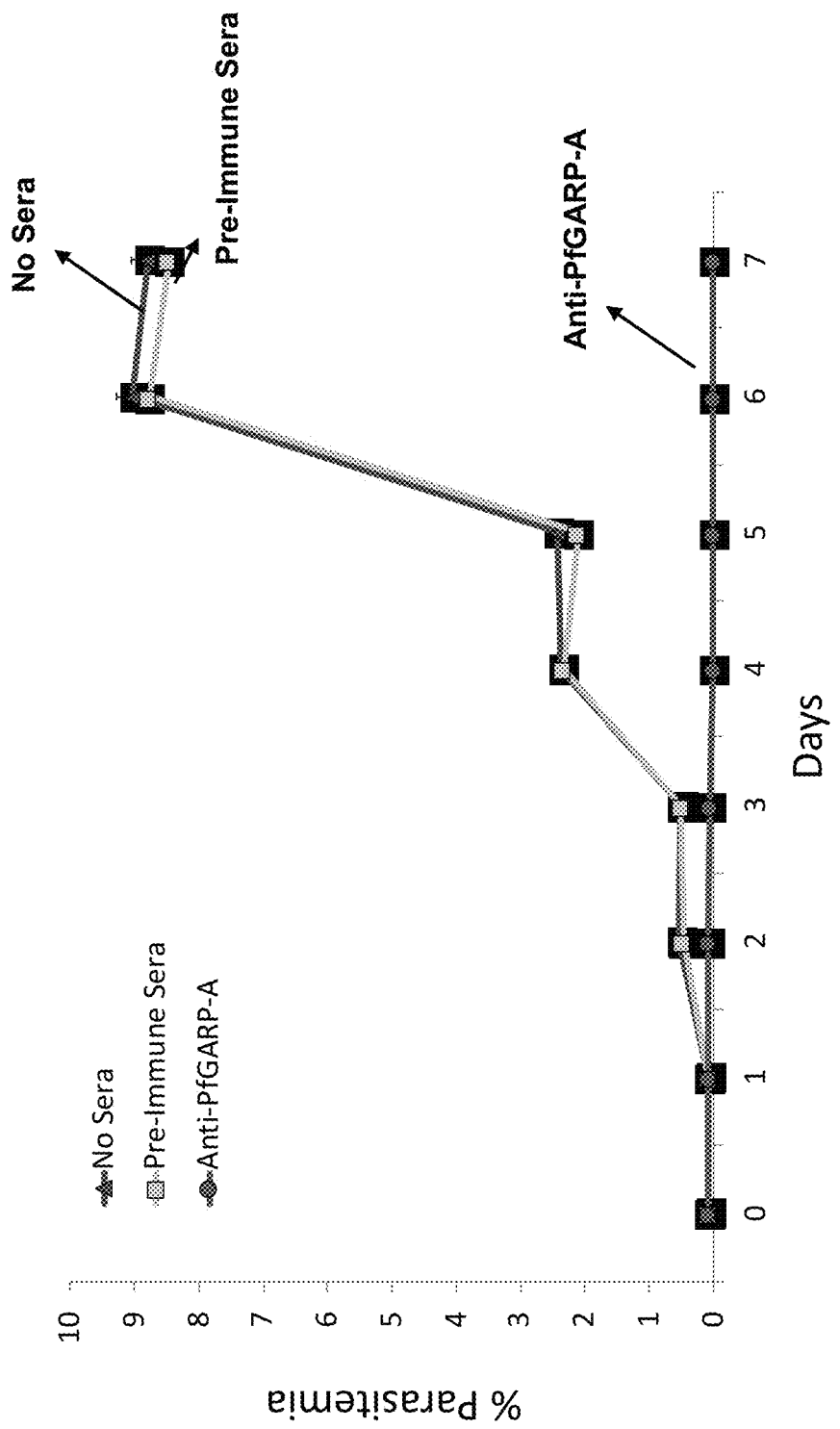

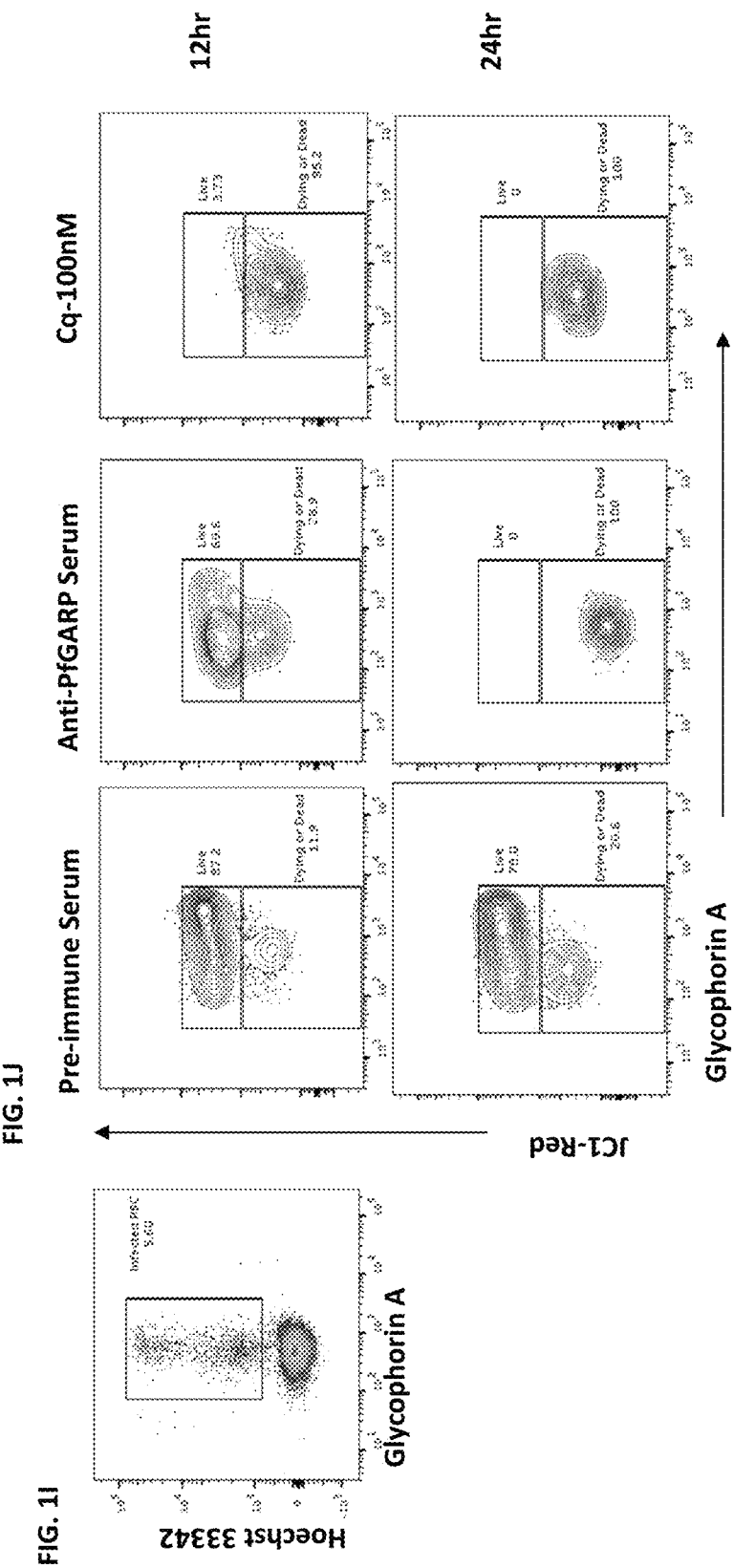

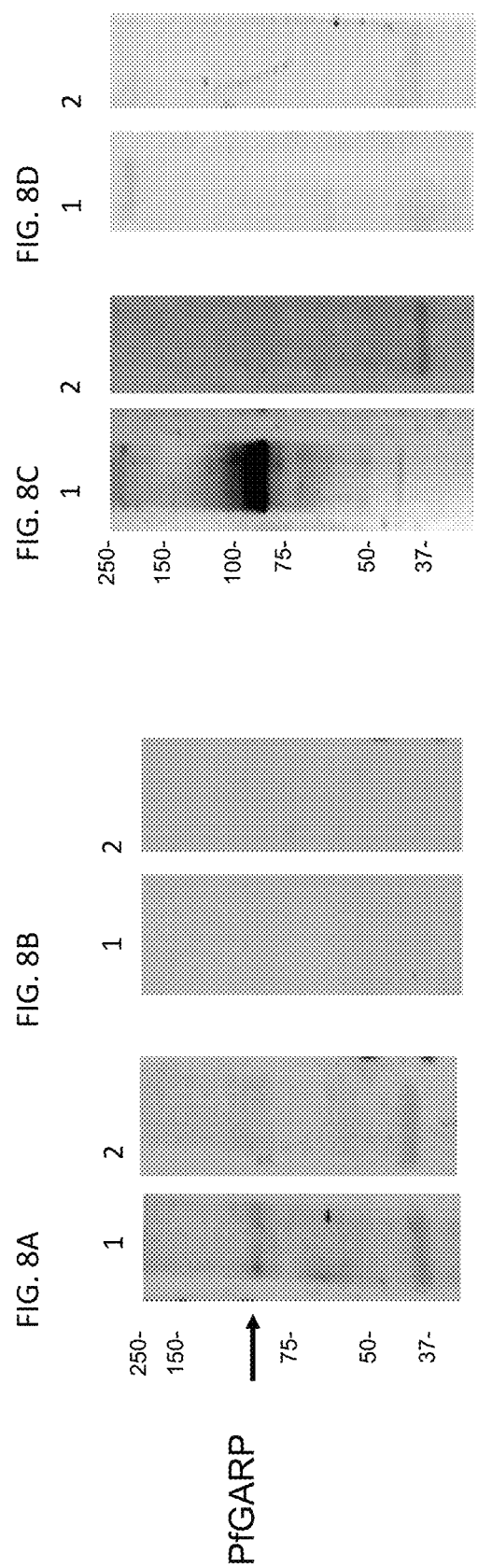

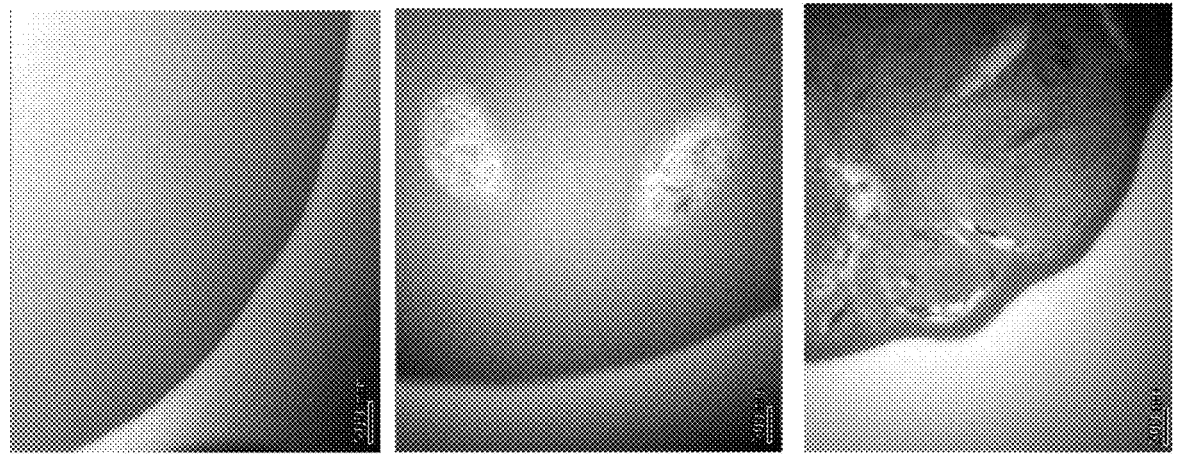
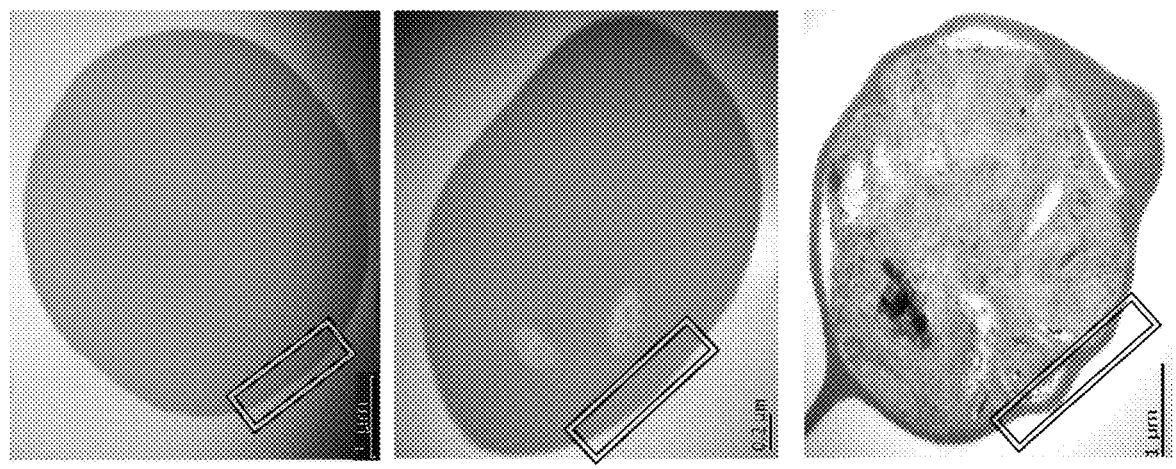
FIG. 11A  FIG. 11B  FIG. 11C

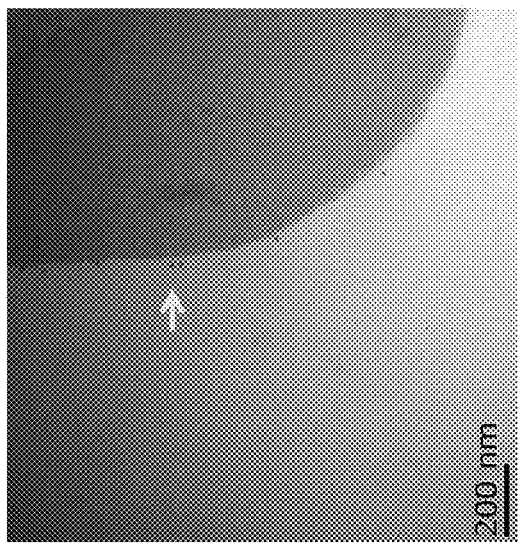
D'
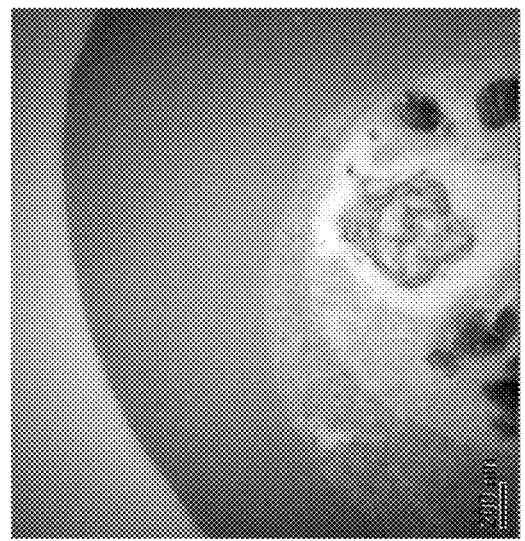
E'
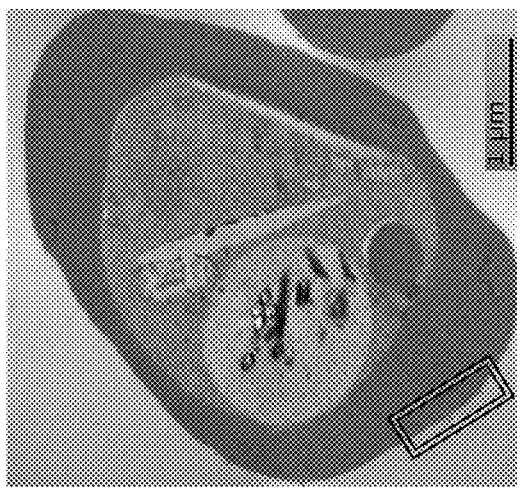
FIG. 11D
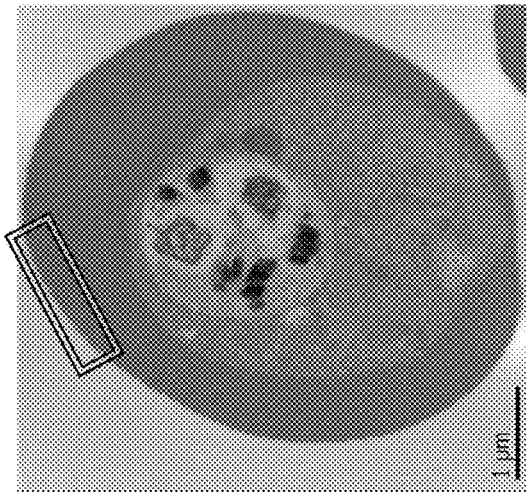
FIG. 11E

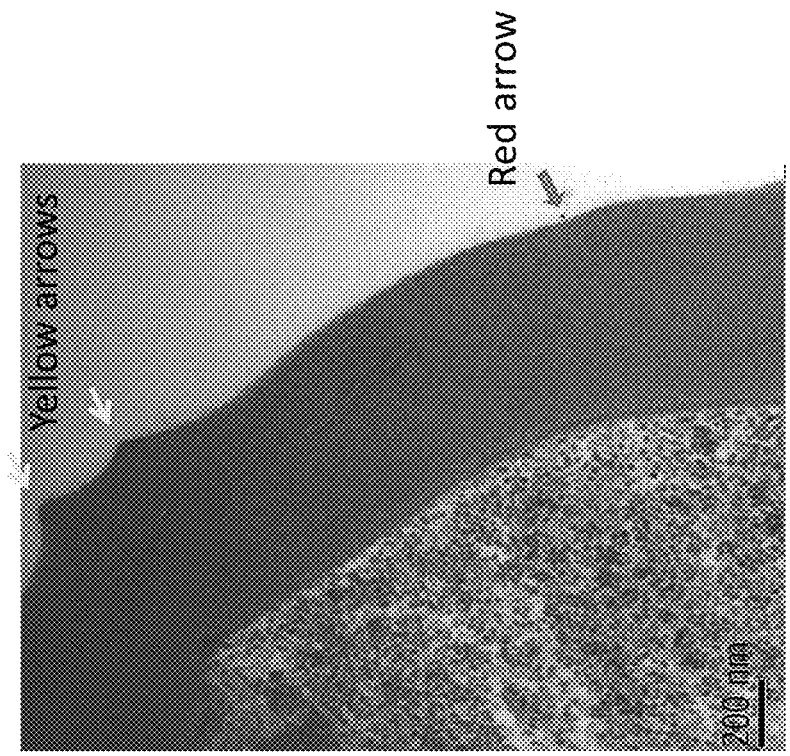
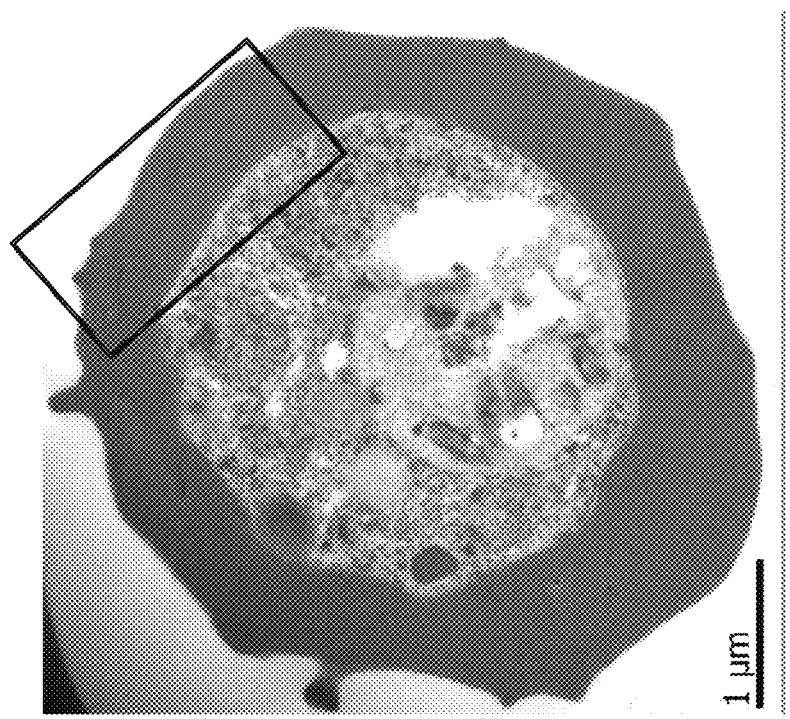
FIG. 14

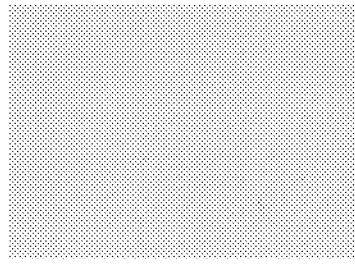
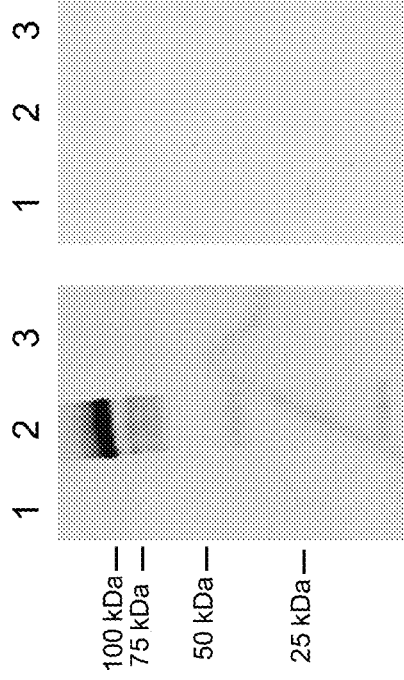
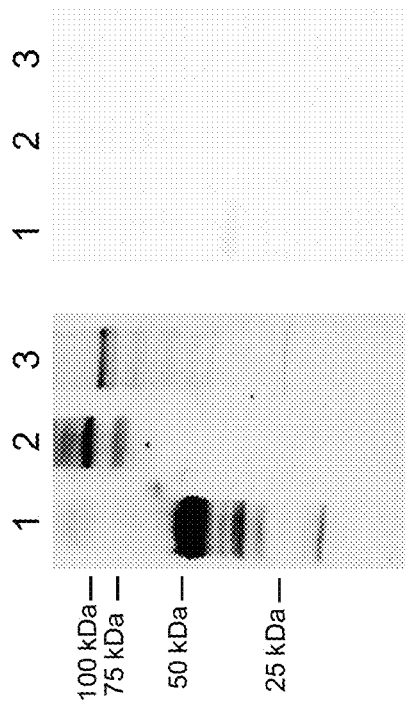
FIG. 18A
FIG. 18B    FIG. 18C
FIG. 18D    FIG. 18E

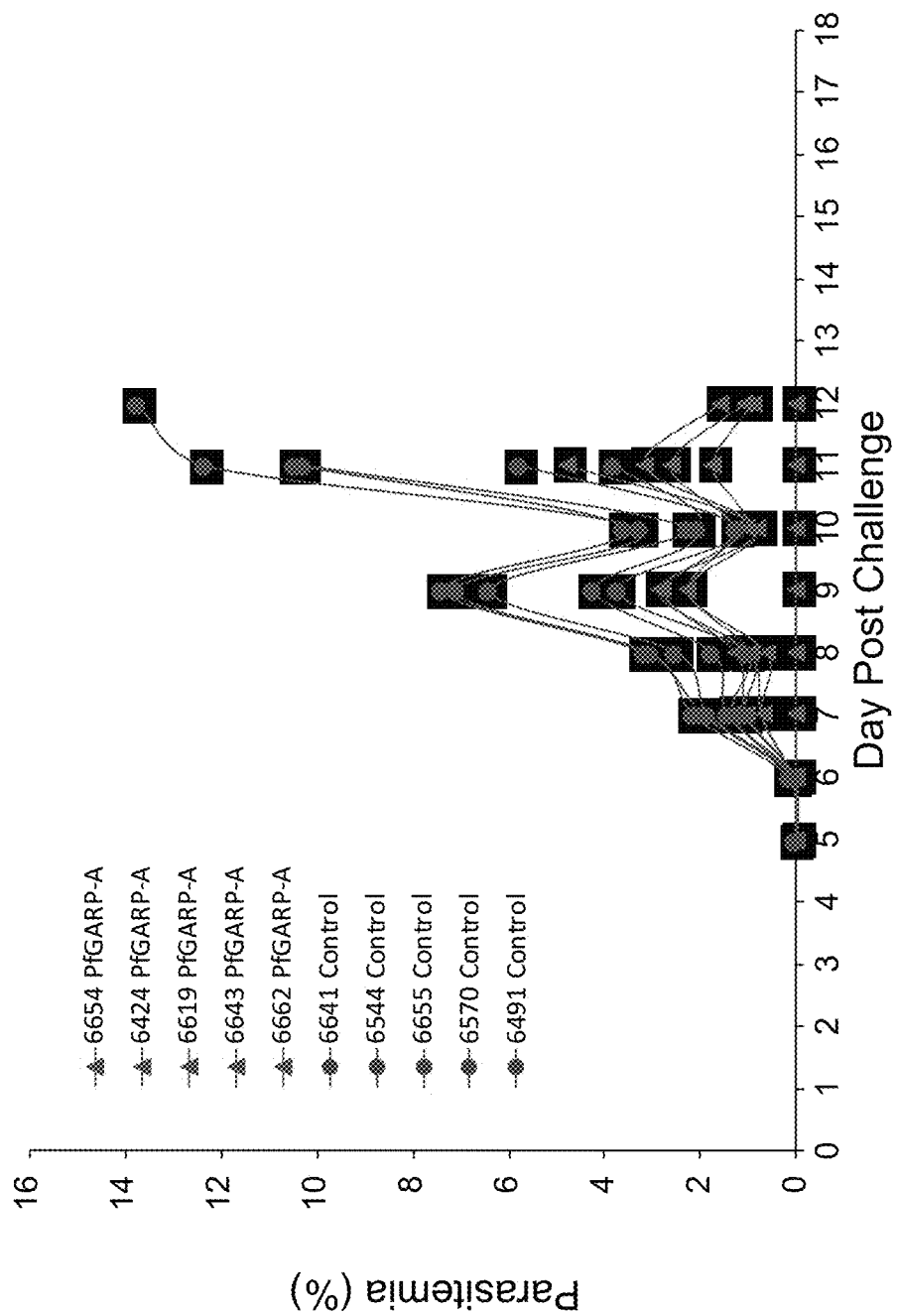

V heavy

EAQLQQSGTELVKPGASVKLSCTASGF
YIKDTYIHWVRQRPVQGLEWIGRIDP
ANYDTKYDPKFQGKATITADTSSNTAY
LQLINLTPEDTVVYCTSFGGTKLRFAY
WGQGTLVTVSA

V light

NIMMTQSPSSLAVSAGEEVTMSCK
SSQSVLYSSNQRNYLAWFQQKSGQ
SPKLLIYWASTRESGVPDRFTGSGSG
TDFTLTISNLQVEDLAVYYCLQHFSS
WTFGGGTKLEIK

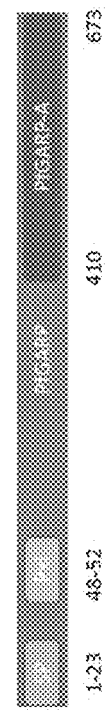
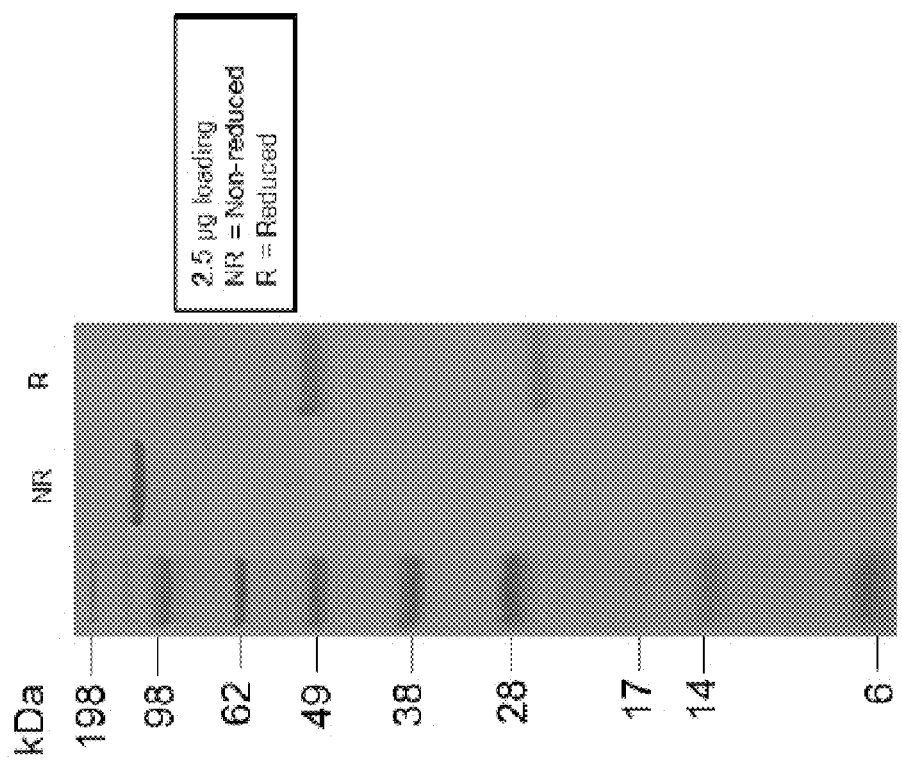
FIG. 24C
FIG. 24D

Goat anti-mouse IgG (H+L) DyLight680 (0.2 μg/ml)

Adjusted scan

GARP mouse mAb, 1 µg/ml

Control staining

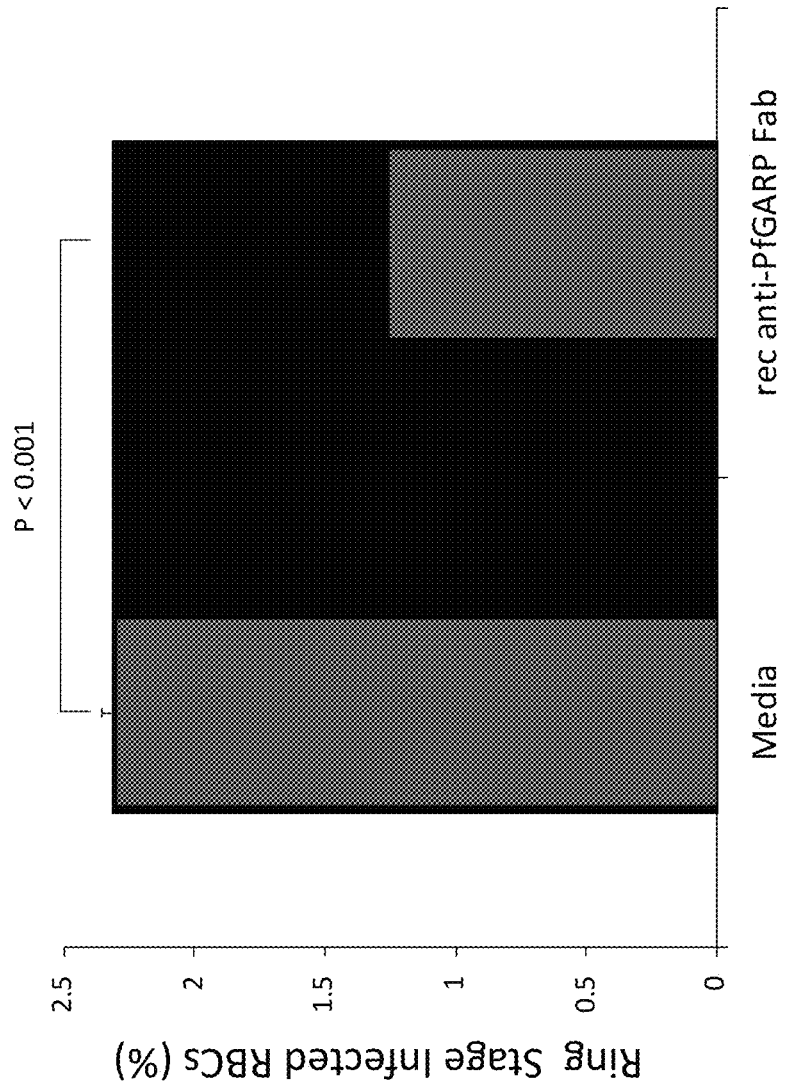
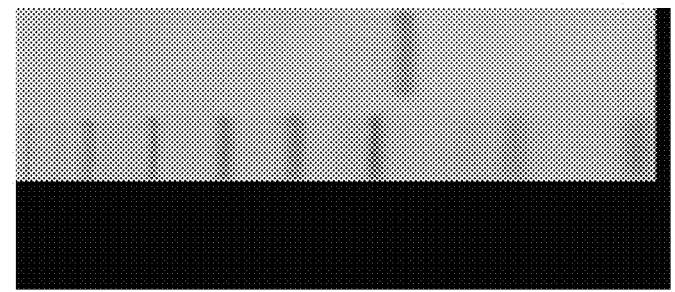

SEQUENCE LISTING

<160> NUMBER OF SEQ ID NOS: 13

<210> SEQ ID NO 1
<211> LENGTH: 8
<212> TYPE: PRT

<213> ORGANISM: Artificial Sequence
<220> FEATURE:
<223> OTHER INFORMATION: PfGARP epitope

<400> SEQUENCE: 1

Glu Asp Lys Asp Gly Val Glu Ile
1               5

<210> SEQ ID NO 2
<211> LENGTH: 17
<212> TYPE: PRT
<213> ORGANISM: Artificial Sequence
<220> FEATURE:
<223> OTHER INFORMATION: CDR2 Peptide

<400> SEQUENCE: 2

Arg Ile Asp Pro Ala Asn Tyr Asp Thr Lys Tyr Asp Pro Lys Phe Gln
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: CDR3 peptide

<400> SEQUENCE: 3

Phe Gly Gly Thr Lys Leu Arg Phe Ala Tyr
1               5                   10

<210> SEQ ID NO 4
<211> LENGTH: 17
<212> TYPE: PRT
<213> ORGANISM: Artificial Sequence
<220> FEATURE:
<223> OTHER INFORMATION: CDR1 peptide

<400> SEQUENCE: 4

Lys Ser Ser Gln Ser Val Leu Tyr Ser Asn Gln Arg Asn Tyr Leu
1               5                   10                  15

Ala

<210> SEQ ID NO 5
<211> LENGTH: 7
<212> TYPE: PRT
<213> ORGANISM: Artificial Sequence
<220> FEATURE:
<223> OTHER INFORMATION: CDR2 Peptide

<400> SEQUENCE: 5

Trp Ala Ser Thr Arg Glu Ser
1               5

<210> SEQ ID NO 6
<211> LENGTH: 8
<212> TYPE: PRT
<213> ORGANISM: Artificial Sequence
<220> FEATURE:
<223> OTHER INFORMATION: CDR3 Peptide

<400> SEQUENCE: 6

Leu Gln His Phe Ser Ser Trp Thr
1               5

```
<210> SEQ ID NO 7
<211> LENGTH: 119
<212> TYPE: PRT
<213> ORGANISM: Artificial Sequence
<220> FEATURE:
<223> OTHER INFORMATION: heavy chain variable region

<400> SEQUENCE: 7

Glu Ala Gln Leu Gln Gln Ser Gly Thr Glu Leu Val Lys Pro Gly Ala
1               5                   10                  15

Ser Val Lys Leu Ser Cys Thr Ala Ser Gly Phe Tyr Ile Lys Asp Thr
            20                  25                  30

Tyr Ile His Trp Val Arg Gln Arg Pro Val Gln Gly Leu Glu Trp Ile
        35                  40                  45

Gly Arg Ile Asp Pro Ala Asn Tyr Asp Thr Lys Tyr Asp Pro Lys Phe
    50                  55                  60

Gln Gly Lys Ala Thr Ile Thr Ala Asp Thr Ser Asn Thr Ala Tyr
65                  70                  75                  80

Leu Gln Leu Ile Asn Leu Thr Pro Glu Asp Thr Val Val Tyr Tyr Cys
                85                  90                  95

Thr Ser Phe Gly Gly Thr Lys Leu Arg Phe Ala Tyr Trp Gly Gln Gly
            100                 105                 110

Thr Leu Val Thr Val Ser Ala
        115

<210> SEQ ID NO 8
<211> LENGTH: 112
<212> TYPE: PRT
<213> ORGANISM: Artificial Sequence
<220> FEATURE:
<223> OTHER INFORMATION: light chain variable region

<400> SEQUENCE: 8

Asn Ile Met Met Thr Gln Ser Pro Ser Ser Leu Ala Val Ser Ala Gly
1               5                   10                  15

Glu Glu Val Thr Met Ser Cys Lys Ser Ser Gln Ser Val Leu Tyr Ser
            20                  25                  30

Ser Asn Gln Arg Asn Tyr Leu Ala Trp Phe Gln Lys Ser Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Asn Leu Gln Val Glu Asp Leu Ala Val Tyr Tyr Cys Leu Gln
                85                  90                  95

His Phe Ser Ser Trp Thr Phe Gly Gly Gly Thr Lys Leu Glu Ile Lys
            100                 105                 110

<210> SEQ ID NO 9
<211> LENGTH: 17
<212> TYPE: PRT
<213> ORGANISM: Artificial Sequence
<220> FEATURE:
<223> OTHER INFORMATION: Residues 443-459 peptide

<400> SEQUENCE: 9

Val Lys Asn Val Ile Glu Asp Glu Asp Lys Asp Gly Val Glu Ile Ile
1               5                   10                  15

Asn
```

```
<210> SEQ ID NO 10
<211> LENGTH: 20
<212> TYPE: DNA
<213> ORGANISM: Artificial Sequence
<220> FEATURE:
<223> OTHER INFORMATION: PCR primer

<400> SEQUENCE: 10
ggagctgtcg tattccagtc                                              20

<210> SEQ ID NO 11
<211> LENGTH: 20
<212> TYPE: DNA
<213> ORGANISM: Artificial Sequence
<220> FEATURE:
<223> OTHER INFORMATION: PCR Primer

<400> SEQUENCE: 11
aacccctcaa gacccgttta                                              20

<210> SEQ ID NO 12
<211> LENGTH: 15
<212> TYPE: PRT
<213> ORGANISM: Artificial Sequence
<220> FEATURE:
<223> OTHER INFORMATION: GARP epitope

<400> SEQUENCE: 12

Asn Val Ile Glu Asp Glu Asp Lys Asp Gly Val Glu Ile Ile Asn
1               5                   10                  15

<210> SEQ ID NO 13
<211> LENGTH: 5
<212> TYPE: PRT
<213> ORGANISM: Artificial Sequence
<220> FEATURE:
<223> OTHER INFORMATION: CDR1 peptide

<400> SEQUENCE: 13

Asp Thr Tyr Ile His
1               5
```

ANTIBODIES TO PFGARP KILL *PLASMODIUM FALCIPARUM* MALARIA PARASITES AND PROTECT AGAINST INFECTION AND SEVERE DISEASE

RELATED APPLICATIONS

This application claims priority to U.S. Provisional Application No. 62/959,851, filed on Jan. 10, 2020, the entire contents of which are incorporated herein by reference in its entirety.

STATEMENT AS TO FEDERALLY SPONSORED RESEARCH

This invention was made with government support under t R01AI076353, R01AI127699, R01AI52059, R01AI092120 and R01AI110699 awarded by the National Institutes of Health (NIH). The Government has certain rights in the invention.

INCORPORATED-BY-REFERENCE OF SEQUENCE LISTING

The contents of the text file named "021486-644001US_Sequence_Listing.txt", which was created on Feb. 2, 2021 and is 8,192 bytes in size, are hereby incorporated by reference in their entirety.

FIELD OF THE INVENTION

The invention relates to compositions and methods for preventing and treating malaria

BACKGROUND

*Plasmodium falciparum* malaria is a leading cause of morbidity and mortality in developing countries, infecting hundreds of millions of individuals and killing up to one half a million children in sub-Saharan Africa each year (Murray, C. J. et al. *Lancet* 379, 413-431(2012) and WHO. The World Malaria Report. Vol. http://www.who.int/malaria/publications/world-malaria-report-2017/report/en/(WHO, 2017)). Children bear the greatest burden from malaria, yet vaccine discovery efforts have not targeted this age group. Of the dozens of subunit vaccine candidates currently under preclinical and clinical investigation, the majority are based on only four parasite antigens (Okie, S. *N Engl J Med* 353, 1877-1881 (2005) and WHO. Malaria Vaccine Rainbow Tables. http://www.who.int/vaccine_research/links/Rainbow/en/index.html (2012)). Antigen candidates are urgently needed, but strategies to identify them remain limited.

SUMMARY OF THE INVENTION

The invention provides a solution to a longstanding problem in the field of malaria vaccines and treatments for malarial disease. Provided herein are methods, compositions and kits for treating and preventing infection with the malaria pathogen and malarial disease. Also included herein are kits for treating malarial infection and disease. The invention features an anti-*Plasmodium falciparum* (*P. falciparum*) PfGARP antibody with a binding specificity to an operative epitope of PfGARP comprising or consisting of the amino acid sequence, EDKDGVEI (SEQ ID NO: 1).

For example, provided herein is an anti-*Plasmodium falciparum* (*P. falciparum*) PfGARP antibody comprising a heavy chain variable region comprising the one or more of the amino acid sequences set forth in SEQ ID NO: 1 (complementary determining region (CDR)1; DTYIH (SEQ ID NO: 13)), SEQ ID NO: 2 (CDR2; RIDPANYDT-KYDPKFQG (SEQ ID NO: 2)), and SEQ ID NO: 3 (CDR3; FGGTKLRFAY (SEQ ID NO: 3)); and a light chain variable region comprising the amino acid sequences set forth in SEQ ID NO: 4 (CDR1; KSSQSVLYSSNQRNYLA (SEQ ID NO: 4)), SEQ ID NO: 5 (CDR2; WASTRES (SEQ ID NO: 5)), and SEQ ID NO: 6 (CDR3; LQHFSSWT (SEQ ID NO: 6)). In other embodiments, an anti-*Plasmodium falciparum*: (*P. falciparum*) PfGARP antibody comprises one or more of the amino acid sequences set forth in SEQ ID NO: 1 (complementary determining region (CDR)1; DTYIH (SEQ ID NO: 13)), SEQ ID NO: 2 (CDR2; RIDPANYDT-KYDPKFQG (SEQ ID NO: 2)), and SEQ ID NO: 3 (CDR3; FGGTKLRFAY (SEQ ID NO: 3)); and a light chain variable region comprising the amino acid sequences set forth in SEQ ID NO: 4 (CDR1; KSSQSVLYSSNQRNYLA (SEQ ID NO: 4)), SEQ ID NO: 5 (CDR2; WASTRES (SEQ ID NO: 5)), and SEQ ID NO: 6 (CDR3; LQHFSSWT (SEQ ID NO: 6)), each of the sequences that have at least 50% identity to the base reference and comprise a binding specificity to an operative epitope of PfGARP comprising or consisting of the amino acid sequence, EDKDGVEI (SEQ ID NO: 1). For example, the amino acid sequence a CDR described herein is at least 50%, at least 55%, at least 60%, at least 65%, at least 70%, at least 75%, at least 80%, at least 85%, at least 90%, at least 95%, at least 98%, at least 99%, or 100% identity to one or more of the CDR reference sequences described above (SEQ ID NO: 1, 2, 3, 4, 5, and/or 6).

The term "% identity," in the context of two or more nucleic acid or polypeptide sequences, refers to two or more sequences or subsequences that are the same or have a specified percentage of amino acid residues or nucleotides that are the same, when compared and aligned for maximum correspondence, as measured using one of the following sequence comparison algorithms or by visual inspection. For example, % identity is relative to the entire length of the coding regions of the sequences being compared, or the length of a particular fragment or functional domain thereof.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Percent identity is determined using search algorithms such as BEAST and PSI-BEAST (Altschul et al., 1990, J Mol Biol 215:3, 403-410; Altschul et al., 1997, Nucleic Acids Res 25:17, 3389-402). For the PSI-BLAST search, the following exemplary parameters are employed: (1) Expect threshold was 10; (2) Gap cost was Existence: 11 and Extension: 1; (3) The Matrix employed was BLOSUM62; (4) The filter for low complexity regions was "on".

As described herein, the anti-*P. falciparum* PfGARP antibody comprises a heavy chain variable region comprising the amino acid sequence set forth in SEQ ID NO: 7 and a light chain variable region comprises the amino acid sequence set forth in SEQ ID NO: 8. In other examples, the heavy chain variable region of the anti-*P. falciparum* PfGARP antibody has the amino acid sequence of SEQ ID NO: 7 (EAQLQQSGTELVKPGASVKLSC- TASGFYIKDTYIHWVRQRPVQGLEWIGRIDPANY
DTKYDPKFQGKATITADTSSNTAYLQLINLTPEDTV-
VYYCTSFGGTKLRFAYWGQGT LVTVSA; SEQ ID NO:
7), and the amino acid sequence of said light chain variable region is SEQ ID NO: 8 (NIMMTQSPSSLAVSA-
GEEVTMSCKSSQSVLYSSNQR-
NYLAWFQQKSGQSPKLLIYW
ASTRESGVPDRFTGSGSGTDFTLTISNLQVEDLAVYY-
CLQHFSSWTFGGGTKLEIK; SEQ ID NO: 8).

In examples, the heavy chain variable region and the light chain variable region of the anti-*P. falciparum* PfGARP antibody of claim 1, wherein the heavy chain variable region and the light chain variable region are humanized. A humanized antibody is an antibody made by combining a human antibody with a small part of a mouse or rat monoclonal antibody (antigen binding portions, e.g., containing one or more CDRs of the mouse or rat monoclonal antibody). The mouse or rat part of the antibody binds to the target antigen, and the human part makes it less likely to be destroyed by the body's immune system. The CDR portions of the variable region are instrumental for the ability of the antibody to bind to its intended target antigen, e.g., PfGARP.

*Plasmodium falciparum* glutamic acid-rich protein (Pf-GARP)

Nucleic acid sequence; 792 bp (Sequence 1,231-2,022 of gene PFA_0620c)
TCAAAAGAACACAAATCAAAAGGAAAGAAAGATAAAGGAAAGAAAGATAAAG
GAAAACATAAAAAAGCAAAAAAAGAAAAAGTAAAAAAACACGTAGTTAAAAA
TGTTATAGAAGATGAAGACAAAGATGGTGTAGAAATAATAAACTTAGAAGATA
AAGAGGCATGTGAAGAACAACACATAACAGTAGAAAGTAGACCACTAAGCCAA
CCACAATGTAAACTAATAGATGAACCAGAACAATTAACATTAATGGATAAATCA
AAAGTTGAAGAAAAAAACTTATCCATACAAGAGCAATTAATAGGTACCATAGG
ACGTGTTAATGTAGTACCCAGAAGAGATAATCATAAGAAAAAAATGGCGAAGA
TAGAGGAAGCTGAACTTCAAAAACAGAAACATGTTGATAAGGAAGAAGACAAA
AAAGAAGAATCCAAAGAAGTAGAAGAAGAATCTAAAGAGGTACAAGAAGATG
AAGAAGAAGTAGAAGAAGATGAAGAAGAAGAAGAAGAAGAGGAAGAAGA
AGAAGAAGAAGAAGAAGAAGAGGAAGAAGAAGAAGATGAAGTAGAAGAAGAT
GAAGATGATGCTGAAGAAGATGAAGATGATGCTGAAGAAGATGAAGATGATGC
TGAAGAAGATGATGATGATGCTGAAGAAGATGATGATGATGCTGAAGAAGATG
ATGATGAAGATGAAGATGAAGATGAAGAAGAAGAAGATGAAGAAGAAGA
AGAAGAATCAGAAAAAAAAATAAAAAGAAATTTGAGAAAAAATGCCAAAATTT
AA Sequence Length: 792 (SEQ ID NO: 9)

Amino acid sequence of residues 410-673 of full length Pf-GARP (see below)
SKEHKSKGKKDKGKKDKGKHKKAKKEKVKKHVVKNVIEDEDKDGVEIINLEDKEA
CEEQHITVESRPLSQPQCKLIDEPEQLTLMDKSKVEEKNLSIQEQLIGTIGRVNVVPRR
DNHKKKMAKIEEAELQKQKHVDKEEDKKEESKEVEEESKEVQEDEEEVEEDEEEEE
EEEEEEEEEEEEEEEEDEVEEDEDDAEEDEDDAEEDEDDAEEDDDDAEEDDDDAE
EDDDEDEDEDEEEEEDEEEEEESEKKIKRNLRKNAKI Sequence Length: 263 (SEQ ID NO: 10)

Amino acid sequence of Pf-GARP (Full length protein)
MNVLFLSYNICILFFVVCTLNFSTKCFSNGLLKNQNILNKSFDSITGRLLNETELEKNK
DDNSKSETLLKEEKDEKDDVPTTSNDNLKNAHNNNEISSSTDPTNIINVNDKDNENS
VDKKKDKKEKKHKKDKKEKKEKKDKKEKKDKKEKKHKKEKKHKKDKKKEENSE
VMSLYKTGQHKPKNATEHGEENLYEEMVSEINNNAQGGLLLSSPYQYREQGGCGII
SSVHETSNDTKDNDKENISEDKKEDHQQEEMLKTLDKKERKQKEKEMKEQEKIEK
KKKKQEEKEKKKQEKERKKQEKKERKQKEKEMKKQKKIEKERKKKEEKEKKKKK
HDKENEETMQQPDQTSEETNNEIMVPLPSPLTDVTTPEEHKEGEHKEEEHKEGEHKE
GEHKEEEHKEEEHKKEEHK*SKEHKSKGKKDKGKKDKGKHKKAKKEKVKKHVVKNV*
*IEDEDKDGVEIINLEDKEACEEQHITVESRPLSQPQCKLIDEPEQLTLMDKSKVEEK*
*NLSIQEQLIGTIGRVNVVPRRDNHKKKMAKIEEAELQKQKHVDKEEDKKEESKEVE*
*EESKEVQEDEEEVEEDEEEEEEEEEEEEEEEEEEEEEDEVEEDEDDAEEDEDDA*
*EEDEDDAEEDDDDAEEDDDDAEEDDIEDEDEDEEEEEDEEEEEESEKKIKRNLRK*
*NAKI* Sequence Length: 673 aa (SEQ ID NO: 11)

Coding Nucleic acid sequence gene Pf-GARP (PFA_0620c)
ATGAATGTGCTATTTCTTTCGTATAATATTTGTATTCTTTTTTTTGTTGTATGCACA
TTAAATTTTTCTACTAAGTGCTTTTCCAATGGTTTATTGAAGAATCAAAATATCCT
AAACAAAAGTTTTGATTCCATAACGGGAAGATTATTAAACGAAACCGAATTAGA
AAAAAATAAAGATGATAATTCAAAATCTGAAACGTTGTTAAAAGAGGAAAAAG
ATGAAAAGGATGATGTACCTACAACGAGTAATGACAACCTTAAGAATGCTCATA
ATAATAATGAAATTTCAAGTTCAACTGATCCAACGAATATTATTAATGTTAATGA
TAAAGATAATGAAAACTCTGTAGATAAAAAAAAAGATAAAAAAGAAAAAAAGC
ATAAAAAAGATAAAAAAGAAAAAAAAGAAAAAAAAGATAAAAAAGAAAAAAA
AGATAAAAAAGAAAAAAAACATAAAAAAGAAAAAAAACATAAAAAAGATAAA
AAAAAAGAAGAAAACAGTGAAGTGATGTCTTTATATAAAACGGGTCAACATAA
ACCAAAAAACGCAACAGAACATGGTGAAGAAAATTTATATGAAGAAATGGTAA
GTGAAATAAATAATAATGCACAAGGTGGACTCCTTTTATCAAGCCCATATCAAT
ATAGAGAACAAGGAGGATGTGGAATCATATCTAGTGTTCATGAGACGTCTAATG
ATACAAAAGATAATGATAAAGAAAATATATCCGAAGACAAAAAGGAGGACCAT
CAACAAGAAGAAATGTTGAAAACACTTGATAAAAAAGAACGTAAACAAAAAGA
AAAAGAAATGAAAGAACAAGAAAAATCGAAAAAAAAAAAAAAAAAGCAAGAA
GAAAAGGAAAAGAAAAAACAAGAAAAAGAAAGAAAAAAACAAGAAAAGAAA
GAACGTAAACAAAAAGAAAAAGAAATGAAAAAACAAAAAAAAATAGAAAAAG
AAAGAAAAAAGAAAGAAGAAAAGGAAAAGAAAAAGAAAAAACATGATAAGGA
AAATGAAGAAACAATGCAACAACCAGATCAAACAAGTGAAGAAACCAACAATG
AAATTATGGTACCATTACCAAGTCCATTGACAGACGTAACTACACCAGAAGAAC
ACAAAGAAGGAGAACACAAAGAAGAAGAACACAAAGAAGGAGAACACAAAGA -continued Plasmodium falciparum glutamic acid-rich protein (Pf-GARP)

```
AGGAGAACACAAAGAAGAAGAACACAAAGAAGAAGAACACAAAAAAGAAGAA
CACAAATCAAAAGAACACAAATCAAAAGGAAAGAAAGATAAAGGAAAGAAAAGATA
AAGGAAAACATAAAAAAGCAAAAAAAGAAAAAGTAAAAAAACACGTAGTTAAAAA
TGTTATAGAAGATGAAGACAAAGATGGTGTAGAAATAATAAACTTAGAAGATAAAG
AGGCATGTGAAGAACAACACATAACAGTAGAAAGTAGACCACTAAGCCAACCACA
ATGTAAACTAATAGATGAACCAGAACAATTAACATTAATGGATAAATCAAAAGTTG
AAGAAAAAAACTTATCCATACAAGAGCAATTAATAGGTACCATAGGACGTGTTAAT
GTAGTACCCAGAAGAGATAATCATAAGAAAAAAATGGCGAAGATAGAGGAAGCTG
AACTTCAAAAACAGAAACATGTTGATAAGGAAGAAGACAAAAAAGAAGAATCCAA
AGAAGTAGAAGAAGAATCTAAAGAGGTACAAGAAGATGAAGAAGAAGTAGAAGAA
GATGAAGAAGAAGAAGAAGAAGAGGAAGAAGAAGAAGAAGAAGAAGAAGAAGAA
GAGGAAGAAGAAGAAGATGAAGTAGAAGAAGATGAAGATGATGCTGAAGAAGAT
GAAGATGATGCTGAAGAAGATGAAGATGATGCTGAAGAAGATGATGATGATGCTG
AAGAAGATGATGATGATGCTGAAGAAGATGATGATGAAGATGAAGATGAAGATGA
AGAAGAAGAAGAAGATGAAGAAGAAGAAGAAGAATCAGAAAAAAAAATAAAAAGA
AATTTGAGAAAAAATGCCAAAATTTAA Sequence Length: 2022 bp (SEQ ID NO: 12)
```

The contents of U.S. Pat. No. 9,662,379 including the sequences of PfGARp described therein are hereby incorporated by references in their entirety.

Also provided herein is an anti-malarial composition comprising the anti-*Plasmodium falciparum* PfGARP antibody disclosed herein.

In other embodiments, provided herein is a method of treating or reducing the severity of *P. falciparum* malaria in a subject in need thereof comprising administering to the subject an effective amount of the anti-*P. falciparum* PfG-ARP antibody described herein or an anti-malarial composition containing such an antibody.

For example, the methods provide that the subject is a mammal (e.g., a human). In examples, the subject is at least about 6-8 weeks of age. Moreover, the subject may be an adolescent female or a female of childbearing age.

In other embodiments, the methods of treating or reducing the severity of *P. falciparum* malaria in a subject in need thereof comprising administering to the subject an effective amount of the anti-*P. falciparum* PfGARP antibody described herein, or the anti-malarial composition, further comprises administering the anti-*P. falciparum* PfGARP antibody or an anti-malarial composition containing the antibody to the subject in combination with a secondary therapy or a secondary agent.

In examples, the second agent includes an inhibitor of parasite liver invasion. In other examples, the second agent is RTS,S (Mosquirix). In other examples, the second agent comprises an inhibitor of parasite red blood cell invasion (e.g., merozoite surface protein 1 (MSP-1)).

In aspects, provided herein is a method of killing *P. falciparum* or inhibiting *P. falciparum* growth in a subject comprising administering to the subject an effective amount of the anti-*P. falciparum* PfGARP antibody described herein, or an anti-malarial composition described herein. In examples, the method is associated with inducing loss of food vacuole integrity of *P. falciparum*. In other examples, the method is associated with inhibiting trophozoite development of *P. falciparum* in the absence of an immune effector cell or complement.

In other aspects, provided herein is a pharmaceutical composition comprising the anti-*P. falciparum* PfGARP antibody or an anti-malarial composition described herein, and one or more pharmaceutically acceptable excipients.

Also provided herein is a nucleic acid encoding the anti-*P. falciparum* PfGARP antibody described herein, e.g., a composition containing a PfGARP-specific antibody. Furthermore, an expression vector comprising the nucleic acid of the anti-*P. falciparum* PfGARP antibody is provided. Also, a cell comprising a vector is disclosed herein. In examples, the cell comprises a bacterial cell (e.g., a bacterial cell that includes the vector comprising the nucleic acid of the anti-*P. falciparum* PfGARP antibody. Other features and advantages of the invention will be apparent from the following description of the preferred embodiments thereof, and from the claims.

In other embodiments, an anti-*Plasmodium falciparum*: (*P. falciparum*) PfGARP antibody comprises one or more of the amino acid sequences set forth in SEQ ID NO: 1 (complementary determining region (CDR)1; DTYIH (SEQ ID NO: 13)), SEQ ID NO: 2 (CDR2; RIDPANYDT-KYDPKFQG (SEQ ID NO: 2)), and SEQ ID NO: 3 (CDR3; FGGTKLRFAY (SEQ ID NO: 3)); and a light chain variable region comprising the amino acid sequences set forth in SEQ ID NO: 4 (CDR1; KSSQSVLYSSNQRNYLA (SEQ ID NO: 4)), SEQ ID NO: 5 (CDR2; WASTRES (SEQ ID NO: 5)), and SEQ ID NO: 6 (CDR3; LQHFSSWT (SEQ ID NO: 6)). In another embodiment, the antibody comprises one or more sequences, each of the sequences that have at least 50% identity to SEQ ID NO: 1, 2, 3, 4, 5, and/or 6 and comprise a binding specificity to an operative epitope of PfGARP comprising or consisting of the amino acid sequence, EDKDGVEI (SEQ ID NO: 1). For example, the amino acid sequence a CDR described herein is at least 50%, at least 55%, at least 60%, at least 65%, at least 70%, at least 75%, at least 80%, at least 85%, at least 90%, at least 95%, at least 98%, at least 99%, or 100% identity to one or more of the CDR reference sequences described above (SEQ ID NO: 1, 2, 3, 4, 5, and/or 6).

In some examples, the anti-*P. falciparum* PfGARP antibody of claim 1, wherein said heavy chain variable region comprises the amino acid sequence set forth in SEQ ID NO: 7 and said light chain variable region comprises the amino acid sequence set forth in SEQ ID NO: 8. In another example, the heavy chain variable region comprises an amino acid sequence that is at least 50% identical to the amino acid sequence of SEQ ID NO: 7 and wherein said light chain variable region comprises an amino acid sequence that is at least 50% identical to the amino acid sequence of SEQ ID NO: 8.

The invention also encompasses a *P. falciparum* PfGARP antibody that comprises one or more sequences of amino acid sequences that have at least 50% identity to SEQ ID NO: 1, 2, 3, 4, 5, and/or 6 and comprise a binding specificity to an epitope of PfGARP comprising or consisting of the amino acid sequence, EDKDGVEI (SEQ ID NO: 1).

1. A method of inducing loss of food vacuole integrity of a *Plasmodium* sp., e.g., *P. falciparum*, organism comprising contacting the organism with a non-small molecule compound and/or a method of inhibiting trophozoite development of a *Plasmodium* sp. organism comprising contacting the organism with a non-small molecule compound are also within the invention. A small molecule is one that is less than 500 Daltons in molecular mass. For example, the methods comprise a compound is greater than 500 Daltons, e.g., greater than 600 Daltons, 700 Daltons, 800 Daltons, 900 Daltons, or 1 kDa. For example, the methods do not comprise chloroquine. In one example, the compound binds to a PfGARP antigen, e.g., wherein said antigen comprises an epitope of PfGARP comprising or consisting of the amino acid sequence, EDKDGVEI (SEQ ID NO: 1), e.g., the compound comprises the antibody described above. For example, the antibody comprises SEQ ID NO: 1, 2, 3, 4, 5, or 6, or a combination of those sequences, or each of the CDRs defined by SEQ ID NO: 1, 2, 3, 4, 5, or 6.

In some examples, the method comprises an anti-*P. falciparum* PfGARP antibody as described above, e.g., wherein the heavy chain variable region comprises the amino acid sequence set forth in SEQ ID NO: 7 and the light chain variable region comprises the amino acid sequence set forth in SEQ ID NO: 8. In another example, the method comprises a heavy chain variable region comprises an amino acid sequence that is at least 50% identical to the amino acid sequence of SEQ ID NO: 7 and wherein the light chain variable region comprises an amino acid sequence that is at least 50% identical to the amino acid sequence of SEQ ID NO: 8.

Also within the invention is a method of activating Programmed Cell Death of a *Plasmodium* sp., e.g., *P. falciparum*, organism comprising contacting the organism with a PfGARP-binding compound. For example, Programmed Cell Death comprises apoptosis. For example, the methods comprise a compound is greater than 500 Daltons, e.g., greater than 600 Daltons, 700 Daltons, 800 Daltons, 900 Daltons, or 1 kDa. For example, the compound binds to a PfGARP antigen, e.g., the antigen comprises an epitope of PfGARP comprising or consisting of the amino acid sequence, EDKDGVEI (SEQ ID NO: 1). In example, the compound comprises an antibody such as the antibody or antibodies described above.

In some examples, the compound is an antibody as described above, e.g., the antibody comprises SEQ ID NO: 1, 2, 3, 4, 5, or 6, or a combination of those sequences, or an antibody comprising each of the CDRs defined by SEQ ID NO: 1, 2, 3, 4, 5, or 6.

In some examples, the method of activating Programmed Cell Death comprises an anti-*P. falciparum* PfGARP antibody as described above, e.g., wherein the heavy chain variable region comprises the amino acid sequence set forth in SEQ ID NO: 7 and the light chain variable region comprises the amino acid sequence set forth in SEQ ID NO: 8. In another example, the method of activating Programmed Cell Death comprises a heavy chain variable region comprises an amino acid sequence that is at least 50% identical to the amino acid sequence of SEQ ID NO: 7 and wherein the light chain variable region comprises an amino acid sequence that is at least 50% identical to the amino acid sequence of SEQ ID NO: 8.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, Genbank/NCBI accession numbers, and other references mentioned herein are incorporated by reference in their entirety. In the case of conflict, the present specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A, 1B and 1C are representative of 5 independent experiments. FIGS. 1D, E, and F are representative of 3 independent experiments.

FIG. 1G is representative of 3 independent experiments.

FIG. 1H shows longer term parasite growth studies with and without anti-PfGARP antisera which conclusively demonstrated that anti-PfGARP antibodies killed the parasite (as opposed to arresting the development). Bars represent the mean of 3 independent replicates with each replicate performed in triplicate. Error bars represent SEMs.

FIG. 1I is representative of 3 independent experiments.

FIG. 1J is representative of 3 independent experiments.

FIG. 1K is representative of 3 independent experiments.

FIG. 1F is a bar graph showing that anti-PfGARP mAh inhibits parasite growth. Recombinant monoclonal anti-PfGARP produced from VH and VF sequence of mAh 7899 inhibits parasite growth. Ring stage 3D7 parasites were cultured in the presence of media alone, recombinant anti-fluorescein (250 µg/ml) or recombinant anti-PfGARP monoclonal antibody (250 µg/ml). FIG. 1F is representative of 3 independent experiments.

FIG. 2A are images showing that uninfected and infected RBCs were probed with mouse anti-PfGARP prepared by DNA vaccination (green) and rabbit anti-PfMSP-4 (red) and counterstained with 4',6'-diamidino-2-phenylindole (DAPI) to label parasite nuclei. PfGARP is detected on early, mid and late-trophozoite-infected RBC membranes and does not co-localize with PfMSP-4 (which localizes to the parasite membrane, scale bars 5 µm). FIG. 2A is representative of 5 independent experiments.

FIG. 2B are images showing that trophozoite-infected RBCs do not label when probed with pre-immune mouse sera (scale bars 5 µm). FIG. 2B is representative of 5 independent experiments.

FIG. 2C is an image showing that non-permeabilized, non-fixed trophozoite-infected RBCs were probed with mouse anti-PfGARP and detected with anti-mouse antibodies conjugated to 10-nm gold particles. Samples were processed for transmission electron microscopy. Anti-PfGARP bound to the outer RBC membrane of all trophozoite infected RBCs examined (>100). Pre-immune sera failed to bind to any trophozoite infected RBCs (>100 examined). FIG. 2C is representative of 3 independent experiments.

FIG. 2D is an image showing that non-permeabilized, non-fixed trophozoite-infected RBCs were probed with mouse anti-PfGARP and detected with anti-mouse antibodies conjugated to 10-nm gold particles. Samples were processed for transmission electron microscopy. Anti-PfGARP bound to the outer RBC membrane of all trophozoite infected RBCs examined (>100). Pre-immune sera failed to bind to any trophozoite infected RBCs (>100 examined). FIG. 2D is representative of 3 independent experiments.

FIG. 3A are images showing ring stage 3D7 parasites that were cultured for 24-30 hours in the presence of 10% pre-immune mouse sera or anti-PfGARP mouse sera generated by DNA vaccination. Representative dot plots demonstrating iRBCs with higher DNA content (mature parasites) in the upper gate, lower DNA content in the middle gate (immature and dying parasites), and uninfected RBCs in the lowest gate. All data are representative of 3 independent experiments.

FIG. 3B is a graph showing the that the binding of polyclonal anti-PfGARP antibodies to the iRBCs in upper two gates and uninfected RBCs in the lowest gate. All data are representative of 3 independent experiments. FIG. 3C is a graph showing incubation with anti-PfGARP results in activation of caspase-like proteases, assessed by Apostat staining. All data are representative of 3 independent experiments.

FIG. 3D is a graph showing incubation with anti-PfGARP results in DNA fragmentation, assessed by TUNEL staining in parasites present in the upper gate. All data are representative of 3 independent experiments.

FIG. 4A is a graph showing that Tanzanian children with undetectable anti-PfGARP IgG antibodies measured at 48 weeks of age (n=126 individuals who contributed 7,327 weeks of follow-up) had a 2.5-fold higher risk of developing severe malaria compared to children who had detectable IgG anti-PfGARP antibodies (n=120 individuals who contributed 8,410 weeks of follow-up, 95% CI [1.2, 5.5], P=0.018). Error bars represent SEM adjusted for repeated measures.

FIG. 4B is a graph showing that Kenyan males with undetectable IgG anti-rPfGARP-A antibodies (n=61 individuals who contributed 1,018 weeks of follow-up blood smears), had 1.97 fold higher parasite densities over 18 weeks of follow-up compared to individuals with detectable IgG anti-rPfGARP-A antibodies (n=74 individuals who contributed 1,237 weeks of follow-up blood smears) 95% CI [0.94, 4.23], P=0.012. Columns depict least-square mean parasitemia; error bars depict SEM.

FIG. 5A is a graph showing that animals were intradermally injected with 50 µg of PfGARP-A mRNA-LNP (n=5 monkeys) or 50 µg of poly(C) RNA-LNP (negative control, n=4 monkeys) at weeks 0, 3 and 6 and PfGARP-specific IgG titers were determined. Bars represent titer, error bars represent SEMs.

FIG. 5B is a graph showing vaccinated Aotus monkeys were challenged IV with $10^4$ *P. falciparum* FVO strain infected RBC on day 63 and parasitemia was followed daily. Control monkeys had significantly higher parasitemia than monkeys immunized with PfGARP-A on day 12 (P<0.009) with a 4.6-fold higher parasitemia on day 13, the final day with complete follow-up of all monkeys (P<0.001). On day 13, all control monkeys required anti-malarial treatment for high parasitemia (indicated by 4×P). On day 16, one vaccinated monkey required anti-malarial treatment for high parasitemia, (1×P). On day 17, one vaccinated monkey required anti-malarial treatment for high parasitemia and one vaccinated monkey required anti-malarial treatment for low hemoglobin (1×H). On day 18, two vaccinated monkeys required anti-malarial treatment for low hemoglobin (2×H).

FIG. 6A is an image of an SDS-PAGE gel of purified recombinant PfGARP-A (250 ng). FIG. 6A is representative of 5 independent experiments.

FIG. 6B is an image of extracts prepared from uninfected or 3D7 strain trophozoite-infected RBCs, or recombinant PfGARP-A were analyzed by western blot. The blot was probed with anti-PfGARP-A murine polyclonal sera generated by plasmid immunization and anti-MSP2 (rabbit polyclonal sera) and detected with anti-mouse IgG (red) and anti-rabbit IgG (green). FIG. 6B is representative of 5 independent experiments.

FIG. 6C in image of extracts prepared from uninfected or 3D7 strain trophozoite-infected RBCs, or recombinant PfGARP-A were analyzed by western blot. The blot was probed with pre-immune mouse sera and anti-MSP2 (rabbit polyclonal sera) and detected with anti-mouse IgG (red) and anti-rabbit IgG (green). FIG. 6C is representative of 5 independent experiments.

FIGS. 7A, 7B, 7C, and 7D are representative of 5 independent experiments.

FIGS. 8A-8D are images showing the purification of anti-PfGARP antibodies from human (FIGS. 8A and 8B) and mouse (FIGS. 8C and 8D) serum. Sera was affinity purified using PfGARP-A coupled to Sepharose beads. The specificity of the purified anti-PfGARP antibodies was determined by western blot on extracts prepared from unsynchronized 3D7 parasite infected RBCs. In all panels, Fane 1-3D7 infected RBCs extracted in RIPA buffer, Lane 2—uninfected RBCs extracted in RIPA buffer.

FIG. 8A is an image of a blot probed with anti-PfGARP purified from serum pooled from adults living in a holoendemic area of Tanzania (2 ug/ml). FIG. 8A is representative of 2 independent experiments.

FIG. 8B is an image of a blot probed with anti-PfGARP purified from serum of malaria-naive human immunoglobulin (2 ug/ml). FIG. 8B is representative of 2 independent experiments.

FIG. 8C is an image of a blot probed with anti-PfGARP purified from serum prepared from PfGARP-A immunized mice (10 ug/ml). FIG. 8C is representative of 2 independent experiments.

FIG. 8D is an image of a blot probed with anti-PfGARP purified from serum of malaria-naive human immunoglobulin (10 ug/ml). FIG. 8D is representative of 2 independent experiments.

FIG. 9A is a graph showing the kinetics of binding between rec mAb7899 and PfGARP-A was measured in in duplicate in two independent experiments 95% confidence intervals (CI) shown by dashed lines. Error bars represent standard deviations (n=4, number of replicates for each concentration point in two experiments). Formula shows linear regression. V, initial velocity of binding; c, concentration of biotinylated rec mAb7899; min, minutes, MFI, Median Fluorescence Intensity.

FIG. 9B is an image showing epitope mapping of rec mAb7899. A custom 15-mer peptide microarray was printed and contained 264 different peptides which spanned the PfGARP-A sequence (aa 410-673). The peptides overlapped by a single amino acid and were printed in duplicate, framed by HA control peptides. The array was probed with rec mAb7899 (red) and anti-HA (green) and imaged on a LI-COR Odyssey.

FIG. 9C is a bar graph showing the lactate levels measured in culture supernatant from FIG. 9B. Error bars represent SEMs. P value calculated by non-parametric Mann-Whitney U test is indicated. Panels A and C are representative of 2 independent experiments. Panels B is representative of 3 independent experiments.

FIG. 9D is a bar graph showing ring stage 3D7, D10, or Dd2 parasites were cultured in the presence of media alone or recombinant anti-PfGARP Fab antibody (1 mg/ml) for 48 hrs at 37° C. and ring or early trophozoite stage parasites were enumerated by microscopy. Bars represent the mean parasitemia enumerated on two slides, error bars represent SEMs. P values calculated by non-parametric Mann-Whitney U test are indicated. Data representative of two independent experiments.

FIG. 9E is an image showing epitope mapping of monospecific, polyclonal anti-PfGARP-A. A custom 15-mer peptide microarray was printed that contained 264 different peptides which spanned the PfGARP-A sequence (aa 410-673). The peptides overlapped by a single amino acid and were printed in duplicate.

FIG. 10A is an image depicting the targeting strategy for creating PfGARP KD parasites.

FIG. 10B is an image of an immunoblot analysis of 3D7-PfGARP-KD. Parasites were sorbitol-synchronized at the ring stage and incubated with or without anhydrotetracycline (Atc) for 20 hours and probed with anti-V5. The expected molecular weight of the PfGARP-V5 tagged protein is 124 kDa, however its apparent mobility is 165 kDa due to its acidic composition. Lane 1, uninfected RBCs, Lane 2-3D7-PfGARP-KD infected RBCs cultured without ATc, lane 3, 3D7-PfGARP-KD infected RBCs cultured with ATc. FIG. 10B is representative of 3 independent experiments.

FIG. 10C is a graph of growth curves for 3D7-PfGARP-KD parasites. Ring-stage parasites were cultured with or without ATc. Parasitemia was measured by microscopy. Each data point represents the mean of 3 replicates, error bars indicate SEM. FIG. 10C is representative of 5 independent experiments.

FIG. 10D is an image showing the expression of PfGARP on the surface of human RBCs infected with 3D7-PfGARP KD parasites. Ring stage 3D7-PfGARP-KD parasites were cultured to the trophozoite stage in the absence (−) or presence (+) of ATc. PfGARP expression on surface of infected human RBCs (fixed but not permeabilized) was determined by flow cytometry, using monoclonal anti-V5 as primary and anti-mouse IgG-FITC as secondary antibody. Infected RBCs were gated and identified as described in FIG. 1H. Overlaid histograms demonstrate PfGARP expression on surface of infected RBCs cultured in the absence (FIG. 10D) of ATC. FIG. 10D is representative of 3 independent experiments.

FIG. 10E is an image showing the expression of PfGARP on the surface of human RBCs infected with 3D7-PfGARP KD parasites. Ring stage 3D7-PfGARP-KD parasites were cultured to the trophozoite stage in the absence (−) or presence (+) of ATc. PfGARP expression on surface of infected human RBCs (fixed but not permeabilized) was determined by flow cytometry, using monoclonal anti-V5 as primary and anti-mouse IgG-FITC as secondary antibody. Infected RBCs were gated and identified as described in FIG. 1H. Overlaid histograms demonstrate PfGARP expression on surface of infected RBCs cultured in the presence (FIG. 10E) of ATC. FIG. 10E is representative of 3 independent experiments.

FIG. 10F is a bar graph showing a growth inhibition assay using 10% anti-rPfGARP-A antisera or pre-immune antisera on 3D7-PfGARP-KD parasites cultured with or without ATC. Bars represent anti-PfGARP mediated killing relative to pre-immune sera. Error bars represent SEM. FIG. 10F is representative of 3 independent experiments.

FIGS. 11A-11E are images of immunolocalization of PfGARP by immuno-gold electron microscopy in permeabilized, fixed infected and uninfected RBCs.

FIG. 11A is an image of uninfected RBC that were incubated with anti-rPfGARP polyclonal mouse serum and probed with anti-mouse IgG labeled with 10 nm gold particles. PfGARP was only localized to the outer leaflet of trophozoite infected RBCs (yellow arrow) but absent in ring and schizont infected RBCs. Figures labeled with primes represent higher magnifications views of the parent figure. FIG. 11A is representative of 2 independent experiments.

FIG. 11B is an image of ring-infected RBC incubated with anti-rPfGARP polyclonal mouse serum and probed with anti-mouse IgG labeled with 10 nm gold particles. PfGARP was only localized to the outer leaflet of trophozoite infected RBCs (yellow arrow) but absent in ring and schizont infected RBCs. Figures labeled with primes represent higher magnifications views of the parent figure. FIG. 11B is representative of 2 independent experiments.

FIG. 11C is an image of schizont infected RBC incubated with anti-rPfGARP polyclonal mouse serum and probed with anti-mouse IgG labeled with 10 nm gold particles. PfGARP was only localized to the outer leaflet of trophozoite infected RBCs (yellow arrow) but absent in ring and schizont infected RBCs. Figures labeled with primes represent higher magnifications views of the parent figure. FIG. 11C is representative of 2 independent experiments.

FIG. 11D is an image of trophozoite infected RBC incubated with anti-rPfGARP polyclonal mouse serum and probed with anti-mouse IgG labeled with 10 nm gold particles. PfGARP was only localized to the outer leaflet of trophozoite infected RBCs (yellow arrow) but absent in ring and schizont infected RBCs. Figures labeled with primes represent higher magnifications views of the parent figure. FIG. 11D is representative of 2 independent experiments FIG. 11E is an image of trophozoite infected RBC incubated with control mouse serum and probed with anti-mouse IgG labeled with 10 nm gold particles. PfGARP was only localized to the outer leaflet of trophozoite infected RBCs (yellow arrow) but absent in ring and schizont infected RBCs. Figures labeled with primes represent higher magnifications views of the parent figure. FIG. 11E is representative of 2 independent experiments.

FIG. 12A are images showing that uninfected and infected RBCs were probed with rabbit anti-glycophorin A (green) and recombinant DNA vaccine immunized mouse anti-PfGARP (red) and counterstained with 4',6'-diamidino-2-phenylindole (DAPI) to label parasite nuclei. PfGARP is detected only in trophozoite-infected RBCs and co-localizes with human glycophorin A on the RBC membrane. Scale bars for all the images are 5 µm. FIG. 12A is representative of 3 independent experiments.

FIG. 12B are images showing that both early and late-trophozoite-infected RBCs do not label when probed with pre-immune mouse sera. Scale bar for all the images is 5 µm. FIG. 12B is representative of 3 independent experiments.

FIG. 2A and FIG. 13 show very similar localization for PfGARP. Scale bar is 5 µm. Data are representative of 3 independent experiments.

FIG. 14 are images showing that PfGARP does not co-localize with knobs in trophozoite infected RBCs. Immunolocalization of PfGARP by immuno-gold electron microscopy in permeabilized, fixed trophozoite infected RBC with knobs. PfGARP was not present on knobs (yellow arrow) associated with adhesion of parasite and severe disease only localized to the outer leaflet of trophozoite infected RBC membrane (red arrow). Data are representative of 2 independent experiments.

FIGS. 15A and 15B are representative of all trophozoites observed in 3 independent experiments. FIGS. 15C and 15D are enlarged views from panels FIG. 15A and FIG. 15B respectively. By 24 hours after the addition of anti-PfGARP antisera, 100% of the parasites showed disruption of their food vacuole as evidenced by transmission electron microscopy. Data are representative of 2 independent experiments.

FIGS. 18A-18E are images depicting that the PEXEF element is processed and cleaved in mature PfGARP.

FIG. 18A is a schematic depicting the binding sites for the peptide specific antibodies.

FIG. 18B is an image of an immunoblot of recombinant PfGARP-A (lane 1), recombinant full length PfGARP (lane 2), and an extract of trophozoite infected RBCs (lane 3) probed with antisera raised against aa 504-522 of PfGARP. Only antibodies raised against aa 504-522 recognized native PfGARP in trophozoite infected RBCs, while the anti-sera raised against aa 31-48 only recognized the full length recombinant PfGARP confirming that the PEXEF element is cleaved during the processing of native PfGARP. Abbreviations: SP-signal peptide, Pxl-pexel element. Data are representative of 3 independent experiments.

FIG. 18C is an image of an immunoblot of recombinant PfGARP-A (lane 1), recombinant full length PfGARP (lane 2), and an extract of trophozoite infected RBCs (lane 3) probed with pre immune sera. Only antibodies raised against aa 504-522 recognized native PfGARP in trophozoite infected RBCs, while the anti-sera raised against aa 31-48 only recognized the full length recombinant PfGARP confirming that the PEXEF element is cleaved during the processing of native PfGARP. Abbreviations: SP-signal peptide, Pxl-pexel element. Data are representative of 3 independent experiments.

FIG. 18D is an image of an immunoblot of recombinant PfGARP-A (lane 1), recombinant full length PfGARP (lane 2), and an extract of trophozoite infected RBCs (lane 3) probed with antisera raised against aa 31-48 of PfGARP. Only antibodies raised against aa 504-522 recognized native PfGARP in trophozoite infected RBCs, while the anti-sera raised against aa 31-48 only recognized the full length recombinant PfGARP confirming that the PEXEL element is cleaved during the processing of native PfGARP. Abbreviations: SP-signal peptide, Pxl-pexel element. Data are representative of 3 independent experiments.

FIG. 18E is an image of an immunoblot of recombinant PfGARP-A (lane 1), recombinant full length PfGARP (lane 2), and an extract of trophozoite infected RBCs (lane 3) probed with pre immune antisera. Only antibodies raised against aa 504-522 recognized native PfGARP in trophozoite infected RBCs, while the anti-sera raised against aa 31-48 only recognized the full length recombinant PfGARP confirming that the PEXEL element is cleaved during the processing of native PfGARP. Abbreviations: SP-signal peptide, Pxl-pexel element. Data are representative of 3 independent experiments.

FIG. 19A is a graph showing that 3D7 parasites were synchronized to the ring stage and incubated at 5% parasitemia in the presence of no sera, pre-immune and anti-PfGARP mouse sera at 1:10 dilution prepared by immunization with rPfGARP-A. FIG. 19A is representative of 5 independent experiments.

FIG. 19B is a graph showing that 3D7 parasites were synchronized to the ring stage and incubated at 5% parasitemia in the presence of no sera, pre-immune and anti-PfGARP mouse sera at 1:10 dilution prepared by DNA vaccination. FIG. 19B is representative of 5 independent experiments.

FIG. 19C is a bar graph showing that parasites were also cultured in the presence of normal mouse IgG or purified mouse anti-PfGARP IgG at 100 µg/ml. FIG. 19C is representative of 3 independent experiments.

FIG. 19D is a bar graph showing that parasites were cultured in the presence of human IgG obtained from malaria naive individuals or anti-PfGARP IgG isolated from adults residents of the Tanzanian field site at 100 µg/ml. Parasites were cultured for 36 hrs. and trophozoite stage parasites were enumerated and the percent of trophozoite infected RBCs was calculated. Bars represent the mean of 5 independent replicates with each replicate performed in triplicate. Error bars represent SEMs. Comparisons between pre and post immune mouse sera and between total IgG and anti-PfGARP IgG treated cultures by non-parametric Mann-Whitney U test is indicated. FIG. 19D is representative of 3 independent experiments.

FIG. 19E is a graph showing that 3D7 parasites were synchronized to the ring stage and incubated with anti-PfGARP polyclonal mouse serum. Cultures were incubated for 36 hours with samples collected at 12 hour intervals and the number of trophozoites was enumerated. Bars represent the mean of 3 independent replicates with each replicate performed in triplicate. Error bars represent SEMs. The graph is representative of 3 independent experiments. The trophozoites enumerated in the anti-PfGARP treatment at 36 hr were severely pyknotic. Data are representative of 5 independent experiments.

FIGS. 20A, 20B, 20C and 20D are representative of 3 independent experiments.

FIGS. 22A-22C are graphs showing vaccination with rPfGARP-A emulsified in Ribi adjuvant protects monkeys from challenge with P. falciparum.

FIG. 22A is a graph showing animals injected subcutaneously with 50 µg of rPfGARP-A emulsified in 100 µL of Ribi (n=5 monkeys) or Ribi alone (negative control, n=4 monkeys) at weeks 0, 3 and 6 and PfGARP-A specific IgG titers were determined. Bars represent titer, error bars represent SEMs.

FIG. 22B is a graph showing vaccinated Aotus monkeys that were challenged IV with $10^4$ P. falciparum FVO strain infected RBC on day 63 and parasitemia was followed daily. Control monkeys had significantly higher parasitemia on days 7-12 compared to PfGARP vaccinated animals. On day 11, the final day with complete follow-up of all monkeys, controls had 3.5 fold higher parasitemia compared to PfG-ARP vaccinated monkeys. Four control monkeys met pre-specified criteria for drug treatment on day 11 and the final control monkey met criteria on day 12. On Day 11, one PfGARP vaccinated monkey was drug treated despite not meeting pre-specified criteria. * indicates $P<0.05$. ** indicates $P<0.01$.

FIG. 22C is a graph showing the individual parasitemia data from monkey trial presented in FIG. 22B.

FIGS. 24A-24D Are images depicting that mAh anti-PfGARP blocks parasite growth. FIG. 24A is a bar graph showing parasitemia with no IGg (far left), mAh 7857 (middle bar graph) and mAh 7899 (right bar graph). FIG. 24B is a schematic depicting the CDR regions (underlined) on the heavy and light chains. FIG. 24C is an image of an image of an electrophoretic gel of proteins carried out under reduced and non-reduced conditions. FIG. 24D is a schematic of PfGARP domains.

FIG. 25A is an image of goat anti-mouse IgG (H+F) DyFight680 (0.2 µg/ml). After 15 min pre-swelling in washing buffer and 30 min incubation in blocking buffer, a GARP peptide microarray copy was initially incubated with the secondary antibody for 45 min at room temperature to analyze background interactions with the antigen-derived peptides that could interfere with the main assay. FIG. 25B is an image of an adjusted scan showing that at scanning intensities of 7/7 (red/green), no background interaction of the secondary antibody with the linear peptides was observed, even upon significant increase of brightness and contrast. Data quantification with PepSlide® Analyzer was hence omitted.

FIG. 26A is an image showing epitope mapping using GARP mouse mAh at 1 µg/ml. FIG. 26B is an image showing epitope mapping using control staining. FIG. 26C is a graph showing the fluorescence intensity using GARP mouse monoclonal antibody. A peak was observed with the sequence EDKDGVEI (SEQ ID NO: 1).

FIGS. 27A and 27B are images depicting that cross-linking of surface expressed PfGARP is not necessary for the parasiticidal effect of anti-PfGARP. Recombinant monoclonal Fab anti-PfGARP inhibited parasite growth. FIG. 27A is an image of SDS-PAGE analysis of purified Fab anti-PFGARP showing a single band comprising the Vh and Vl sequences. FIG. 27B is a graph showing that the Ring stage 3D7 parasites were cultured in the presence of media alone or recombinant anti-PfGARP Fab antibody (1 mg/ml).

DETAILED DESCRIPTION

Figure 1G:
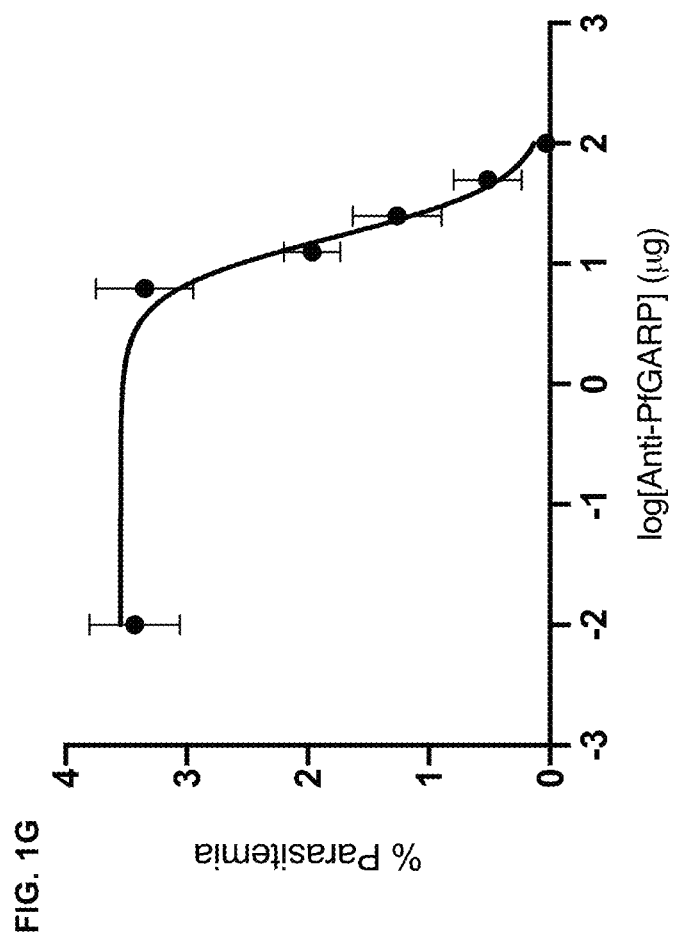
FIG. 1G is a graph showing the $IC_{50}$ of anti-PfGARP, parasites that were incubated in the presence of purified anti-PfGARP IgG (isolated from polyclonal sera produced in mice against rPfGARP-A) in a serial dilution from 100 μg/ml (FIG. 1G). For all conditions, ring stage parasites were cultured for 48 hrs at 37° C. and ring or early trophozoite stage parasites were enumerated by microscopy. Points represent the mean of 3 independent replicates with each replicate performed in triplicate. Error bars represent SEMs. P value were calculated by non-parametric Mann-Whitney U test are indicated. All the panels are representative of at least 3 independent experiments.

The invention provides an anti-*Plasmodium falciparum* (*P. falciparum*) PfGARP antibody comprising a heavy chain variable region comprising the amino acid sequences set forth in SEQ ID NO: 1 (complementary determining region (CDR)1), SEQ ID NO: 2 (CDR2), and SEQ ID NO: 3 (CDR3); and a light chain variable region comprising the amino acid sequences set forth in SEQ ID NO: 4 (CDR1), SEQ ID NO: 5 (CDR2), and SEQ ID NO: 6 (CDR3).

Antimalarial antibodies can activate programmed cell death (PCD) (e.g., anti-PfGARP activates or elicits programmed cell death in the parasite).

The malarial antigen, PfGARP, is useful as: 1) vaccine candidate with efficacy in non-human primates, 2) target of protective antibodies in humans, 3) target of antibodies that lead to parasite death, 4) target of antibodies that lead to caspase like activation and TUNEL staining (apoptosis), 5) target of antibodies that lead to mitochondrial depolarization (apoptosis), and 6) target of antibodies that lead to loss of food vacuole integrity.

Malaria caused by *Plasmodium falciparum* remains the leading single-agent killer of children, yet the promise of an effective vaccine remains unfulfilled. Using the differential, blood-stage proteome screening method, PF Glutamic Acid Rich Protein (PfGARP, PF3D7_0113000) was identified as a parasite antigen recognized by antibodies in plasma of children who are relatively resistant, but not by children who are susceptible, to *P. falciparum* malaria parasitemia.

PfGARP is an 80-kDa parasite antigen expressed on the exofacial surface of early to late trophozoite-infected erythrocytes. Antibodies to PfGARP kill trophozoite-infected erythrocytes in culture by inducing parasite programmed cell death, and vaccination with PfGARP partially protects against *P. falciparum* challenge in non-human primates. The longitudinal studies described herein revealed that Tanzanian children without anti-PfGARP antibodies experienced 2.5-fold higher risk of severe malaria and Kenyan adolescents and adults without anti-PfGARP antibodies had 2.0-fold higher parasite densities compared to individuals with these antibodies. By killing trophozoite-infected erythrocytes, PfGARP synergizes with other vaccines targeting hepatocyte invasion and erythrocyte invasion or egress.

In previous studies, a blood-stage proteome differential screening approach was developed to identify parasite antigens recognized by antibodies expressed by children who are relatively resistant but are not recognized by antibodies expressed by children who are susceptible to malaria infection (Raj, D. K. et al. *Science* 344, 871-877, (2014)).

This approach was modified to incorporate phage-display based library screening to increase throughput while decreasing the quantity of plasma necessary. The *P. falciparum* blood stage proteome was probed with plasma from resistant and susceptible two-year old children participating in the Tanzanian birth cohort (Mutabingwa, T. K. et al. *PLoS Medicine* 2, e407, (2005)) to identify parasite proteins that are the targets of protective antibody responses. Two-year olds were selected because, in the cohort, resistance to *P. falciparum* parasitemia is first detected at this age.

Twelve resistant and fourteen susceptible two-year old children were selected with matching for non-immune factors which may be related to resistance (Table 1). Relative resistance was determined based on the mean parasite density on all blood films collected between ages two and 3.5 years. Plasma collected at age two years (+/− two weeks) from the most resistant individuals was pooled and the most susceptible individuals and performed differential bio panning experiments on a *P. falciparum* 3D7 strain blood stage cDNA library constructed in T7 phage.

TABLE 1

Epidemiologic characteristics of resistant and susceptible individuals used in differential screening assays

| Variable | Resistant | Susceptible | P value* |
|---|---|---|---|
| Number of subjects | 12 | 14 | — |
| Hemoglobin Phenotype (% Sickle trait) | 25 | 14.3 | 0.918 |
| Sex (% female) | 25 | 50 | 0.190 |
| Weeks of follow-up (median [IQR]) | 143 [23.5] | 158 [16] | 0.047 |

TABLE 1-continued

Epidemiologic characteristics of resistant and susceptible
individuals used in differential screening assays

| Variable | Resistant | Susceptible | P value* |
|---|---|---|---|
| # Of blood smears from age 2-3.5 years (median [IQR]) | 14 [7.4] | 21 [8.5] | 0.0102 |
| # Of positive blood smears from age 2-3.5 years (median [IQR]) | 2.1 [1] | 5.8 [3.5] | 0.0024 |
| # Of anti-malarial treatment before 2 (median [IQR]) | 1.3 [1.1] | 2.3 [3.1] | 0.133 |
| Pregnancy malaria (%) | 25 | 21.4 | 0.300 |
| Maternal age (yrs, median [IQR]) | 27 [8] | 26.5 [6] | 0.833 |
| Birth Season (% in high season‡) | 41.7 | 42.9 | 0.952 |
| Subjects using bed net (%) | 0 | 100 | <0.001 |
| # Of previous pregnancies (median [IQR†]) | 2 [2] | 2.3 [2.1] | 0.760 |
| Parasite density (parasites per 200 WBCs§) at 2 year blood draw | 0 | 0 | 1 |
| Mean Parasite density (parasites per 200 WBCs) from age 0-2 years (median [IQR]) | 623 [952] | 1400 [736] | 0.1569 |
| Mean Parasite density (parasites per 200 WBCs) from ade 2-3.5 years (median [IQR]) | 7.1 [2.9] | 2258 [1569] | <0.001 |

*Comparisons of categorical variables by 2 tailed Fisher's exact test. Comparisons of continuous variables by Mann-Whitney U test
†Interquartile range
‡May-October
§White blood cells Recombinant phage ($1.0 \times 10^8$) were differentially bio-panned, sequenced n=100 differentially recognized clones, and identified 9 parasite genes whose protein products were uniquely recognized by antibodies in plasma from resistant, but not susceptible individuals (Table 2).

TABLE 2

Parasite genes identified by differential bio-panning of phage display library.
Results represent sequencing data from 100 phage clones

| Gene name | Gene ID & length in bp (Introns spliced out) | % Of Clones | Fragment size & nt. position in the gene |
|---|---|---|---|
| Glutamic acid-rich protein (GARP) | PF3D7_0113000 (2022) | 37 | 465 (1558-2022) |
| Glutamic acid-rich protein (GARP) | PF3D7_0113000 (2022) | 5 | 246 (1777-2022) |
| Glutamic acid-rich protein (GARP) | PF3D7_0113000 (2022) | 2 | 801 (1222-2022) |
| Heat shock protein 110 (HSP110) | PF3D7_0708800 (2622) | 2 | 650 (1764-2414) |
| Knob-associated histidine-rich protein (KAHRP) | PF3D7_0202000 (2312) | 4 | 241 (1309-1549) |
| Conserved Plasmodium protein | PF3D7_0418300 (2979) | 2 | 643 (1811-2453) |
| Rhoptry-associated membrane antigen (RAMA) | PF3D7_0707300 (2115) | 3 | 451 (953-1403) |
| High mobility group protein B1 (HMGPB1) | PF3D7_1202900 (294) | 2 | 140 (153-294) |
| Plasmodium exported protein (PHISTc) | PF3D7_0936800 (1152) | 3 | 303 (695-998) |
| Serine/threonine protein kinase, FIKK family | PF3D7_1039000 (3107) | 1 | 390 (1156-1546) |
| Ornithine aminotransferase | PF3D7_0608800 (1245) | 1 | 332 (914-1245) |
| 18S ribosomal RNA | PF3D7_0531600 (2092) | 26 | 670 (399-1068) |
| 60S ribosomal protein L5, putative | PF3D7_1424100 (549) | 11 | 460 (1-459) |

Based on its in silico properties, its high degree of enrichment (45 out of 100 differentially biopanned clones), and its representation by clones derived from three overlapping but distinct cDNAs, attention was focused on PfGARP, encoded by PF3D7_0113000.

In silico analysis (www.PlasmoDB.org and www.OrthoMCL.org) (Aurrecoechea, C. et al. *Nucleic Acids Research* 37, D539-543, (2009) and Chen, F. *Nucleic acids research* 34, D363-368(2006)) predicts that PF3D7_0113000 contains a 2,236 bp gene (PfGARP) that encodes an 80-kDa acidic protein, with one intron near its 5' end. PfGARP has synthetic orthologs in *P. praefalciparum*, *P. gaboni* and *P. reichenowi*, but not in any other malaria species, or other organism evaluated to date. PfGARP has no significant homology to proteins of known function and contains multiple complex repeat regions and extensive regions of low amino acid complexity with 50% of the protein composed of three amino acids (Lys, Glu, and Asp).

PfGARP expression is highly restricted to the early trophozoite stage (Lopez-Barragan, M. J. et al. *BMC Genomics* 12, 587(2011)) and the gene displays minimal sequence variation in the immuno-relevant region, the region encoded by the largest clone identified by resistant sera in the differential screens (nt 1,222-2,022). A recently reported deep-sequencing effort on 227 field samples identified only one non-synonymous SNP in the immunorelevant region (Manske, M. et al. *Nature* 487, 375-379, (2012)), while an expanded, as yet unpublished analysis of 3,248 field samples has provisionally identified 15 non-synonymous SNPs in the immuno-relevant region (https://www.malariagen.net/apps/pf/4.0/#doc=Doc*AboutData.htm).

Methods for Preventing or Treating an Infection or Severe Disease

Included herein is a method of preventing or treating an infection or severe disease, including malaria in a subject in need thereof. The method comprises administering to the subject an effective amount of the composition comprising the anti-*Plasmodium falciparum* (*P. falciparum*) PfGARP antibody. For example, methods for preventing or treating an infection or severe malarial disease include administering a composition comprising the anti-*Plasmodium falciparum* (*P. falciparum*) PfGARP antibody.

The methods for treating an infection or severe disease, (e.g., malaria) comprise administering to a subject a composition comprising the anti-*Plasmodium falciparum*: (*P. falciparum*) PfGARP antibody produced according to the methods described herein. Optionally, the antibody is administered in combination with methods for controlling the other symptoms of malarial disease. In particular, the combination treatment can include other anti-malarial agents. The combination therapy may include administration of the anti-*Plasmodium falciparum* (*P. falciparum*) PfGARP antibody.

The composition can be administered in a pharmaceutically or physiologically acceptable preparation or as a composition containing a physiologically acceptable carrier, excipient, or diluent, and administered to the tissues of the recipient organism of interest, including humans and non-human animals.

The anti-*Plasmodium falciparum*: (*P. falciparum*) PfGARP antibody (e.g., a composition comprising the anti-*Plasmodium falciparum* (*P. falciparum*) PfGARP antibody) can be prepared by re-suspending in a suitable liquid or solution such as sterile physiological saline or other physiologically acceptable injectable aqueous liquids. The amounts of the components to be used in such compositions are routinely determined by those having skill in the art.

For injectable administration, the composition (e.g., a composition comprising the anti-*Plasmodium falciparum* (*P. falciparum*) PfGARP antibody) is in sterile solution or suspension or can be resuspended in pharmaceutically- and physiologically-acceptable aqueous or oleaginous vehicles, which may contain preservatives, stabilizers, and material for rendering the solution or suspension isotonic with body fluids (i.e. blood) of the recipient. Non-limiting examples of excipients suitable for use include water, phosphate buffered saline, pH 7.4, 0.15 M aqueous sodium chloride solution, dextrose, glycerol, dilute ethanol, and the like, and mixtures thereof. Illustrative stabilizers include polyethylene glycol, proteins, saccharides, amino acids, inorganic acids, and organic acids, which may be used either on their own or as admixtures. The amounts or quantities, as well as the routes of administration used, are determined using methods known in the art, and correspond to the amounts used in similar types of applications or indications known to those of skill in the art.

A therapeutically effective amount of the composition (e.g., a composition comprising the anti-*Plasmodium falciparum* (*P. falciparum*) PfGARP antibody) in humans is determined using standard methods. For example, the composition (e.g., a composition comprising the anti-*Plasmodium falciparum*: (*P. falciparum*) PfGARP antibody) is administered thrice daily, twice daily, once daily, fourteen days on (four times daily, thrice daily or twice daily, or once daily) and 7 days off in a 3-week cycle, up to five or seven days on (four times daily, thrice daily or twice daily, or once daily) and 14-16 days off in 3 week cycle, or once every two days, or once a week, or once every 2 weeks, or once every 3 weeks.

In another example, the composition (e.g., a composition comprising the anti-*Plasmodium falciparum* (*P. falciparum*) PfGARP antibody) is administered once a week, or once every two weeks, or once every 3 weeks or once every 4 weeks for at least 1 week, in some embodiments for 1 to 4 weeks, from 2 to 6 weeks, from 2 to 8 weeks, from 2 to 10 weeks, or from 2 to 12 weeks, 2 to 16 weeks, or longer (e.g., 1, 2, 3, 4, 5, 6, 7, 8, 9, 10, 11, 12, 36, 48, or more weeks).

Pharmaceutical Compositions and Formulations

The present invention provides pharmaceutical compositions comprising an effective amount of a composition (e.g., a composition comprising the anti-PfGARP antibody) and at least one pharmaceutically acceptable excipient or carrier, wherein the effective amount is as described above in connection with the methods of the invention.

In one embodiment, the composition (e.g., a composition comprising the anti-*Plasmodium falciparum* (*P. falciparum*) PfGARP antibody) is further combined with at least one additional therapeutic agent in a single dosage form.

The term "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, or suitable mixtures thereof.

A pharmaceutical composition can be provided in bulk or in dosage unit form. It is especially advantageous to formulate pharmaceutical compositions in dosage unit form for ease of administration and uniformity of dosage. The term "dosage unit form" as used herein refers to physically discrete units suited as unitary dosages for the subject to be treated. Each unit containing a predetermined quantity of active compound is calculated to produce the desired therapeutic effect in association with the required pharmaceutical carrier. The specification for the dosage unit forms are dictated by and directly dependent on the unique characteristics of the active compound and the particular therapeutic effect to be achieved. A dosage unit form can be an ampoule, a vial, a suppository, a dragee, a tablet, a capsule, an IV bag, or a single pump on an aerosol inhaler.

In therapeutic applications, the dosages vary depending on the agent, the age, weight, and clinical condition of the recipient patient, and the experience and judgment of the clinician or practitioner administering the therapy, among other factors affecting the selected dosage. Generally, the dose is a therapeutically effective amount. Dosages can be provided in mg/kg/day units of measurement (which dose may be adjusted for the patient's weight in kg, body surface area in $m^2$, and age in years). Exemplary doses and dosages regimens for the compositions in methods of treating muscle diseases or disorders are described herein. The pharmaceutical compositions can take any suitable form (e.g., liquids, aerosols, solutions, inhalants, mists, sprays; or solids, powders, ointments, pastes, creams, lotions, gels, patches and the like) for administration by any desired route (e.g., pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). For example, a pharmaceutical composition of the invention may be in the form of an aqueous solution or powder for aerosol administration by inhalation or insufflation (either through the mouth or the nose), in the form of a tablet or capsule for oral administration; in the form of a sterile aqueous solution or dispersion suitable for administration by either direct injection or by addition to sterile infusion fluids for intravenous infusion; or in the form of a lotion, cream, foam, patch, suspension, solution, or suppository for transdermal or transmucosal administration.

In some examples the pharmaceutical composition comprises an injectable form. A pharmaceutical composition can also be in the form of an orally acceptable dosage form including, but not limited to, capsules, tablets, buccal forms, troches, lozenges, and oral liquids in the form of emulsions, aqueous suspensions, dispersions or solutions. Capsules may contain mixtures of a compound of the present invention with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc.

An exemplary pharmaceutical composition include those in the form of a sterile aqueous solution or dispersion suitable for parenteral administration. The term parenteral as used herein includes subcutaneous, intracutaneous, intravenous, intramuscular, intra-articular, intraarterial, intrasynovial, intrasternal, intrathecal, intralesional and intracranial injection or infusion techniques.

Examples of pharmaceutical composition can be in the form of a sterile aqueous solution or dispersion suitable for administration by either direct injection or by addition to sterile infusion fluids for intravenous infusion, and can comprise a solvent or dispersion medium containing, water, ethanol, a polyol (e.g., glycerol, propylene glycol and liquid polyethylene glycol), suitable mixtures thereof, or one or more vegetable oils. Solutions or suspensions of can be prepared in water suitably mixed with an adjuvant or other substance such as a surfactant. Dispersions can also be prepared, for example, in glycerol, liquid polyethylene glycols and mixtures of the same in oils.

The pharmaceutical compositions for use in the methods of the present invention can further comprise one or more additives in addition to any carrier or diluent (such as lactose or mannitol) in the formulation. The one or more additives can comprise or consist of one or more surfactants. Surfactants typically have one or more long aliphatic chains such as fatty acids which enables them to insert directly into the lipid structures of cells to enhance drug penetration and absorption. An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Thus, hydrophilic surfactants are generally considered to be those compounds having an HLB value greater than about 10, and hydrophobic surfactants are generally those having an HLB value less than about 10. However, these HLB values are merely a guide since for many surfactants, the HLB values can differ by as much as about 8 HLB units, depending upon the empirical method chosen to determine the HLB value. All percentages and ratios used herein, unless otherwise indicated, are by weight.

Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

Kits Comprising the Anti-*Plasmodium Lalciparum* (*P. Lalciparum*) PfGARP Antibody An anti-*Plasmodium falciparum* (*P. falciparum*) PfGARP antibody may be provided in a kit with equipment or materials for delivery (e.g., injection) to a subject.

The present invention also provides packaging and kits comprising pharmaceutical compositions for use in the methods of the present invention. The kit can comprise one or more containers selected from the group consisting of a bottle, a vial, an ampoule, a blister pack, and a syringe. The kit can further include one or more of instructions for use in treating and/or preventing a disease, condition or disorder of the present invention (e.g., an infection or severe disease, including malaria), one or more syringes, one or more applicators, or a sterile solution suitable for reconstituting a pharmaceutical composition of the present invention.

The following examples illustrate certain specific embodiments of the invention and are not meant to limit the scope of the invention.

Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

Example 1: Anti-PfGARP-A Mediates Growth Inhibition and Killing of Parasites In Vitro The polypeptide encoded by the differentially recognized, immuno-relevant region of PfGARP was expressed and purified from the referent strain 3D7 (nt 1,228-2,022, aa 410-673) in *Escherichia coli* and designated this recombinant protein rPfGARP-A (FIG. 6A). In addition, this immuno-relevant region was cloned into a eukaryotic expression plasmid (VR2001). To generate anti-PfGARP-A antisera, mice were immunized with either the recombinant protein (rPfGARP-A) in TiterMax adjuvant or the eukaryotic expression plasmid. In Western blot analysis, both protein and DNA immunized anti-PfGARP-A antisera recognized a ~100 kDa protein in trophozoite-infected RBCs (FIGS. 6B and 8C), this higher apparent molecular weight is consistent with PfGARP's acidic composition.

Growth inhibition assays (GIA) were performed using anti-PfGARP-A antisera prepared by either DNA or recombinant protein immunization (FIGS. 1A-1C). Parasites were synchronized to the ring stage, and then incubated with anti-PfGARP-A antisera or controls for 48 hours followed by enumeration of ring or early trophozoite stage parasites. Anti-PfGARP-A generated by DNA plasmid or recombinant protein-based immunization inhibited parasite growth by 94-99% across three parasite strains compared with controls (all P<0.001). One of the parasite strains tested, Dd2, expresses the previously identified (Manske, M. et al. Nature 487, 375-379, (2012)) variant allele (K551N) compared to the referent strain (3D7) used for the immunizations. In addition, anti-PfGARP-A generated by recombinant protein-based immunization inhibited parasite growth by 96-99% (all P<0.001) in two parasite lines that were freshly isolated from Tanzanian children and two parasite lines that were freshly isolated from Tanzanian adults (FIGS. 7A-7D).

Human polyclonal anti-PfGARP-A antibodies were purified from plasma pooled from adults living in the Tanzanian field using rPfGARP-A coupled to Sepharose beads (FIGS. 8A-8D) and demonstrated that these human anti-PfGARP-A antibodies significantly inhibited parasite growth by 94-99% across three parasite strains compared with controls (all P<0.001, FIGS. 1D-1F).

In addition, mouse polyclonal anti-PfGARP-A antibodies were purified from plasma pooled from rPfGARP-A immunized mice using rPfGARP-A coupled to Sepharose beads (FIGS. 8A-8D). Using purified anti-PfGARP-A, the $IC_{50}$ for parasite growth occurs at 16.8 µg of anti-PfGARP-A per ml of culture media (FIG. 1G).

To confirm that the decreased parasite growth observed in anti-PfGARP cultures was due to parasite death, not merely arrested growth, longer term parasite growth studies were performed with and without anti-PfGARP antisera (FIG. 1H). 3D7 parasites were synchronized to the ring stage and plated at 0.08% parasitemia in the presence of anti-PfGARP-A polyclonal mouse sera (1:10 dilution) or pre-immune sera (1:10 dilution) or no sera. Parasites were cultured for 7 days with daily enumeration by microscopy. Parasites treated with anti-PfGARP-A antisera never expanded in number and, by day two, had shrunken in size and appeared pyknotic. By day 4, the parasites were difficult to visualize as they had become small, pyknotic dots. By day 6, they were no longer identifiable as parasite infected RBCs. These data confirmed that anti-PfGARP antibodies, in the absence of complement or cellular effector functions, killed parasite infected RBCs.

To further quantify the parasiticidal effect of anti-PfGARP antibodies, growth inhibition assays (GIA) were performed and quantified parasite viability by flow cytometry using the mitochondrial membrane potential probe, JC-1. Ring stage parasites treated with anti-PfGARP antibodies showed marked loss of mitochondrial membrane potential (a characteristic of programmed cell death) within 12 hours with essentially all parasites losing their mitochondrial function within 24 hours (FIGS. 1I and 1J). The marked growth inhibition and mitochondrial membrane disruption mediated by anti-PfGARP1 antibodies occurred in the absence of cellular or complement-mediated effector mechanisms and appeared solely dependent on antigen-antibody engagement.

Figure 1K:
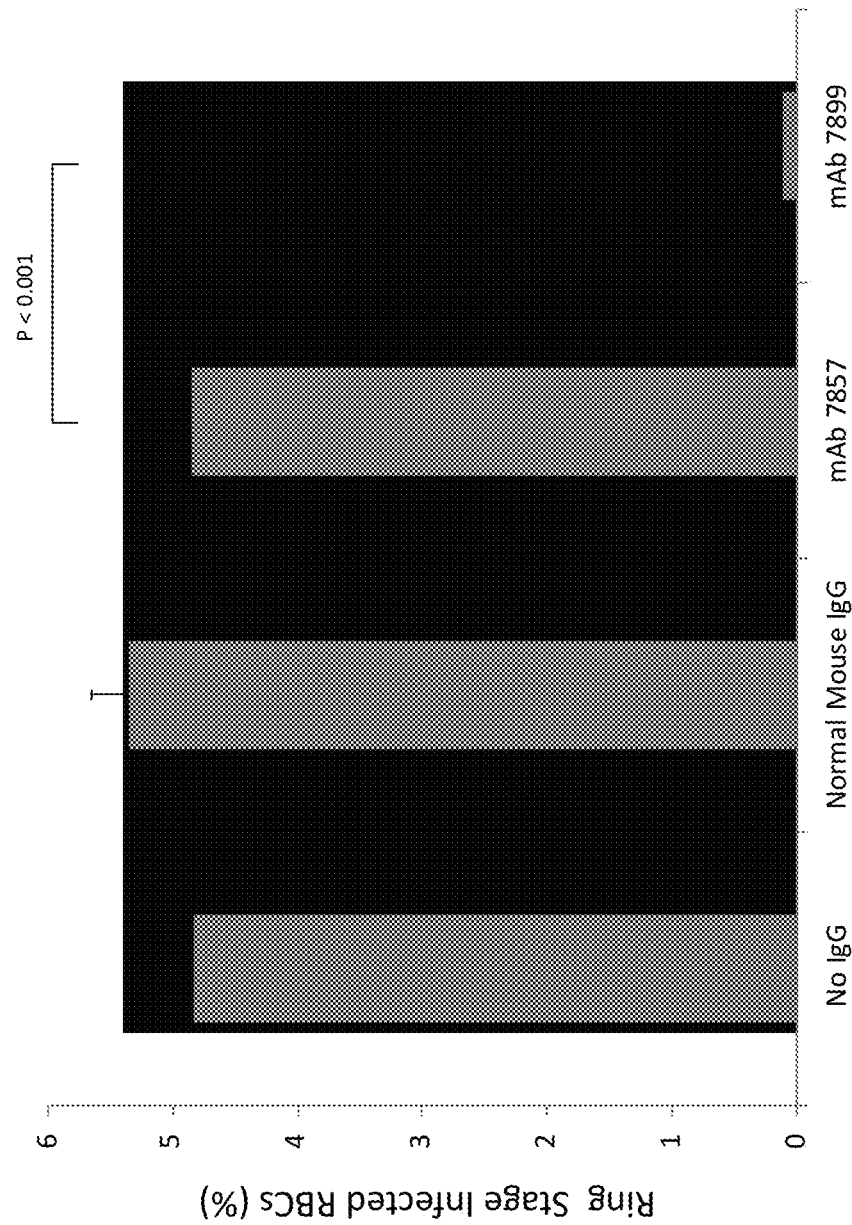
FIG. 1K is a bar graph showing that anti-PfGARP mAh inhibits parasite growth. Ring stage 3D7 parasites were cultured in the presence of media alone, normal mouse IgG (1 mg/ml) or anti-PfGARP monoclonal antibodies (mAh 7857 or mAh 7899, at 1 mg/ml). Ring stage 3D7 parasites were cultured in the presence of media alone, recombinant anti-fluorescein (250 µg/ml) or recombinant anti-PfGARP monoclonal antibody (250 µg/ml).
Figure 1L:
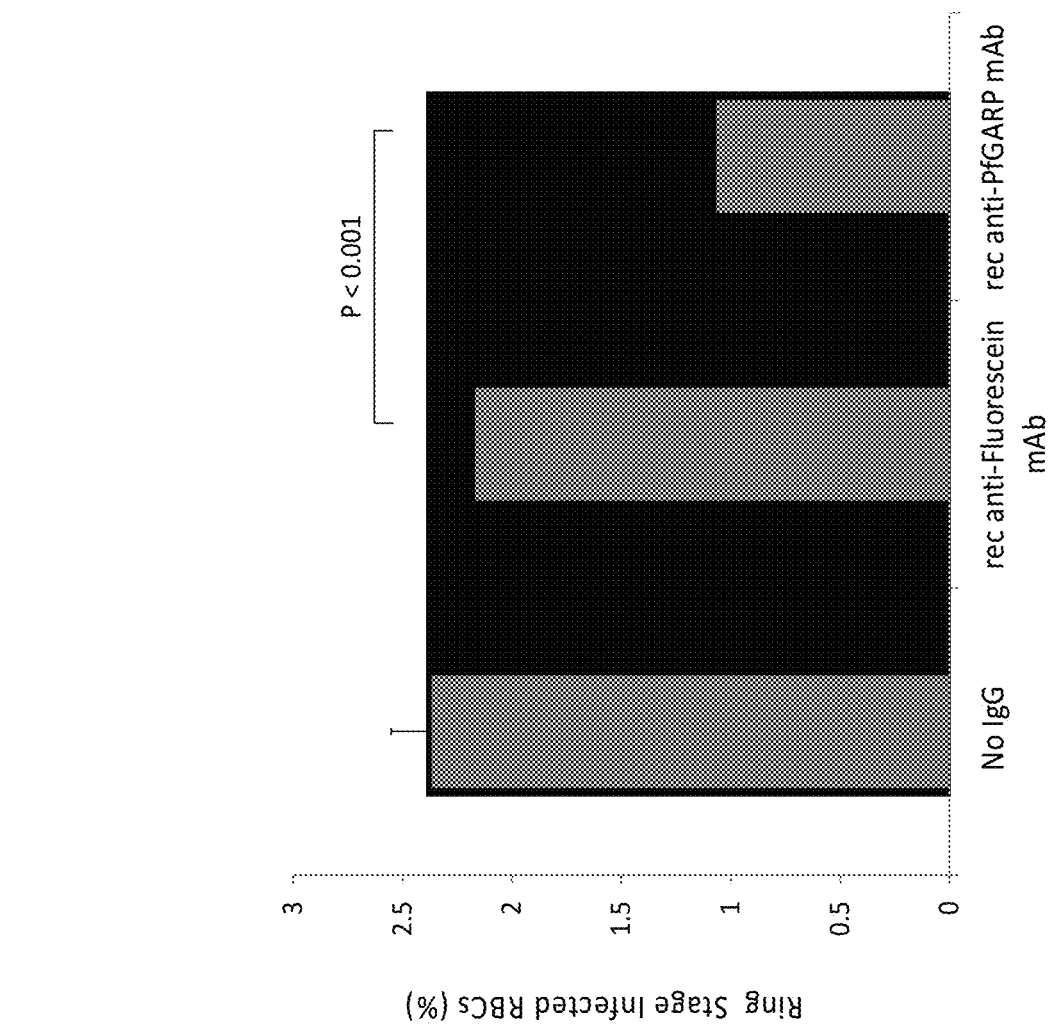
FIGS. 1A-1F are bar graphs showing that antibodies to PfGARP inhibit parasite growth. Polyclonal anti-PfGARP antibodies were generated by DNA vaccination in mice (FIGS. 1A, 1B and 1C) or anti-rPfGARP IgG purified from human sera collected in malaria endemic regions (FIGS. 1D-1F) inhibited parasite growth by 94-99% in 3 parasite strains in vitro. Ring stage 3D7 (FIGS. 1A and 1D), Dd2 (FIGS. 1B and 1E) and D10 (FIGS. 1C and 1F) parasites were cultured in the presence of anti-PfGARP mouse sera at 1:10 dilution, (FIGS. 1A, 1B and 1C) or anti-PfGARP IgG purified from human sera at 100 μg/ml (FIGS. 1D, 1E and 1F). Negative controls included no anti-sera and pre-immune mouse sera (FIGS. 1A, 1B and 1C), and control media and human IgG purified from human sera obtained from malaria naive individuals (FIGS. 1D, 1E and 1F).
FIG. 1H is a graph showing that anti-PfGARP antibodies kill *P. falciparum* parasites. *P. falciparum* 3D7 parasites were synchronized to the ring stage and plated at 0.08% parasitemia in the presence of anti-PfGARP-A polyclonal mouse sera (1:10 dilution) or pre-immune sera (1:10 dilution) or no sera. Media was changed daily and parasitemia was measured daily by microscopy. Moreover.
FIG. 1I is an image showing the gating strategy for FIG. 1J-iRBCs are identified in the dot plot as the population staining with both anti-Glycophorin A and Hoechst 33342. By 24 hours after the addition of anti-PfGARP antisera, 100% of the parasites showed disruption of their mitochondrial membrane potential, consistent with parasite death.
FIG. 1J are images showing the ring stage *P. falciparum* iRBCs that were incubated with pre-immune sera or anti-PfGARP polyclonal sera at 1:10 dilution or chloroquine (100 nM) as positive control at 37° C. for 12 and 24 hours. Contour plots demonstrating iRBCs with live parasites in the upper gate and dying/dead parasites in the lower gate defined by JC1 staining.
Figure 2A:
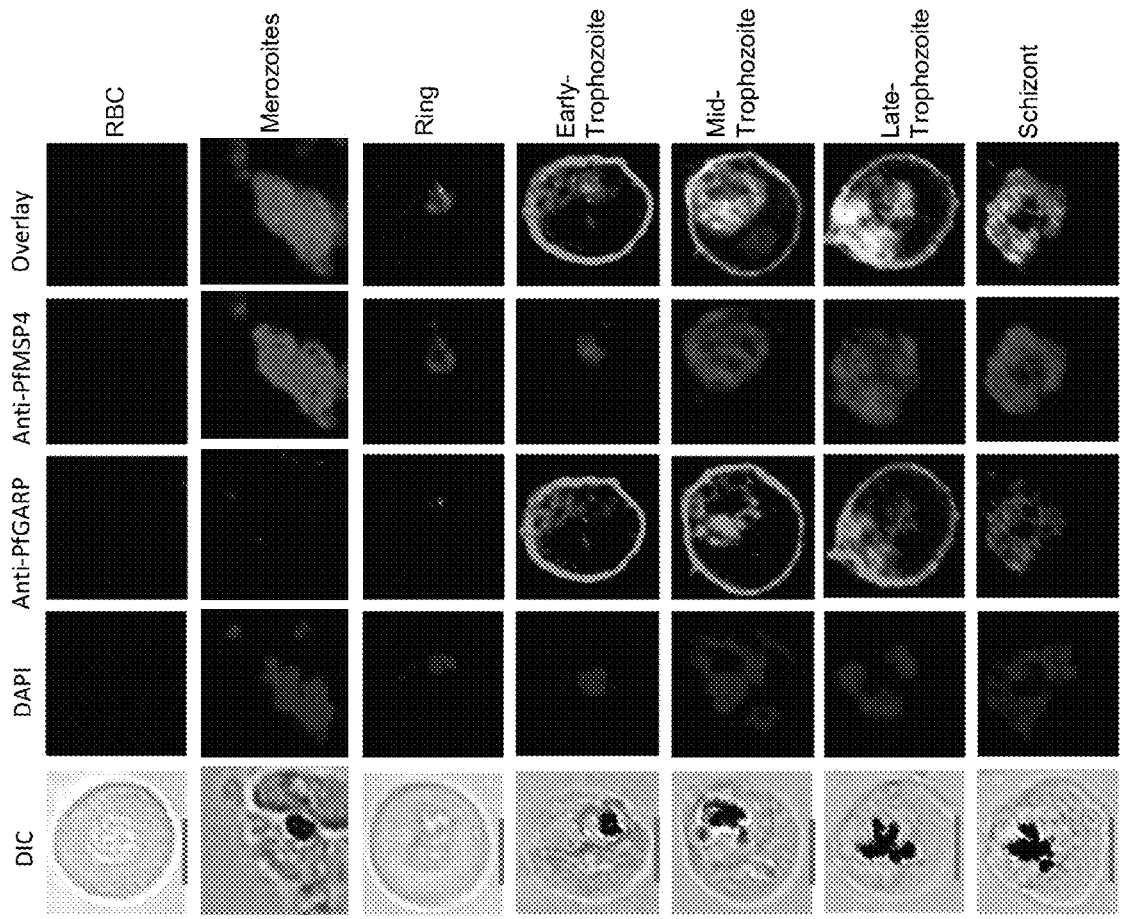
FIGS. 2A-2D are images showing that PfGARP localizes to the exofacial surface of trophozoite infected RBCs.
Figure 2B:
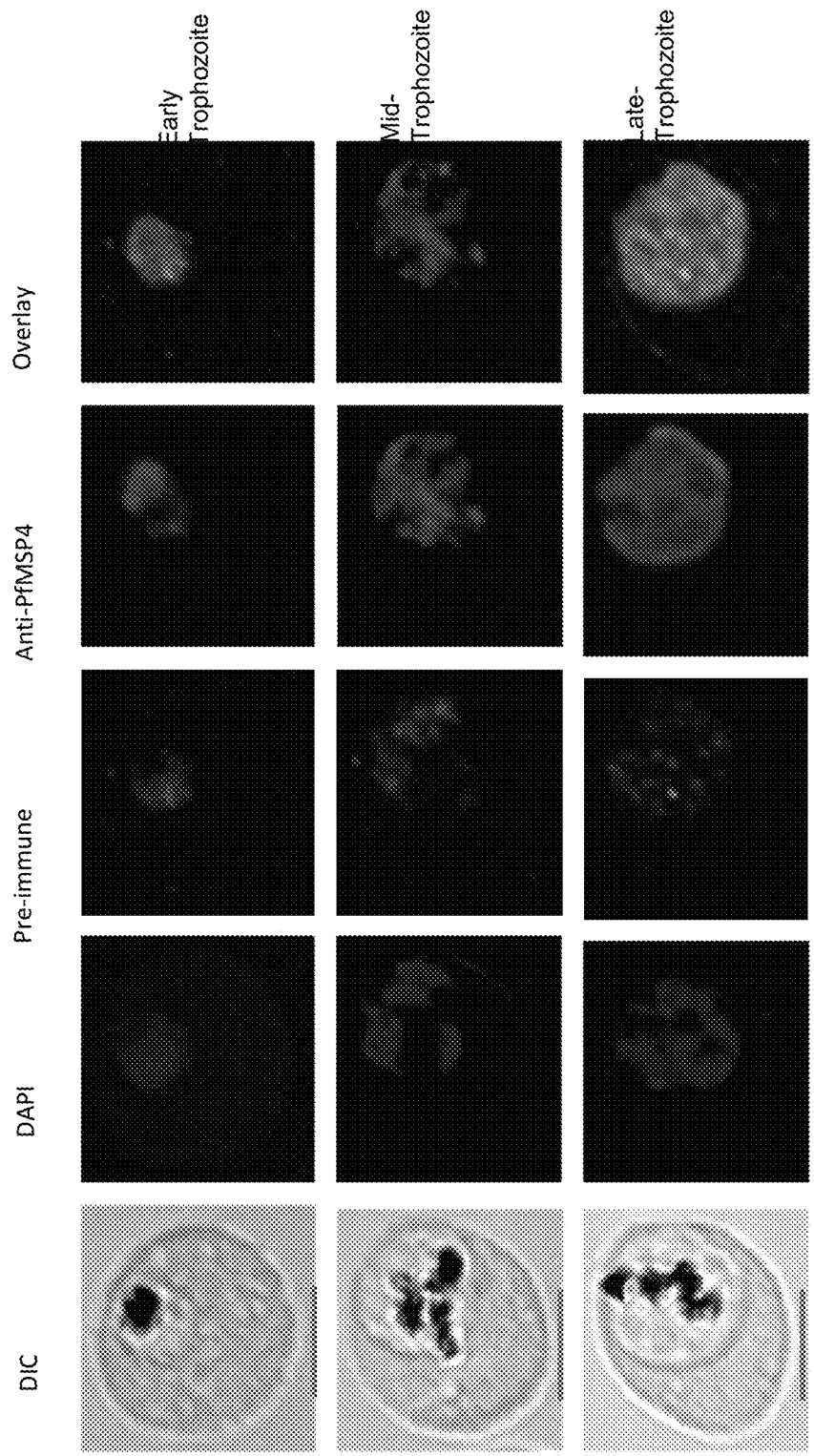
Figure 2D:
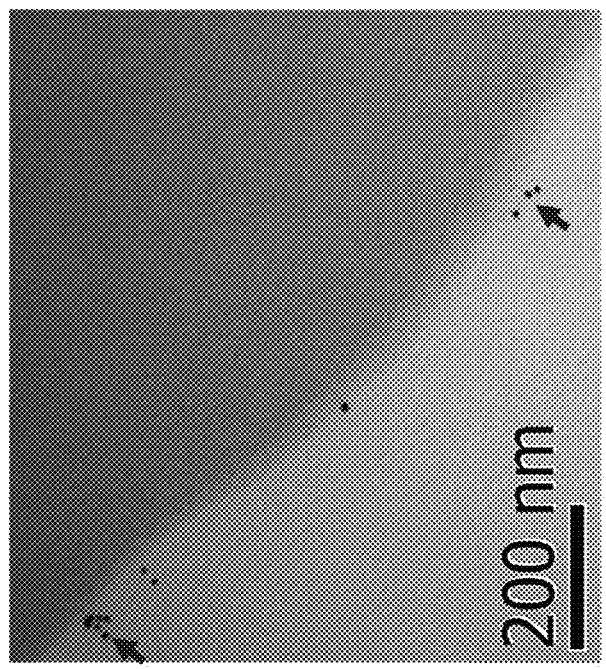
Figure 2C:
Figure 9B:
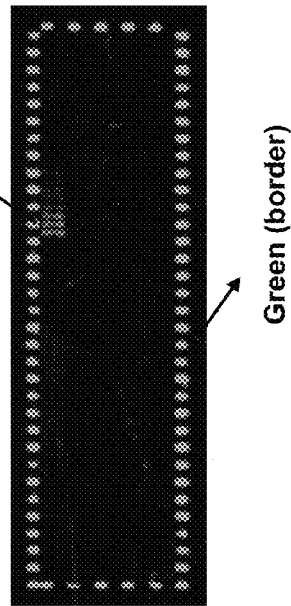
FIGS. 9A-9E are images showing that recombinant monoclonal anti-PfGARP (rec mAb7899) binds to PfGARP-A with a $K_d$ of 2.9 nM and inhibits parasite growth.
Figure 9C:
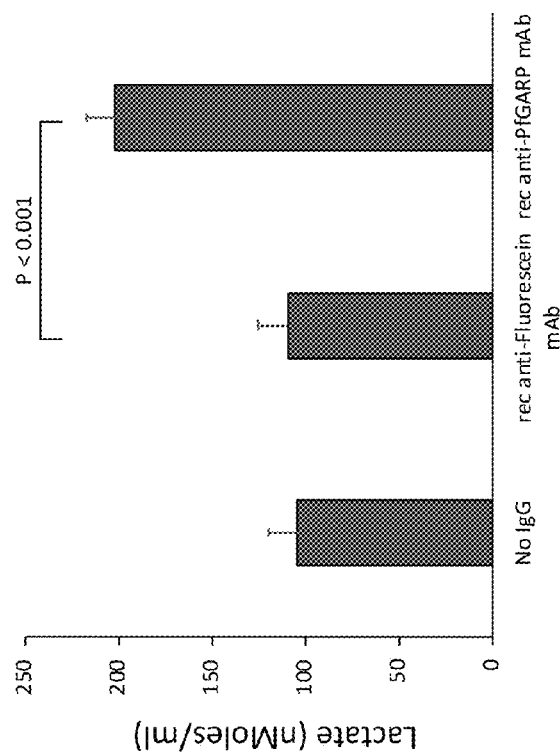
Figure 9A:
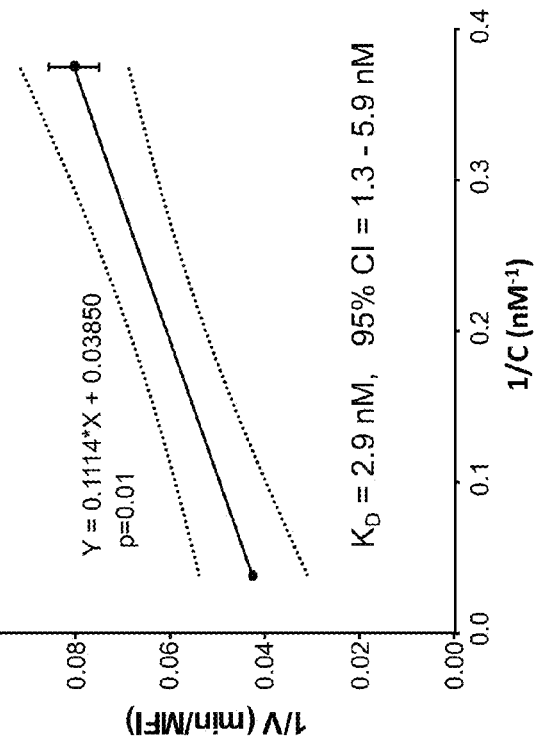
Figure 9D:
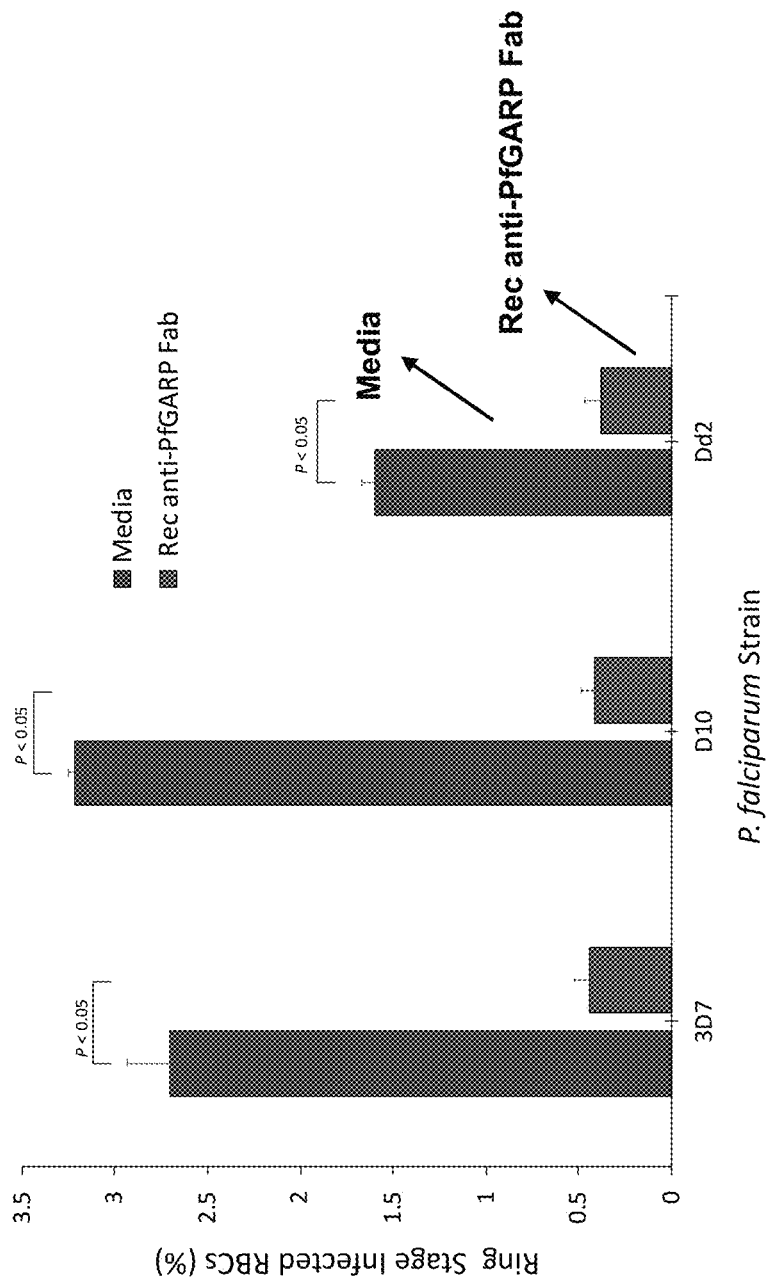

A series of monoclonal antibodies were produced in mice immunized with recombinant PfGARP-A. Sixteen mAbs reacted with PfGARP-A in ELISA based assays. mAb7899 killed parasites in culture (FIG. 1J). The variable regions of the immunoglobulin heavy and light chains of mAb7899 were sequenced and expressed and purified the recombinant mAh from transfected HEK293 cells. The recombinant mAh had a $K_D$ of 2.9 nM (95% CI=1.3-5.9 nM, FIG. 9A), inhibited parasite growth by 51% at a concentration of 250 µg/ml in GIA assays (FIG. 1K), and recognized aa 443-459 (VKNVIEDEDKDGVEIIN) (SEQ ID NO: 9) of full length PfGARP in microarray studies using multiple 15-mer overlapping peptides spanning PfGARP-A (FIGS. 9A-9C). Consistent with the loss of mitochondrial function, lactate levels in media from recombinant mAb7899-treated cultures were significantly higher than in media from cultures treated with a control recombinant monoclonal with specificity for fluorescein (FIG. 9C). Recombinant mAb7899 was produced as a monovalent Fab fragment which inhibited parasite growth by 76-87% across 3 parasite strains when used at 1 mg/mL in GIA assays (FIG. 9D). Surprisingly, this parasiticidal effect of this Fab fragment occurred in the absence of complement, cellular effector function, or antigen cross-linking.

Figure 10A:
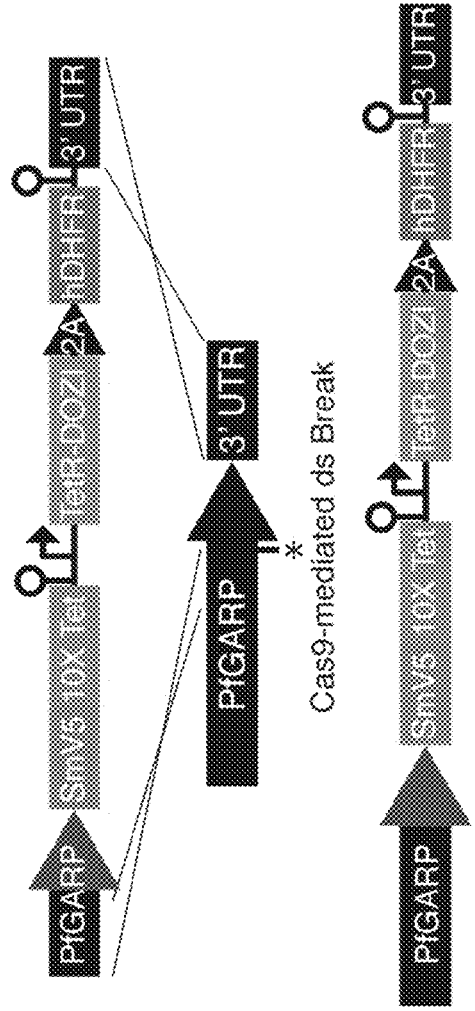
FIGS. 10A-10F are images showing the construction and characterization of PfGARP knock down parasite line.
Figure 10B:
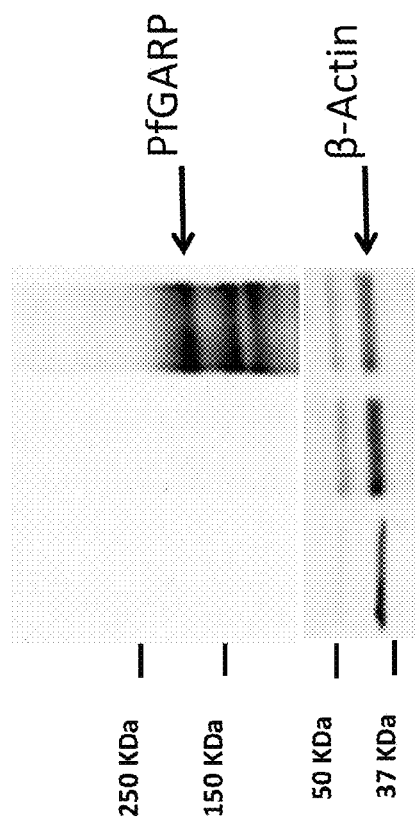
Figure 10C:
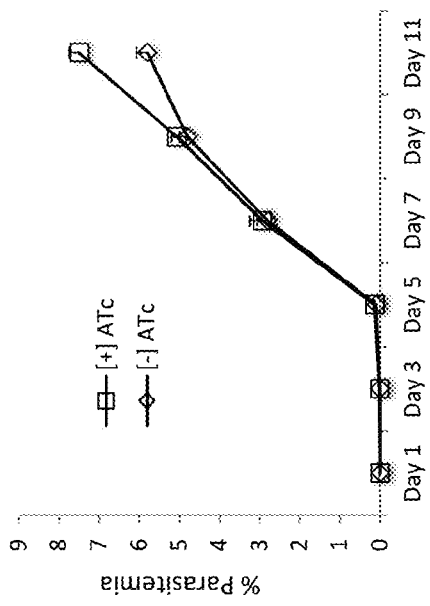
Figure 10E:
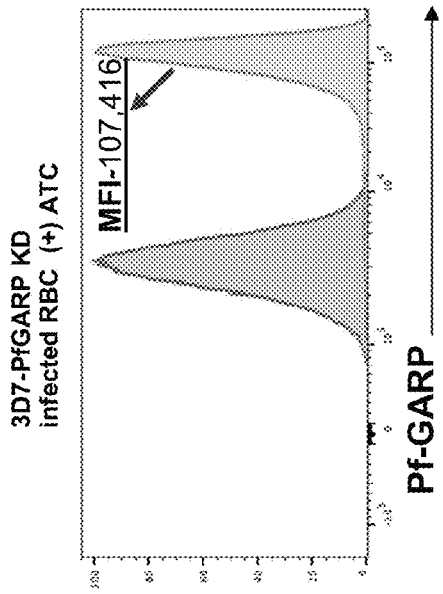
Figure 10D:
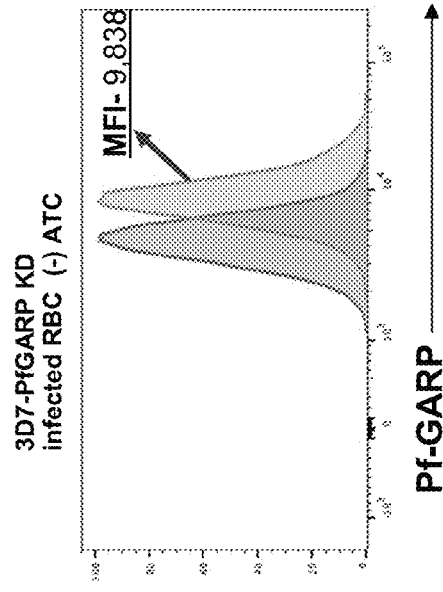
Figure 10F:
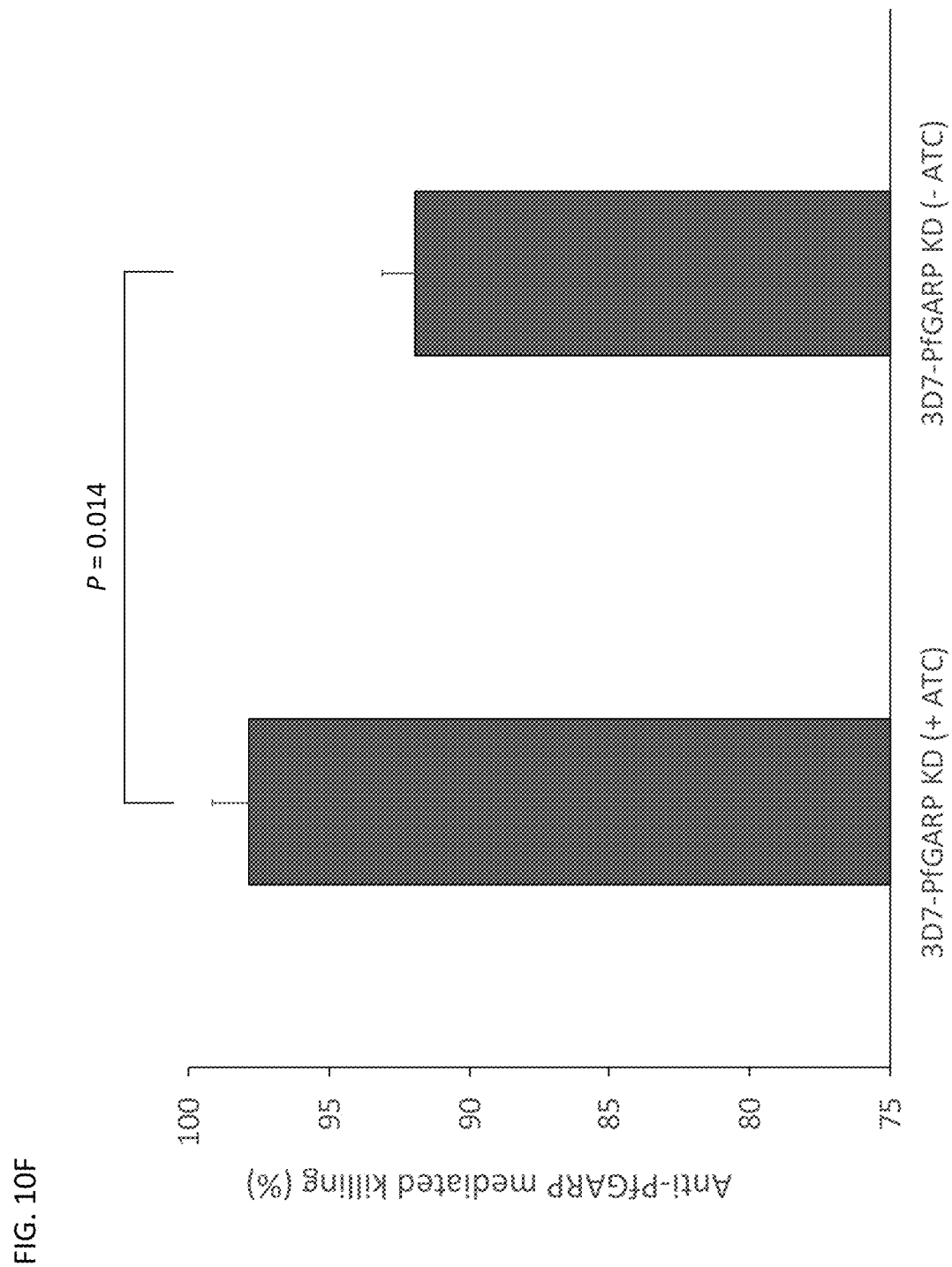

Parasites were constructed with a conditional knock-down of PfGARP using the TetR system 11 (FIG. 10A). Concordant with a recent genome-wide insertional mutagenesis screen, 3D7-PfGARP KD parasites, grown in the absence of the inducer anhydrotetracycline (ATc), did not display an overt growth phenotype in in vitro culture (Ganesan, S. M., et al. *Nature communications* 7, 10727 (2016)) despite a reduction in PfGARP protein levels of up to 90% (FIGS. 10B-10E). In GIA assays, the killing efficacy of anti-PfGARP antibodies was modestly reduced in 3D7-PfGARP KD parasites cultured without ATc compared to 3D7-PfGARP KD parasites cultured with ATc (P=0.014, FIG. 10F)). Anti-PfGARP mediated killing of 3D7-PfGARP KD parasites cultured without ATc may be due to residual expression of PfGARP even in the absence of the inducer.

Figure 9E:
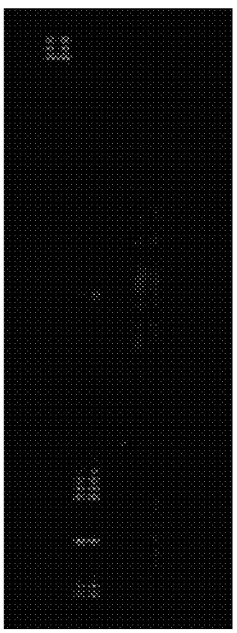

In GIA assays, mAb7899 is less potent at killing parasites than the polyclonal, monospecific anti-PfGARP-A. The monospecific polyclonal anti-PfGARP-A may recognize a different set of epitopes within PfGARP-A compared to mAb7899. In epitope mapping studies, polyclonal anti-PfGARP-A did not recognize the binding site for mAb7899 (aa 443-459). Instead, polyclonal anti-PfGARP-A recognized 3 distinct epitopes (#1 aa 464-478), (#2 aa 480-492), and (#3 aa 504-522) (FIG. 9E).

Mice were immunized with epitope #1 or #2 to generate epitope-specific antibodies and both these antisera kill trophozoites in GIA assays. Affinity purified anti-epitope #1 had an $IC_{50}$ for parasite killing comparable to the $IC_{50}$ for the polyclonal anti-PfGARP-A antisera (FIG. 9H). Parasites were constructed with a conditional knock-down of PfGARP using the TetR system (Ganesan, S. M., et al. *Nature communications* 7, 10727 (2016)) (FIG. 10A and Table 3). Concordant with a recent genome-wide insertional mutagenesis screen, 3D7-PfGARP KD parasites, grown in the absence of the inducer anhydrotetracycline (ATc), did not display an overt growth phenotype in in vitro culture (Zhang, M. et al. *Science* 360 (2018)) despite a reduction in PfGARP protein levels of up to 90% (FIG. 10B-10E). In GIA assays, the killing efficacy of anti-PfGARP antibodies was modestly reduced in 3D7-PfGARP KD parasites cultured without ATc compared to 3D7-PfGARP KD parasites cultured with ATc (P=0.014, FIG. 10F)). Anti-PfGARP mediated killing of 3D7-PfGARP KD parasites cultured without ATc may be due to residual expression of PfGARP even in the absence of the inducer. To test this hypothesis, PfGARP deleted parasites (3D7-PfGARP-KO) were constructed and evaluated in growth and GIA assays. 3D7-PfGARP-KO did not display an overt growth phenotype in in vitro culture and the killing efficacy of anti-PfGARP antibodies was markedly reduced compared to wild-type 3D7 parasites.

TABLE 3

Primers used in construction of PfGARP KD parasite

| Oligo Number | Sequence |
|---|---|
| oJDD1027 | gtacgcggccgcCCAAGTCCATTGACAGACG |
| oJDD4507 | CTTgTGgTTgTCcCTcCTaGGgACaACgTTgACtCGaCCaAtGTACCTATTAATTGCTCTTGTATGGATAAG |
| oJDD2933 | CTGCTGCTGAGTACTATCAAGTC |
| oJDD4279 | CTACTTTGTTCTGATCATATG |
| oJDD4280 | TTCTTTTTTGGGGGGCTTTCATG |
| oJDD3560 | GAACTTAAGGGAATTGATTTCAAGG |
| oJDD44 | TGGGGTGATGATAAAATGAAAG |
| oJDD3541 | aattccctaggaatcgatacgtacgctgcagc |
| oJDD3542 | aattgctgcagcgtacgtatcgattcctaggg |
| oJDD3481 | CGAATAAAttaattaagtttaaacATGTCTAGATTAGATAAAAGTAAAGTGATTAACAG |

TABLE 3-continued

Primers used in construction of PfGARP KD parasite

| Oligo Number | Sequence |
|---|---|
| oJDD3253 | ACCACATGTTAATAATGATCCTCTACCTTCACCGCTAGCGGTATATAAGGATGGGTC |
| oJDD3480 | ctgatccttaagCGGAAAGGGGCCATTGGATATATATTTAG |
| oJDD3482 | CTAATCTAGACATgtttaaacttaattaaTTTATTCGAAATGTGGGAAGAAAAAAAATATAAT |
| oJDD3254 | GACCCATCCTTATATACCGCTAGCGGTGAAGGTAGAGGATCATTATTAACATGTGGT |
| oJDD3483 | gacatgcctagggaattcAATTCTAGATTTAATAAATATGTTC |
| oJDD3484 | ctagtcccatggATGGGAAAACCTATACCGAACCCCCTC |
| oJDD3485 | gactaggggcccTTAGGTACTATCCAGTCCCAGCAAC |
| oJDD4506 | CaATtGGtCGaGTcAAcGTtGTcCCtAGgAGgGAcAAcCAcAAGAAGAAAATGGCAAAAATAGAAGAAGCAG |
| oJDD3566 | tgcatgccatggTATTTTTGCATTTTTTCTTAAATTTC |
| oJDD3563 | CAAAAAAGAAAAAATCTTAgatatcCCAAGTCCATTGACAGACGTAACTACACCAG |
| oJDD4507 | CTTgTGgTTgTCcCTcCTaGGgACaACgTTgACtCGaCCaATtGTACCTATTAATTGCTCTTGTATGGATAAG |
| oJDD3561 | catgcagcggccgcTGTCCTGTTTTATTTGTAATGTTTTATTTG |
| oJDD3562 | TCTGTCAATGGACTTGGgatatcTAAGATTTTTTCTTTTTTGGGGGCTTTC |
| oJDD2959 | ACATCATCGGACTTTTCTTCTTCAGGGTAGGAGTATTCTATAGTGTCACCTAAATAGCTTG |
| oJDD2960 | TCATTATATATAAGAACATATTTATTAAATCATATCGATAACTCCATGGAACTCCTAGGC |
| oJDD2961 | GCCTAGGAGTTCCATGGAGTTATCGATATGATTTAATAAATATGTTCTTATATATAATGAGAAATAAATATT |
| oJDD2962 | CCCCCGGggcggccgctctagaattctcgaGTTTATTCGAAATGTGGGAAGAAAAAAAAT |
| oJDD2963 | AATAAACtcgagaattctagagcggccgccCCGGGGGTACCCTGCAGGTCGACTTAATTA |
| oJDD2964 | AAGCTATTTAGGTGACACTATAGAATACTCCTACCCTGAAGAAGAAAAGTCCGATGATGTTG |
| oJDD3036 | cggaattcGGATTTCTACACATCTTGAGGTTTTACAATAATATCTTCTTTTTTTT |
| oJDD3037 | AAAACagGTCTTCtcGAAGACccAATATTATATACTTAATATGAAATATGTGCATATAGGAAAAATTATGCATTTTGG |
| oJDD3038 | ATATTggGTCTTCgaGAAGACctGTTTTAGAGCTAGAAATAGCAAGTTAAAATAAGGCTAGTCC |
| oJDD2789 | AGGCGATTAAGTTGGGTAACGCCAG |
| oJDD3039 | ATAAGAATgcggccgcTCTATATTTGTTAAATTAAGACCAAACTTAGTACCTTAATGA |
| oJDD3040 | ATAGTTTAgcggccgcTACTTTCACTAATATAGGTCCTATCATAACTAACATAGGA |
| oJDD3058 | TTATATATAAGAACATATTTATTAAATCTAgaattcGGATTTCTACACATCTTGAGGTTT |
| oJDD4088 | GCTCTAAAACtaggacgtgttaatgtagtacAATATTATATACTTAATATGAAATATG |
| oJDD3059 | GTAAGGAGAAAATACCGCATCAGGCGCCAGCCTAGGTTTATGGTAGCCTTAAAAACTTCA |
| oJDD4089 | TATAATATTgtactacattaacacgtcctaGTTTTAGAGCTAGAAATAGCAAGTTAA |
| 3HA-MCS | GGCCGCTAGCCATGGGGATCCTACCCTTACGATGTTCCTGACTATGCGGGCTATCCCTATGACGTCCCGGACTATGCCGAGTACCCTTACGATGTTCCTGACTATGCGTAGGGGCCCTAACCCGGGATAGTCGACAAGCTTGGTACAAGAAGAAAATGGCAAAAATAGAAGAAGCAGAATTACAAAAACAAAAACATGTTGATAAAGAAGAAGATAAAAAAGAAGAAAGTAAAGAAGTTGAAGAAGAAAGTAAAGAAGTTCAAGAAGATGAAGAAGAAGTTGAAGAGGATGAAGAAGAGGAAGAGGAGGAAGAGGAAGAAGAGGAGGAAGAAGAGGAAGAAGAGGAAGATGAAGTAGAAGAAGATGAAGATGATGCAGAAGAAGACGAAGATGATGCTGAGGAAGATGAAGATGATGCAGAAGAAGACGATGATGATGCFGAAGAAGATGATGATGATGCTGAAGAAGATGATGAAGATGAGGATGAAGATGAAGAAGAAGA |

TABLE 3-continued

Primers used in construction of PfGARP KD parasite

| Oligo Number | Sequence |
|---|---|
| caPfGARP | AGAAGATGAGGAAGAAGAAGAGGAGAGTGAAAAGAAAATAAAAAGAAATTTAAGAAAAAATGCAAAAATA |

Example 2: Stage-Specific Immunolocalization of PfGARP

Figures 12A, 12B:
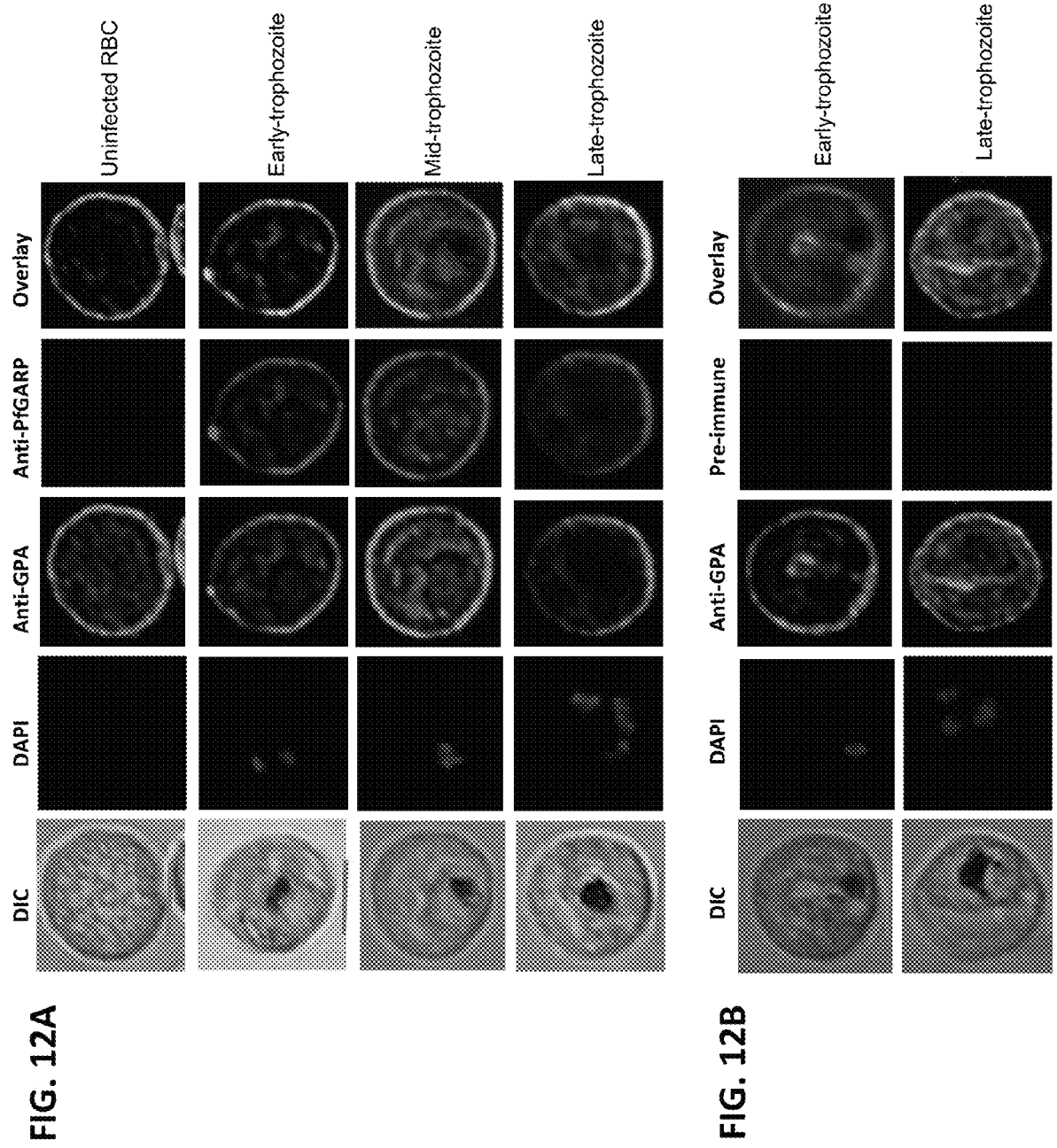
FIGS. 12A and 12B are images showing that PfGARP co-localizes with glycophorin A to the exofacial surface of trophozoite infected RBC membranes.
Figure 13:
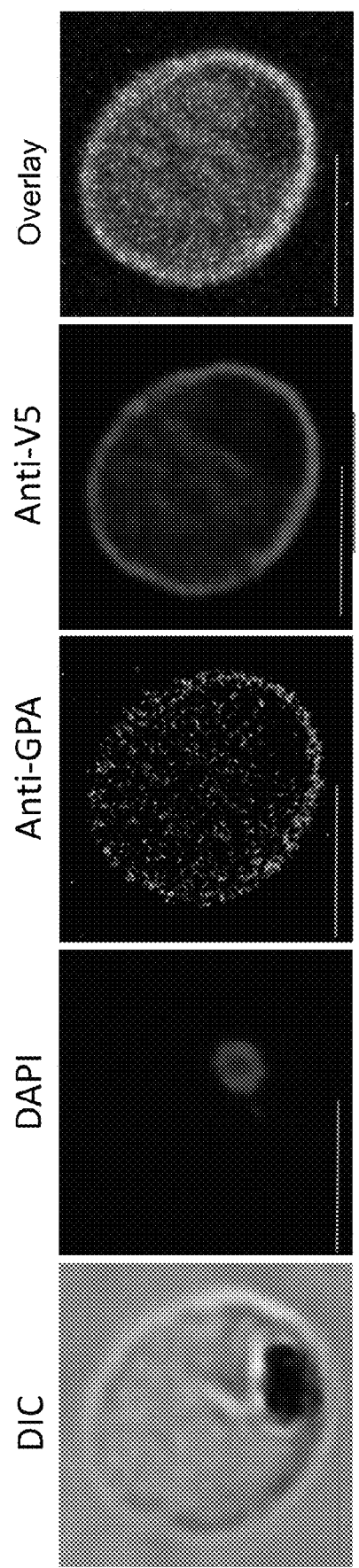
FIG. 13 are images showing that PfGARP and glycophorin A both localized to the exofacial surface of trophozoite infected RBC membranes. PfGARP-KD parasite infected RBCs at the trophozoite stage were probed with rabbit anti-glycophorin A (green) and anti-V5 mouse antibodies (red) and counterstained with 4',6-diamidino-2-phenylindole (DAPI) to label parasite nuclei. PfGARP tagged with the V5 epitope co-localizes with glycophorin A to the exofacial surface of trophozoite-infected, non-permeabilized, RBCs. The purpose was to demonstrate that PfGARP localizes to the external surface of trophozoite infected RBCs using both a PfGARP specific as well as a commercially available tag-specific antibody using the same permeabilization, fixation, staining protocol. Our PfGARP-KD parasite carries a C-terminal V5 tag. When grown in the presence of the inducer (ATc), they express normal amounts of PfGARP with this tag, thus the choice of this parasite for the anti-V5 IFAs.
Figure 15B:
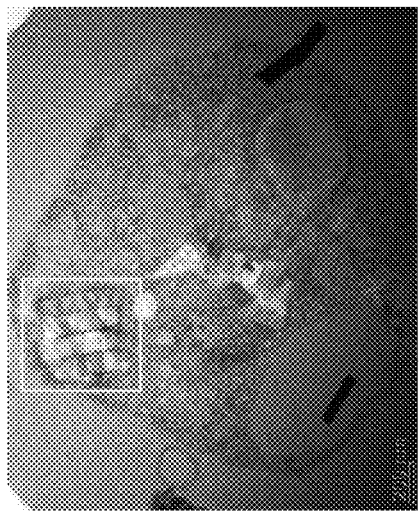
FIGS. 15A-15D are images showing that anti-PfGARP antibodies alter food vacuole integrity. 3D7 parasites were synchronized to the ring stage and plated at 5% parasitemia in the presence of pre-immune (FIG. 15A) and anti-rPfG-ARP-A mouse sera (FIG. 15B) at 1:10 dilution. Parasites were cultured for 24 hours and processed for transmission electron microscopy.
Figure 15D:
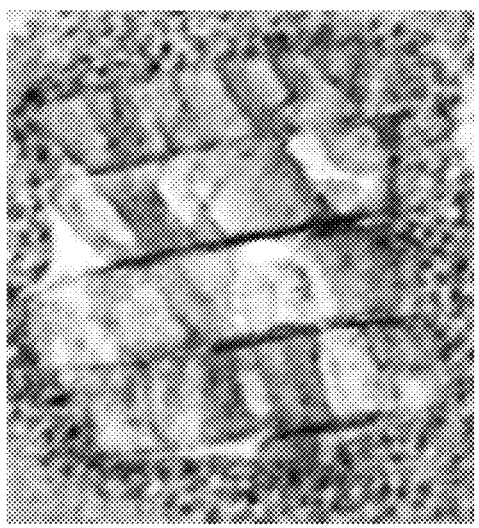
Figure 15A:
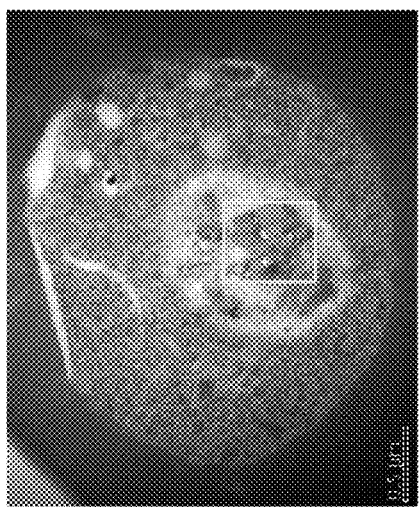
Figure 15C:
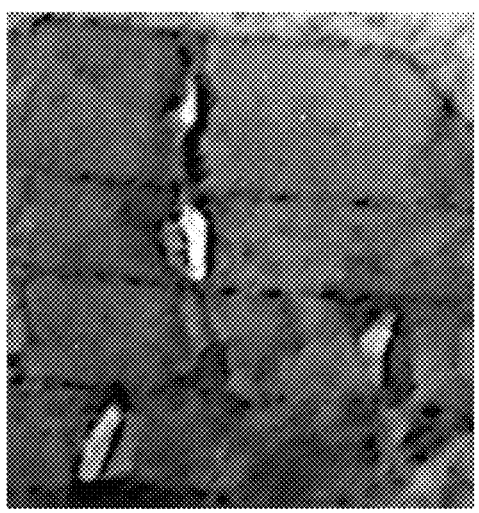

PfGARP was immunolocalized by immunofluorescence confocal microscopy and immunogold transmission electron microscopy (FIGS. 2A-2D). Anti-PfGARP did not bind to free merozoites, rings or schizonts, but did specifically recognize an antigen expressed on the RBC membrane in early to late trophozoite-infected RBCs (FIGS. 2A, 2B and 11A-11E). In dual color immunofluorescence studies using non-permeabilized samples, PfGARP localized with glycophorin A to the surface of trophozoite-infected RBCs using anti-PfGARP in 3D7 parasites (FIGS. 12A-12B). Similar results were obtained when PfGARP KD parasites, in which PfGARP has a C-terminal V5 tag, were cultured in the presence of anhydrotetracycline (ATC) and probed with anti-V5 (FIG. 13). Accessibility of PfGARP to antibodies in living parasites was further evaluated by immunoelectron microscopy.

Non-permeabilized, non-fixed *P. falciparum* infected RBCs was probed with anti-PfGARP antibodies. PfGARP was confined to the exofacial leaflet of the RBC membrane in early trophozoite infected RBCs (FIGS. 2C and 2D) and did not appear to co-localize with knob structures (FIG. 14). This pattern of staining was observed in essentially all of the early trophozoite-infected RBCs examined (n>100).

Example 3: Anti-PfGARP Disrupts Food Vacuole Integrity

Figure 16:
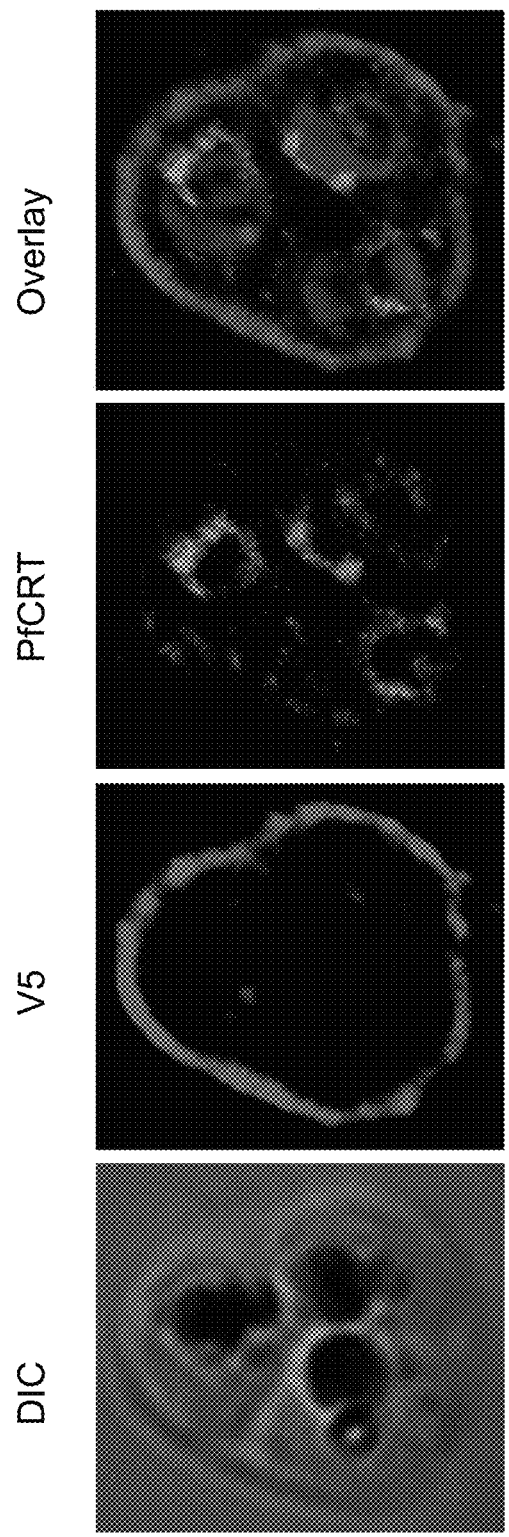
FIG. 16 are images showing that PfGARP does not co-localize with PfCRT to the food vacuole in the majority of trophozoite infected RBCs. 3D7-PfGARP-KD parasite infected RBCs at the trophozoite stage were probed with anti-PfCRT (green), anti-V5 antibodies (red) and counterstained with 4',6'-diamidino-2-phenylindole (DAPI) to label parasite nuclei. Scale bar is 5 µm. Data are representative of 3 independent experiments.

To evaluate the impact of treatment with anti-PfGARP antibodies on the ultrastructure of infected RBCs, ring stage parasites were treated with pre-immune or anti-PfGARP antisera for 24 hours prior to examination by transmission electron microscopy. Treatment with anti-PfGARP had a striking impact on the morphology of the food vacuole compared to parasites treated with pre-immune sera. Specifically, the food vacuole in anti-PfGARP9 treated parasites was markedly diminished in size and appeared condensed tightly around the hemozoin crystals (FIGS. 15A-15D). In many cases, the food vacuole appeared absent—a previously unreported and surprising effect of antimalarial antibodies. In these parasites, non-membrane bound hemozoin would potentially be exposed to the trophozoite cytoplasm. Free hemozoin has been described in parasites treated with high concentrations of chloroquine (3 μM) which disrupts the food vacuole membrane (Zhang, M. et al. *Science* 360 (2018)). In contrast, lower concentrations of chloroquine (68 nM) cause marked food vacuole swelling, but no extravasation of hemozoin into the cytoplasm (Ch'ng, J. H. et al. *Cell Death & Disease* 2, e216, (2011)). The possibility that PfGARP also localized to the food vacuole membrane by colocalization studies was explored with PfCRT. In the majority of infected RBCs, PfCRT and PfGARP did not co-localize (FIG. 16).

Figure 17:
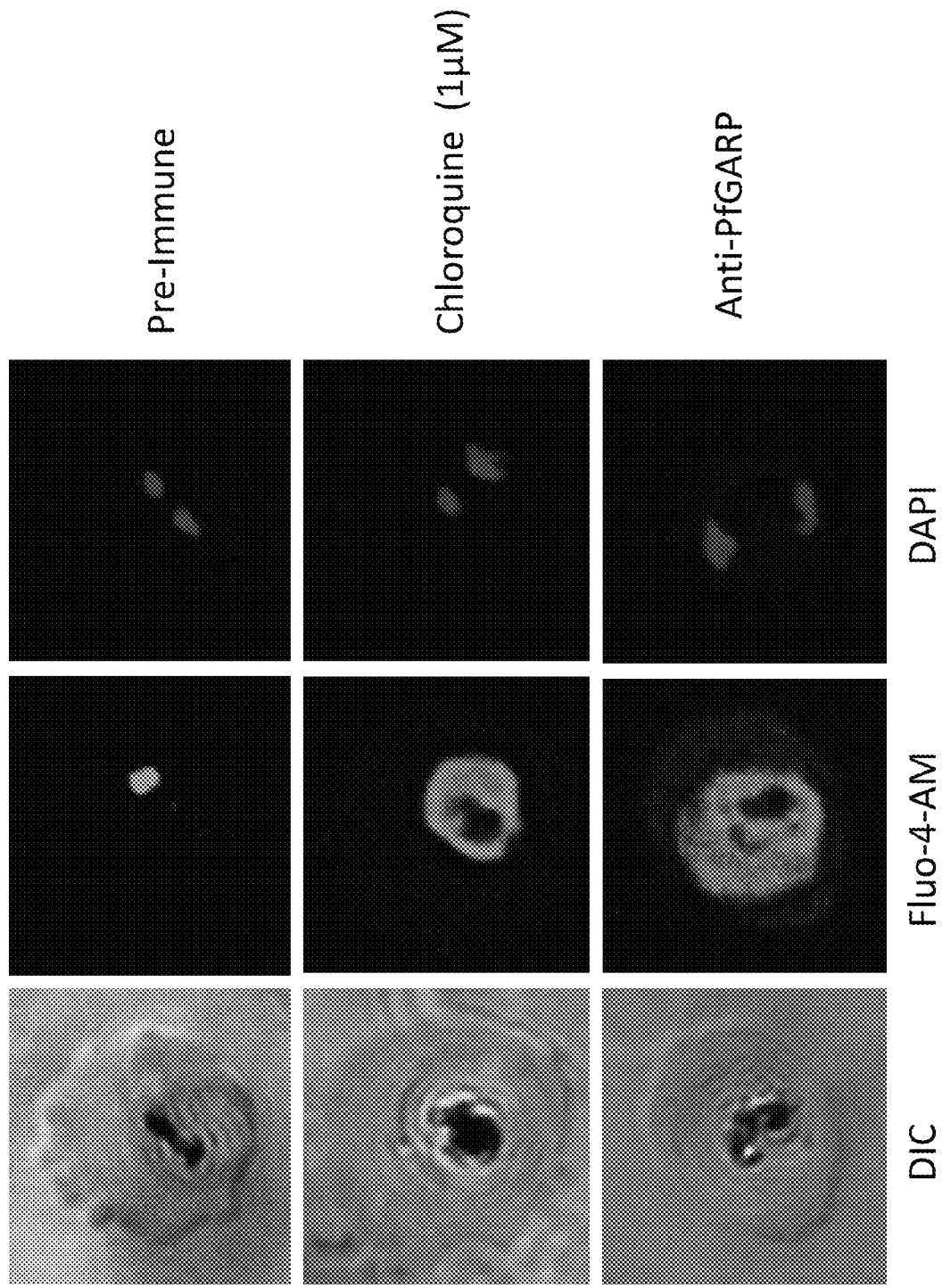
FIG. 17 are images showing that anti-PfGARP disrupts food vacuole integrity. Ring stage 3D7 parasites were treated with pre-immune sera (1:10), 1 µM chloroquine, or anti-PfGARP antisera (1:10) for 24 hours, followed by staining with DAPI and Fluo-4-AM. By 24 hours after the addition of anti-PfGARP antisera, 100% of the parasites showed disruption of their food vacuole as evidenced by dye localization studies. Data are representative of 2 independent experiments.
Figure 19A:
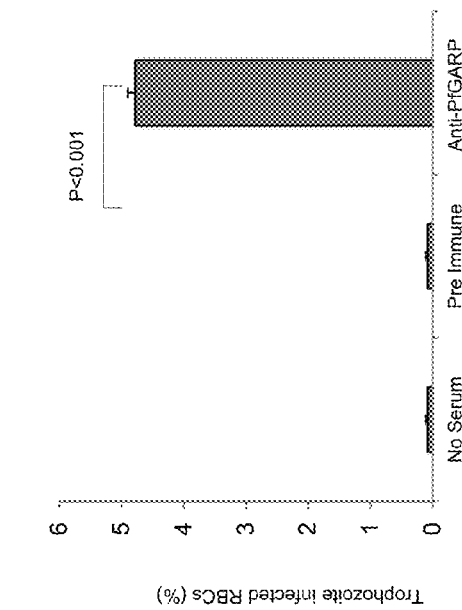
FIGS. 19A-19E are graphs showing anti-PfGARP arrests parasite development at the trophozoite stage.
Figure 19B:
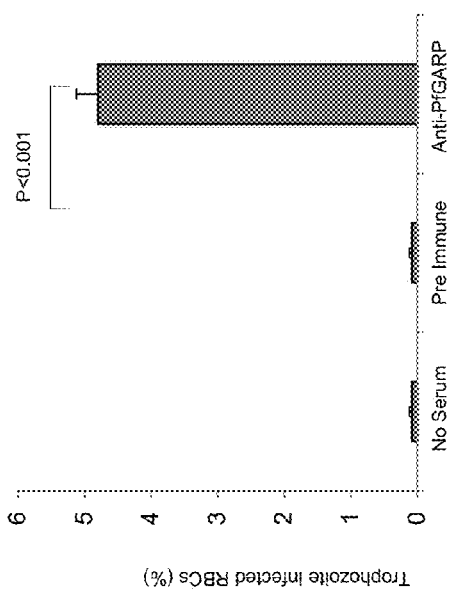
Figure 19C:
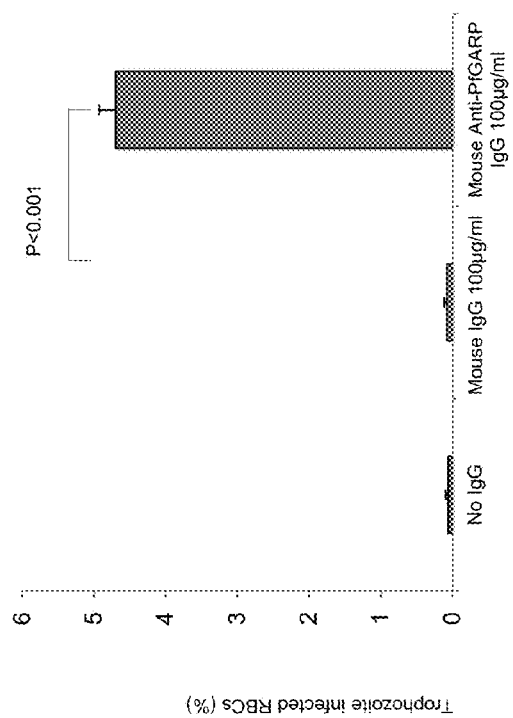
Figure 19D:
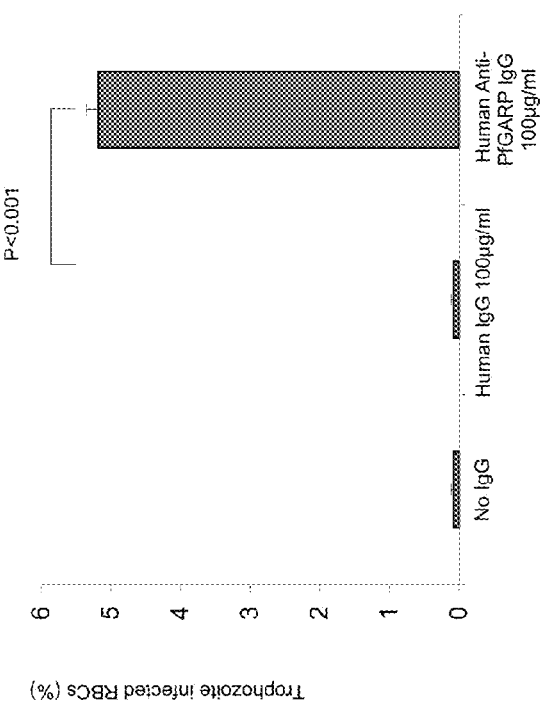
Figure 19E:
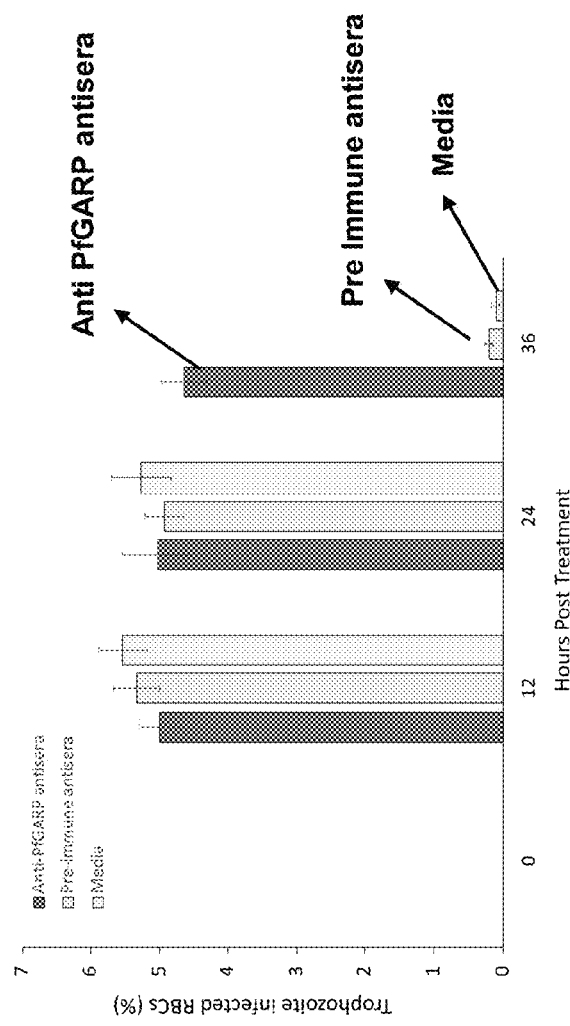
Figure 20B:
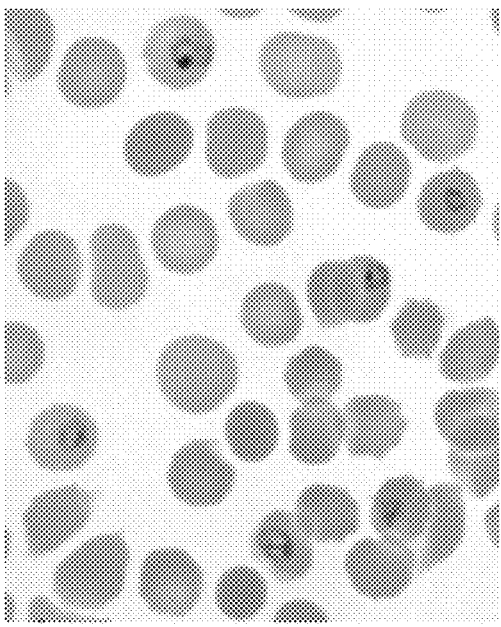
FIGS. 20A-20D are images showing that anti-PfGARP arrests parasite development at the trophozoite stage followed by parasite death. 3D7 parasites were synchronized to the ring stage and plated at 5% parasitemia in the presence of pre-immune (FIGS. 20A and 20C) and anti-rPfGARP-A mouse sera (FIGS. 20B and 20D) at 1:10 dilution. Parasites were cultured for 24 hours (FIGS. 20A and 20B) or 48 hours (FIGS. 20C and 20D), stained with giemsa, and photographed by light microscopy.
Figure 20D:
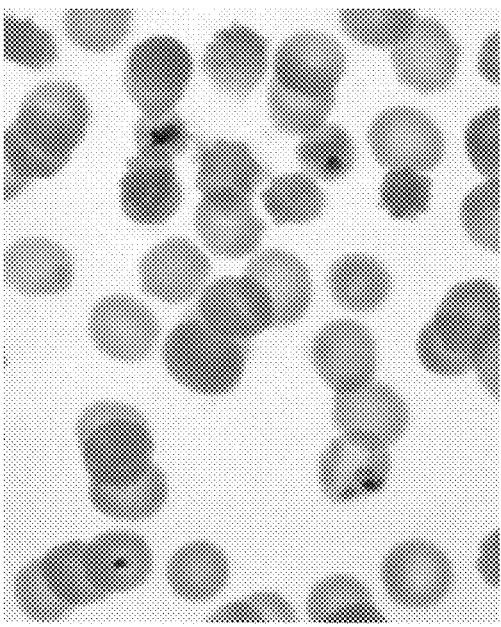
Figure 20A:
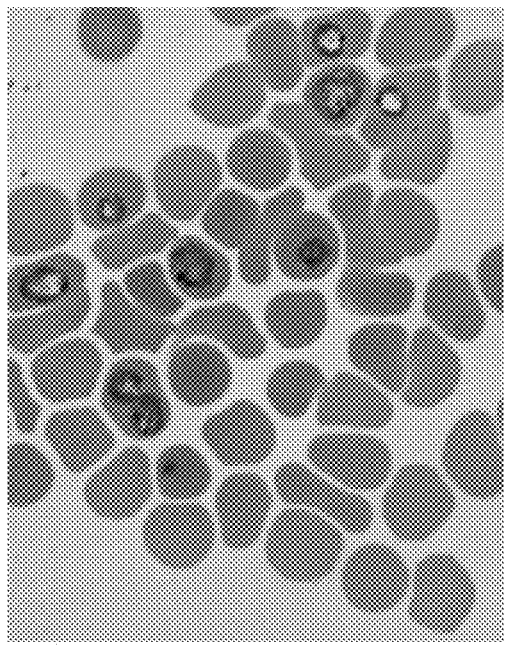
Figure 20C:
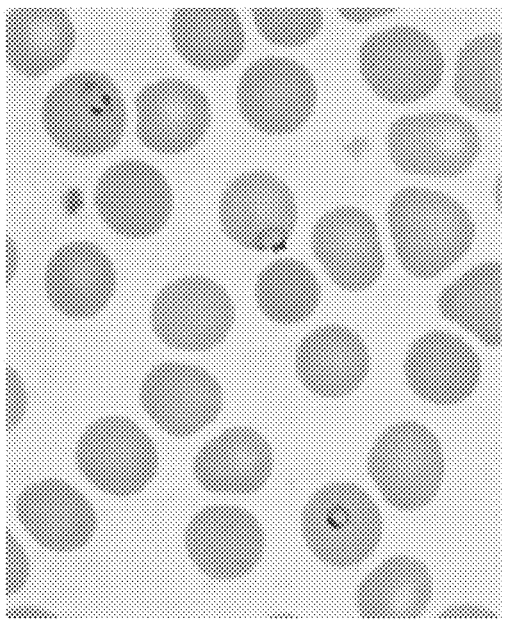

The impact of anti-PfGARP antibodies on food vacuole integrity by confocal microscopy was evaluated using the calcium binding dye Fluo-4-AM, which preferentially labels the food vacuole and has been used to distinguish the food vacuole from the endoplasmic reticulum (Zhang, M. et al. *Science* 360 (2018)). Ring-infected RBCs treated with anti-PfGARP antisera for 24 hours demonstrated marked loss of food vacuole integrity as evidenced by the redistribution of Fluo-4-AM (and therefor calcium) from the food vacuole to the parasite cytosol (FIG. 17).

Figure 23:
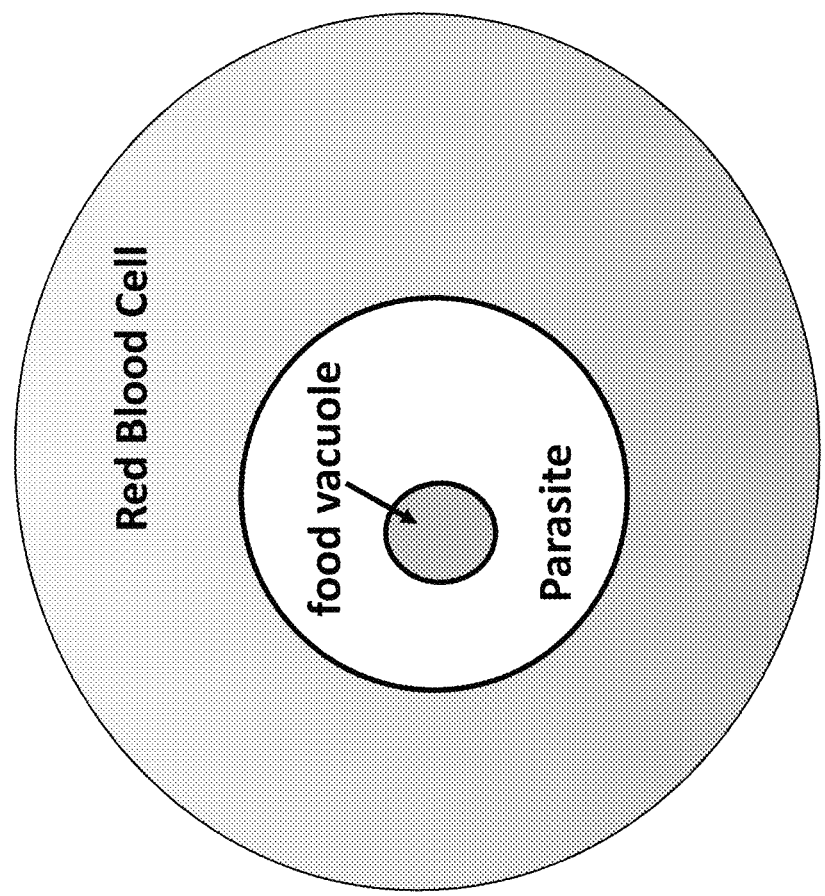
FIG. 23 is an image showing that anti-PfGARP treatment causes disruption of the food vacuole and dispersion of hemozoin. *P. falciparum* 3D7 parasites were synchronized to the ring stage and incubated with pre-immune mouse sera, or anti-PfGARP-A (1:10 dilution) for 30 hours and processed, embedded, and imaged for Serial Block Face-Scanning Electron Microscopy.
Figure 24B:
Figure 24A:
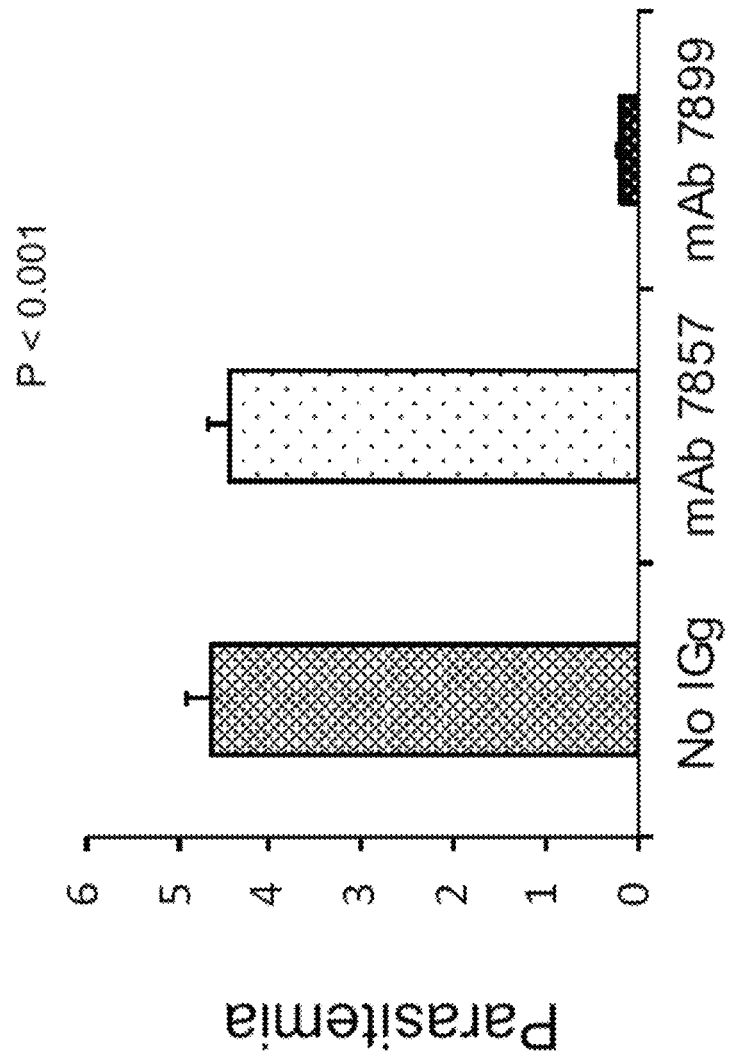

The impact of anti-PfGARP antibodies on food vacuole integrity was further confirmed and visualized by serial block face scanning electron microscopy (SBF-SEM). Ring stage parasites were incubated with pre-immune or anti-PfGARP antisera for 30 hours prior to examination by SBF-SEM. Three dimensional reconstruction demonstrated that treatment with anti-PfGARP resulted in the complete loss of food vacuole integrity with hemozoin dispersed broadly throughout the parasitophorous vacuole (FIG. 23).

Anti-PfGARP Antibodies Activate Parasite Programmed Cell Death

Figure 3A:
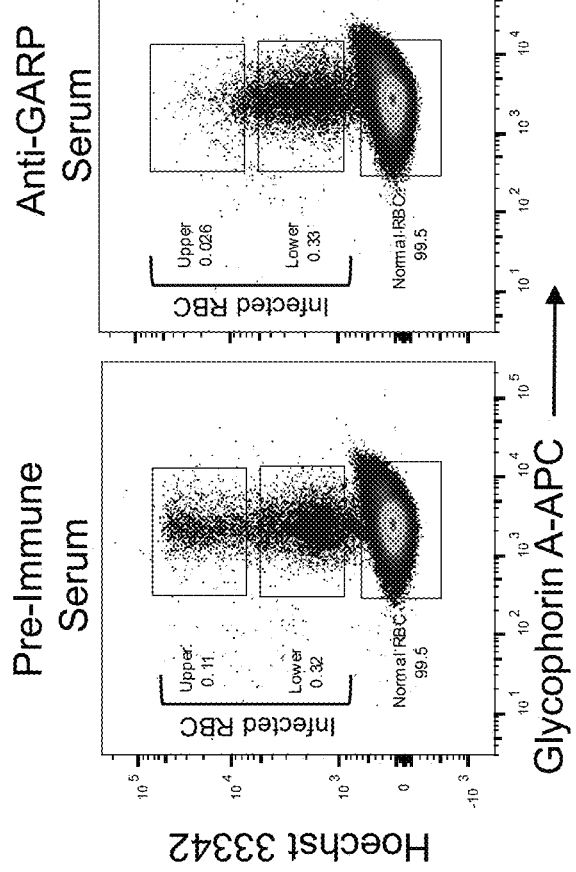
FIGS. 3A-3D are images showing that antibodies to PfGARP bound to *P. falciparum* infected RBCs leading to activation of caspase-like proteases and DNA fragmentation.
Figure 3B:
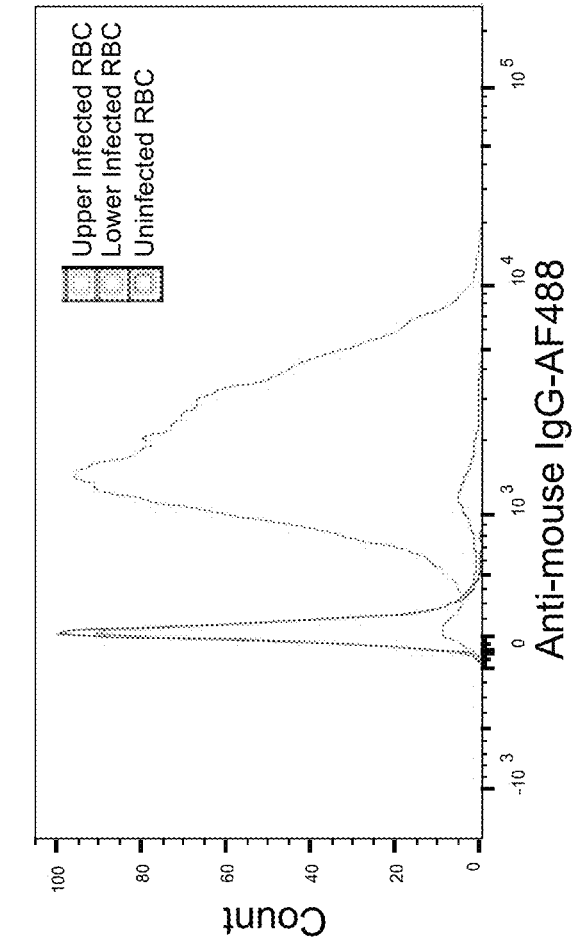
Figure 3D:
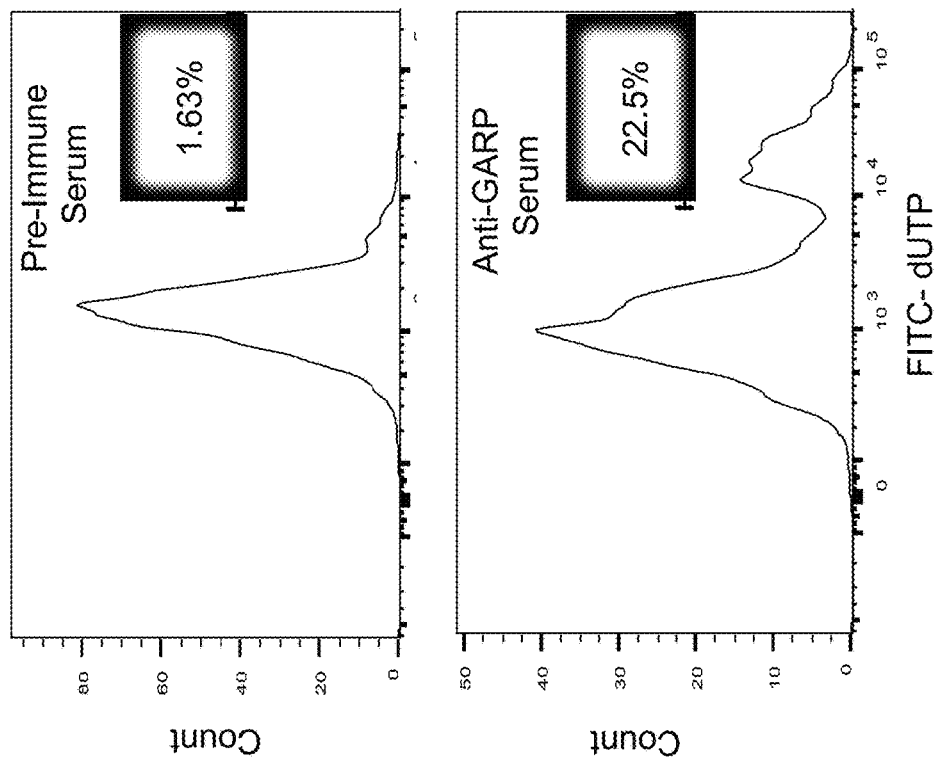
Figure 3C:
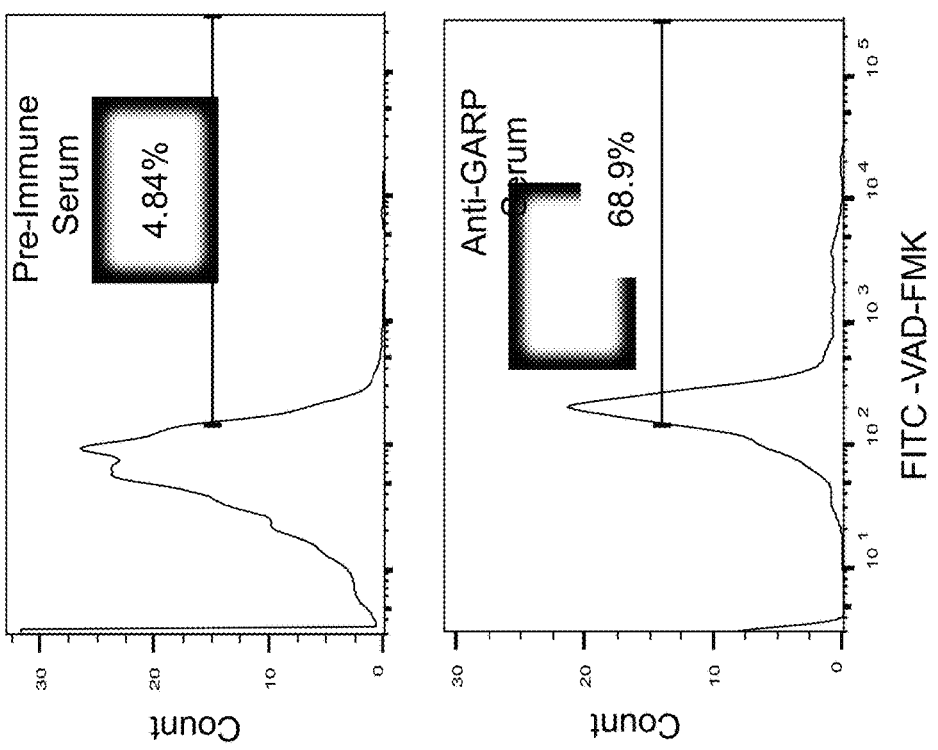

The impact anti-PfGARP antibodies on the parasite's morphology, mitochondrial membrane potential, and food vacuole integrity (with elevated intracellular calcium) indicates activation of programmed cell death as a mechanism of parasite killing. To further explore the mechanism of parasite death, anti-PfGARP treated parasites were evaluated for the activation of caspase-like enzymes. GIA assays were performed and the parasites were probed with Apostat, a fluorescent dye that labels activated caspase-like cysteine proteases. Parasites treated with anti-PfGARP showed marked activation of caspase-like protease as assessed by flow cytometry (FIGS. 3A-3C).

Additionally, TUNEL assays were performed to determine whether treatment with anti-PfGARP resulted in parasite DNA fragmentation. GIAs were performed using parasites that had been treated with pre-immune or anti-PfGARP-A sera followed by fluorescent dye-based TUNEL labeling. Parasites treated with anti-PfGARP showed marked fragmentation of their DNA as assessed by flow cytometry (FIG. 3D).

Moreover, understanding the mechanism of anti-PfGARP mediated killing is critical as no anti-malarial antibody has ever been demonstrated to kill intra-erythrocytic parasites in the absence of complement or cellular effector mechanisms. Extensive experimentation was conducted to refine the understanding of the factors necessary for anti-PfGARP mediated killing, and to identify how binding of anti-PfGARP to the exofacial surface of trophozoite infected RBCs results in parasite death.

Studies were carries out to determine whether antibody mediated cross-linking of PfGARP on the surface of trophozoite infected RBCs was necessary for parasite killing. The recombinant mAb was expressed as a mono-valent Fab in COS cells (without interchain disulfide bond) and incubated this Fab with *P. falciparum* parasites in a standard growth assay (FIGS. 27 A and 27B). Mono-valent Fab anti-PfGARP inhibited parasite growth by 45.4% compared to media alone, confirming that cross-linking of surface expressed PfGARP is not necessary for the parasiticidal effect of anti-PfGARP (see FIG. 9A-9D).

When trophozoite infected RBCs were treated with anti-PfGARP, the parasite underwent an apoptotic-like death with loss of mitochondrial membrane potential, disruption of the food vacuole with release of calcium, caspase-like activation, and parasite DNA fragmentation.

These data, including: 1) Long term culture of parasites treated with anti-PfGARP, 2) SBF-SEM based imaging of the food vacuole, 3) Fab anti-PfGARP mediated killing of trophozoite infected RBCs, 4) anti-PfGARP mediated induction of caspase-like enzymes, and 5) anti-PfGARP mediated DNA fragmentation are provided herein.

Example 4: Protein Processing of PfGARP

*P. falciparum* exports proteins to the RBC cytoplasm and membrane using the *Plasmodium* export element (PEXEL) motif followed by its cleavage in the endoplasmic reticulum by plasmepsin V, as well as by other, non-PEXEL mediated mechanisms (Jacobs, G. H. et al. *The American journal of tropical medicine and hygiene* 39, 15-20 (1988)). PfGARP encodes an amino terminal signal sequence/transmembrane region (aa 1-22; EDKDGVEI) and an appropriately located PEXEL element (aa 48-52). To determine whether parasites process and cleave the PEXEL element, parasite extracts were probed using peptide-specific antisera generated against peptides that flank the PEXEL element (aa 31-48 and aa 504-522). As expected, both peptide-specific antibodies recognized full length (aa 1-673) recombinant PfGARP while only the antibodies raised against aa 504-522 recognized rPfGARP-A (aa 410-673). Only the antibodies raised against aa 504-522 recognized native PfGARP in trophozoite-infected RBCs confirming that the PEXEL element (and therefore the signal sequence/transmembrane domain) in PfGARP is processed and cleaved from the mature protein (FIGS. 18A-18E). Because mature PfGARP lacks a transmembrane domain and consensus sequences for glycophosphatidylinositol or palmitic acid anchors, the mechanism of attachment of PfGARP to the exofacial surface of the RBC membrane remains unknown but may include interactions with RBC or trophozoite-infected RBC surface proteins. Supporting this notion, recent evidence indicates that a highly charged 28 aa peptide from PfGARP (aa 417-444) containing 5 lysine-rich repeats is able to bind to Band 3 (Almukadi, H. et al. *Blood* 133, 470-480(2019)).

Example 5: Anti-PfGARP Arrests Trophozoites In Vitro

To determine the parasite stage at which anti-PfGARP antibodies arrest growth and kill parasite, trophozoite arrest assays were performed using anti-PfGARP-A antisera prepared by either DNA or recombinant protein immunization (FIGS. 19A-19E). Parasites were synchronized to the ring stage at high (5%) parasite density, incubated with anti-PfGARP-A antisera or controls for 36 hours followed by enumeration of trophozoite-stage parasites. Under these conditions, the majority of ring infected RBCs should have developed into late stage schizonts. Anti-PfGARP-A antisera generated by DNA plasmid-based immunization (FIG. 19A), recombinant protein immunization (FIG. 19B), purified mouse anti-PfGARP-A (FIG. 19C) or purified human anti-PfGARP-A (FIG. 19D) inhibited trophozoite development resulting in 80-90-fold higher proportion of trophozoites compared with controls (all P<194 0.001).

Time course analyses confirmed that the increased number of trophozoites observed in anti-PfGARP-A treated cultures was due to the inability of parasites to progress past this stage (FIG. 19E) and the arrested trophozoites displayed a dysmorphic, pyknotic appearance consistent with crisis forms associated with dying/dead parasites on Giemsa-stained blood smears (Rathore, S., et al. *Cell Death &*

*Disease* 6, e1 803(2015) and Almukadi, H. et al. *Blood* 133, 470-480(2019)) (FIGS. 20A-20D).

Example 6: PfGARP is the Target of Protective Antibodies in Humans Tanzanian Birth Cohort To evaluate the impact of naturally acquired anti-PfGARP antibodies on clinical malaria, anti-PfGARP IgG antibody levels were measured using a fluorescent, bead-based assay in the birth cohort and related these levels to subsequent malaria outcomes. PfGARP (aa 1-673) was expressed in a mammalian expression system as a fusion protein with green fluorescent protein and purified and immobilized this construct 203 to beads according to the published methods (Almukadi, H. et al. *Blood* 133, 470-480(2019), Ockenhouse, C. F., et al. *J Immunol* 133, 1601-1608 (1984) and Oleinikov, A. V. et al. *PLoS Pathogens* 5, e1000386, (2009)).

Anti-PfGARP IgG antibody levels were measured in available plasma obtained at a scheduled, non-sick visit at 48 weeks of life in 246 children. For each antibody measurement, the analysis interval for malaria outcomes extended from the time of the antibody measurement until the child completed the study. The average duration of follow-up was 64 weeks per child. Anti-PfGARP antibodies were detectable in 48.8% of these samples and children were followed for a total of 15,737 child-weeks of observation.

Figure 4A:
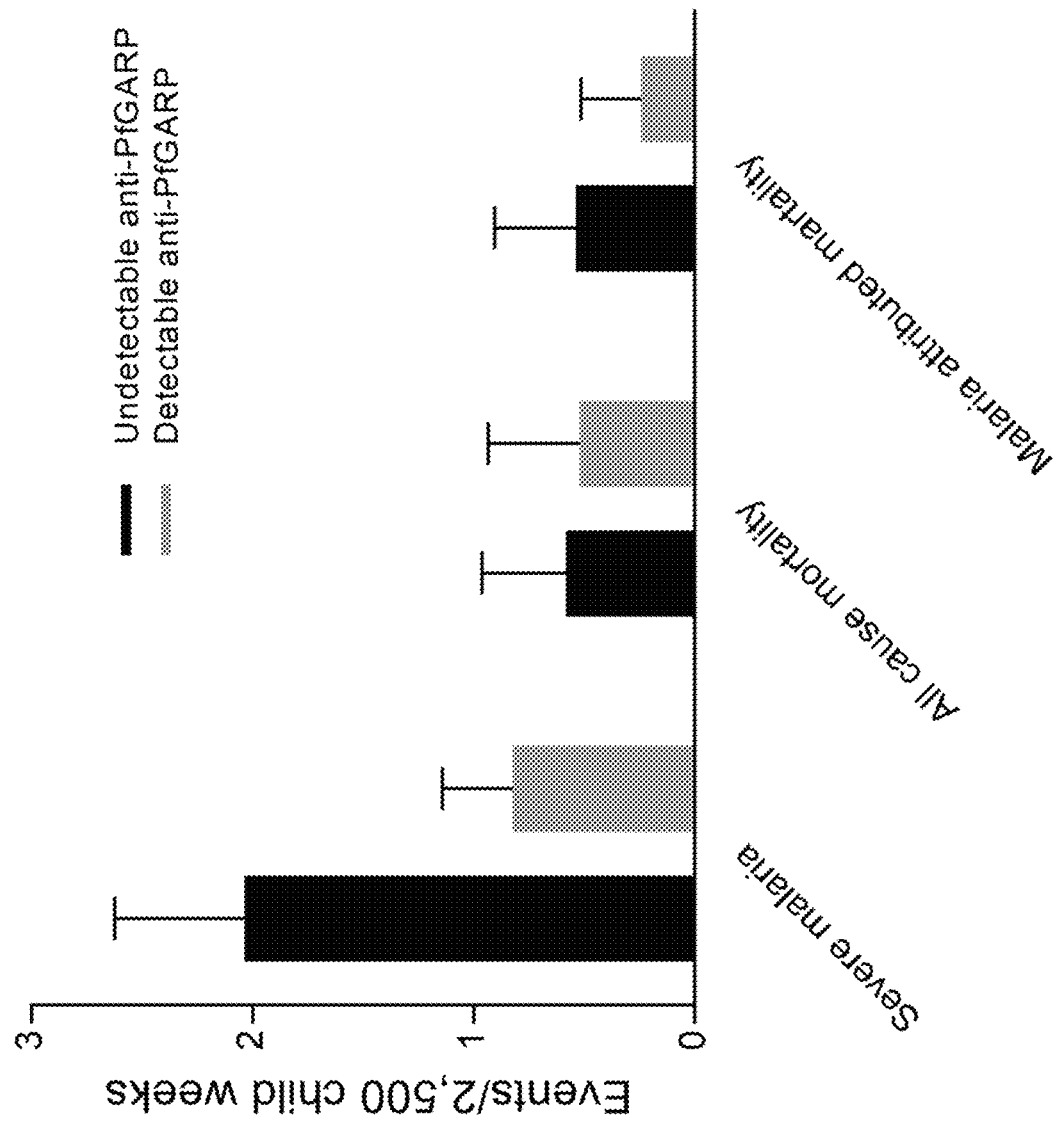
FIGS. 4A and 4B are graphs showing that antibodies to PfGARP predict reduced risk of severe malaria and parasitemia.

Generalized estimating equation (GEE) repeated measures models were used to evaluate the relationship between anti-PfGARP IgG levels and risk of malaria outcomes. When analyzed as a continuous variable, anti-PfGARP IgG levels predicted significantly decreased risk of severe malaria over the follow-up period (P=213 0.008). When analyzed dichotomously, individuals with undetectable IgG anti-PfGARP antibodies (n=126 individuals who contributed 7,327 weeks of follow-up) had 2.5-fold higher risk of severe malaria than individuals with detectable IgG anti-PfGARP antibodies (n=120 individuals who contributed 8,410 weeks of follow-up, 95% CI [1.2, 5.5], P=0.018, FIG. 4A). These results remained significant (OR=2.5, 95% CI [1.1-5.5], P=0.026) even after adjusting for potential confounders.

Kenyan Cohort

To generalize these results to a completely independent cohort, anti-rPfGARP-A IgG responses were measured in a cohort of Kenyan males participating in a treatment-reinfection study (Oleinikov, A. V. et al. *PLoS Pathogens* 5, e10impor00386, (2009), Oleinikov, A. V. et al. *The Journal of infectious diseases* 196, 155-164(2007) and Oleinikov, A. V. et al. *PloS One* 7, e31011(2012)). Volunteers were residents of subsistence farming, *P. falciparum*-endemic villages in western Kenya, north of Lake Victoria. The entomological inoculation rate in this area at the time of this study exceeded 300 infectious bites per person per year (Kurds, J., et al. *Am. J. Prop. Med. Hyg.* 309) and bednets had not yet been introduced into the community. Volunteers (N=135) aged 12-35 years were entered into the study at the beginning of the high transmission season in April, 1997. Detectable parasitemia was eradicated with quinine sulfate (10 mg/kg BID x3d) and doxycycline (100 mg BID x7d) and individuals were followed with weekly blood smears for 18 weeks. Serum was collected 2 weeks post-treatment and stored at −80° C. In this age group, clinical or severe malaria is very uncommon.

Figure 4B:
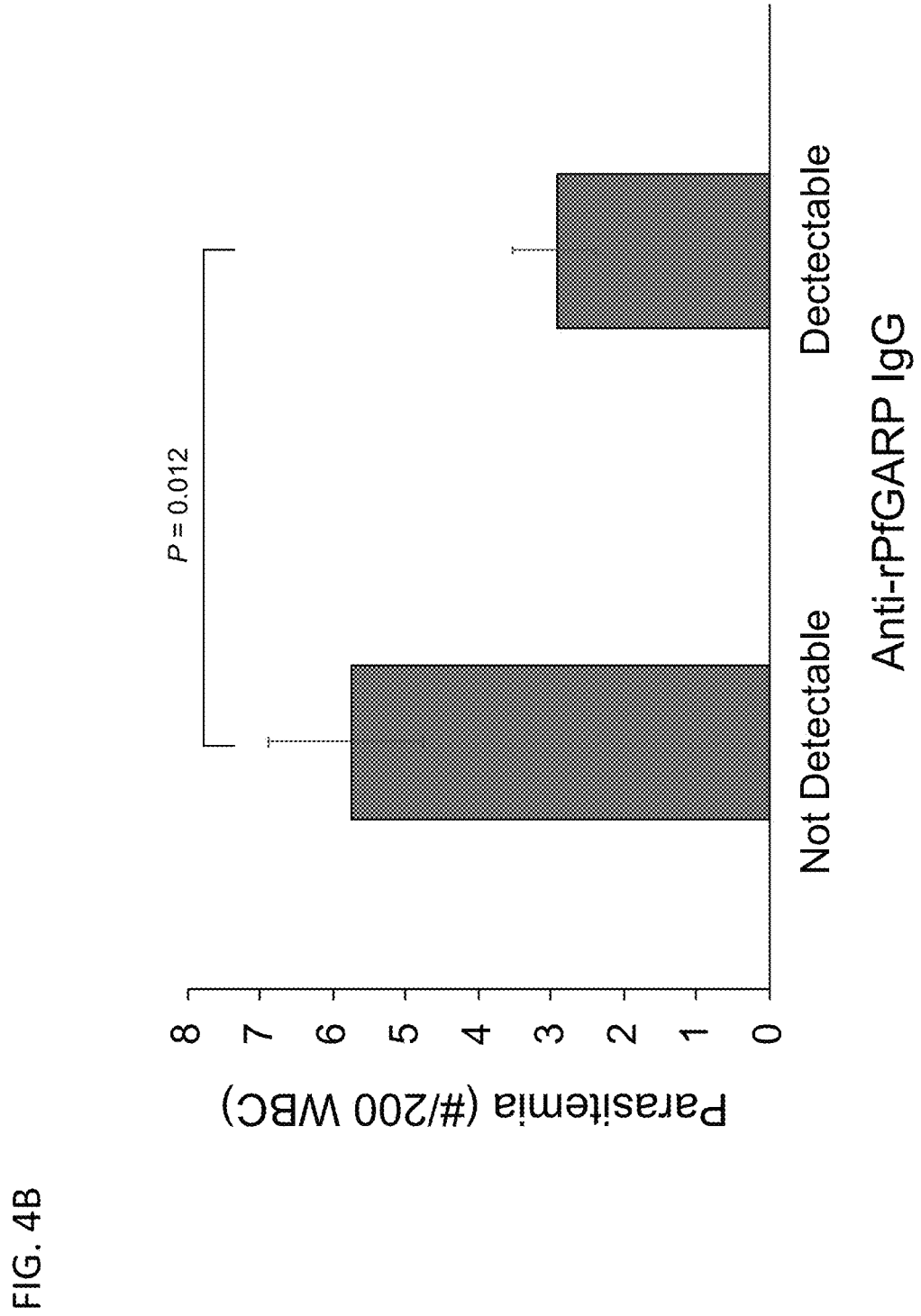

In GEE based repeated measures models, IgG anti-rPfG-ARP-A antibodies, when analyzed as a continuous variable, predicted significantly decreased parasite density over 18 weeks of follow-up (P<0.004). When analyzed dichotomously, individuals with undetectable IgG anti-rPfGARP-A antibodies (n=61 individuals who contributed 1,018 weeks of follow-up blood smears), had 1.97-fold higher parasite densities over 18 weeks of follow-up compared to individuals with detectable IgG anti-rPfGARP-A antibodies (n=74 individuals who contributed 1,237 weeks of follow-up blood smears, 95% CI [0.94, 4.23], P=0.012, see FIG. 4B). These results remained significant (OR=1.82, 95% CI [0.9-3.7], P=0.019) even after adjusting for potential confounders.

Previously, measured IgG antibody levels were measured to MSP-3 (aa 99-265), MSP-7 (aa 117-248), LSA-N (aa 28-150), LSA-C (aa 1630-1909), and RAMA-E (aa 759-840) in these same samples. Antibodies to these antigens did not predict resistance to parasitemia (Raj, D. K. et al. *Science* 344, 871-877, (2014)). While antibody responses to additional blood stage antigens are undoubtedly important for resistance to *P. falciparum*, and the potential for residual confounding by unmeasured factors cannot be completely excluded from the epidemiologic analyses, the data obtained from two independent longitudinal human cohorts that differ in location and age provide compelling evidence for a direct relationship between anti-PfGARP IgG responses, and resistance to parasitemia and severe *P. falciparum* malaria in humans.

Example 7: Vaccination with Nucleoside-Modified PfGARP-A mRNA-LNP Vaccine Partially Protects Monkeys from *P. falciparum* Challenge Because PfGARP does not have orthologs in any non-primate malaria species, a vaccine trial was conducted in the *P. falciparum*/Aotus model. Nucleoside-modified, FPLC-purified mRNA vaccines against Zika and influenza viruses have demonstrated potency in small and large animals (Kurds, J. D., et al. *Infect. Immun.* 69, 123-128(2001), Nixon, C. P. et al. *J. Infect. Dis.* 192, 861-869(2005), and Beier, J. C. et al. *Am J Trop Med Hyg* 50, 529-536 (1994)), thus n=5 monkeys were immunized intradermally with 50 μg of lipid nanoparticle (LNP) encapsulated nucleoside-modified mRNA encoding PfGARP-A. Control monkeys (n=4) were intradermally immunized with 50 μg of poly (C) RNA-LNPs. Monkeys received 3 doses at 3-week intervals. Prior to each dose, serum was obtained for antibody assays. On day 63, monkeys were challenged with $10^4$ *P. falciparum* FVO strain blood stage parasites by IV injection followed by daily blood films. This represents a heterologous challenge with a highly virulent parasite as the sequence for the mRNA-LNP vaccine was derived from the 3D7 strain.

Figure 5A:
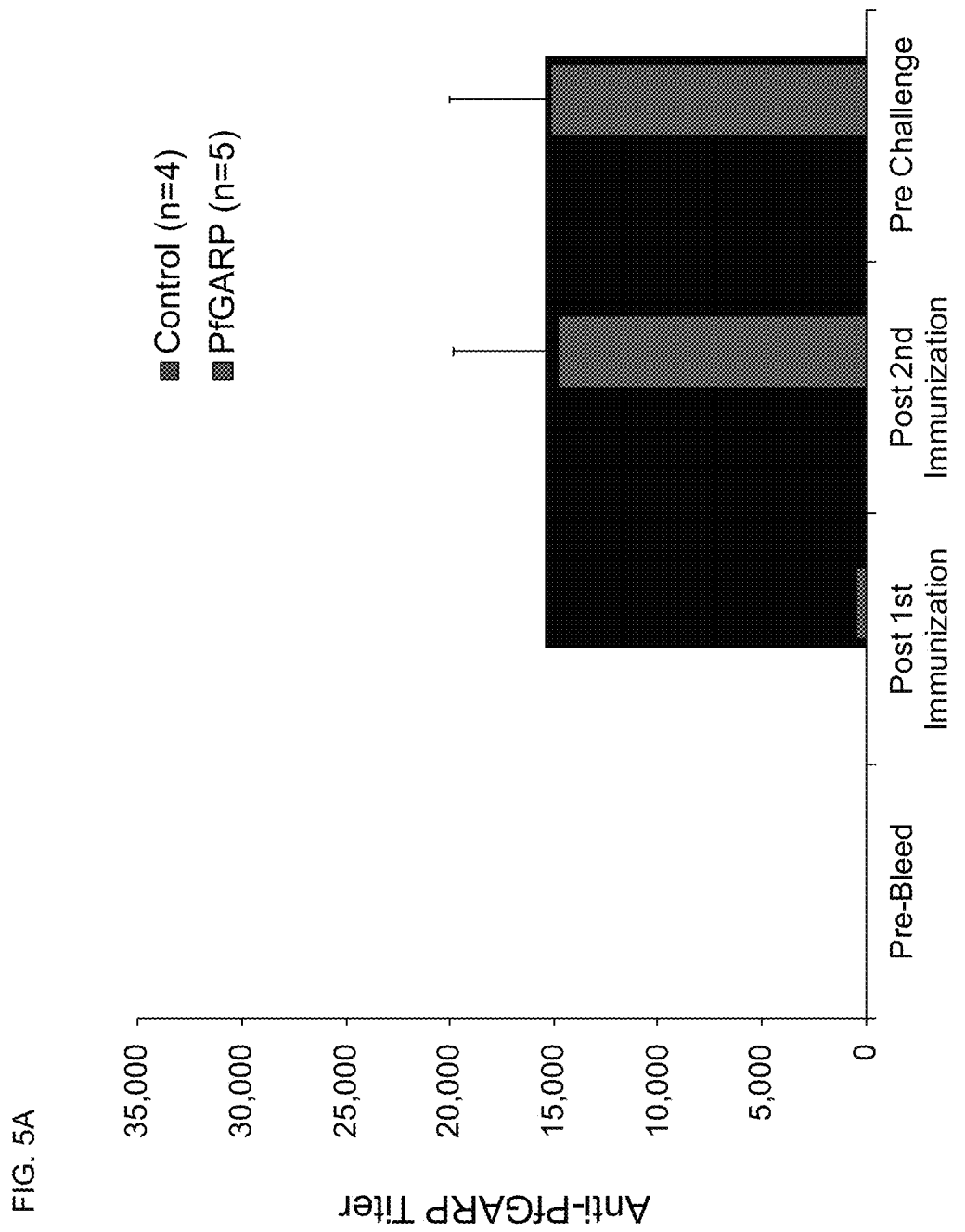
FIGS. 5A and 5B are graphs showing that vaccination with PfGARP-A encoding nucleoside-modified mRNA-LNPs protected monkeys from challenge with *P. falciparum*.
Figure 5B:
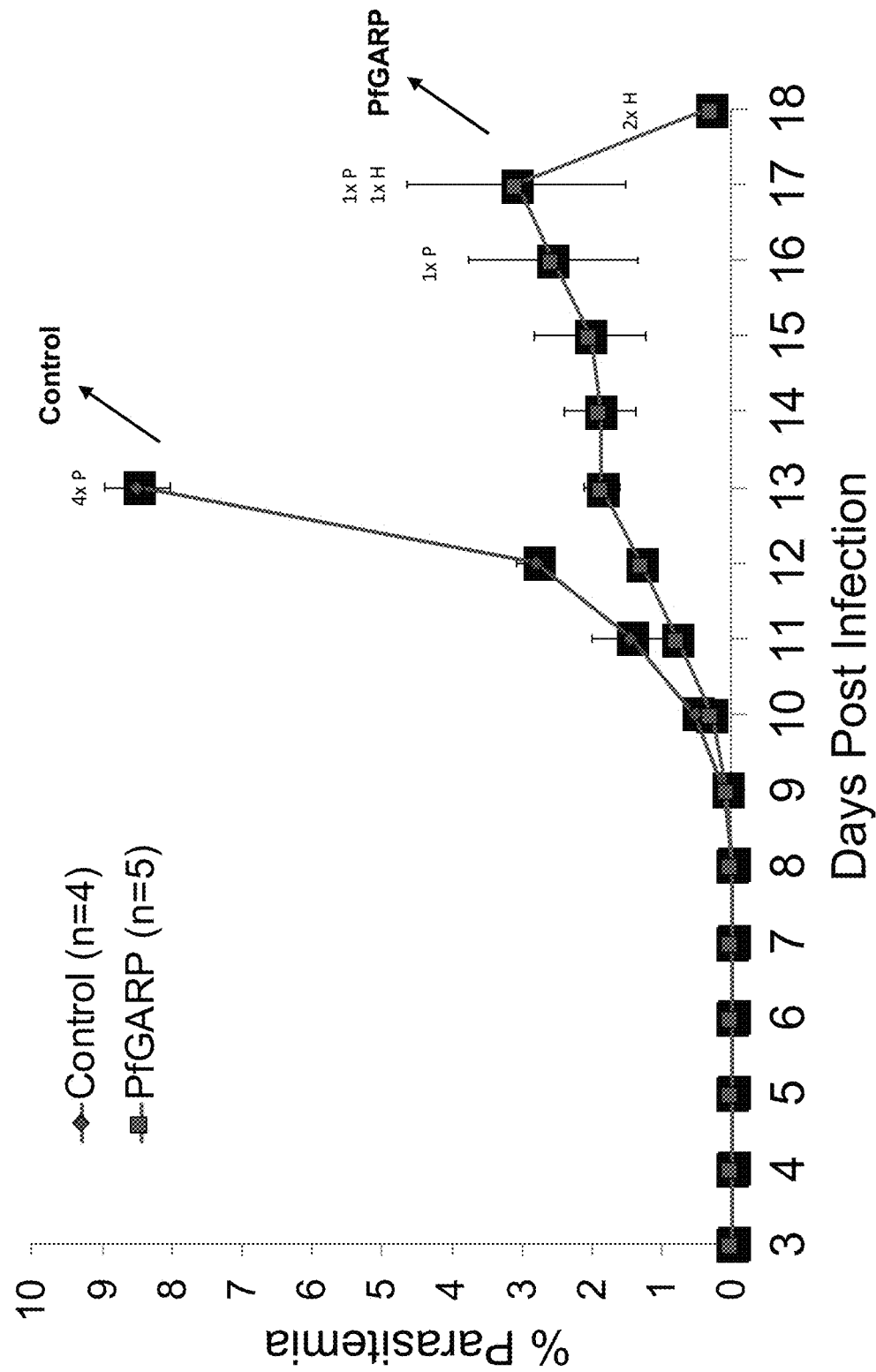
Figure 21:
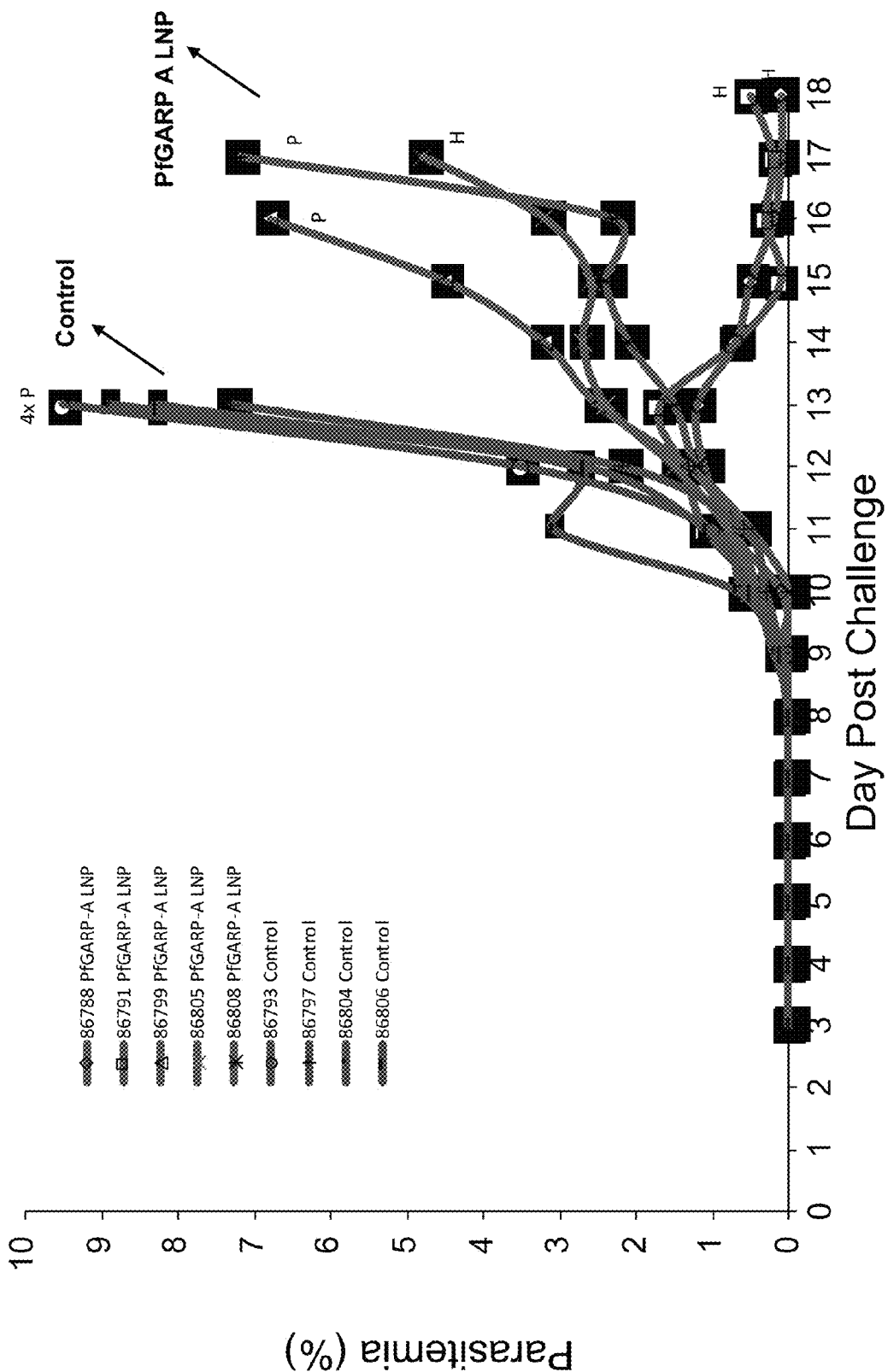
FIG. 21 is a graph showing individual parasitemia data from monkey trial presented in FIG. 5. Aotus monkeys vaccinated with rPfGARP-A formulated as a lipid encapsulated mRNA (n=5) and control monkeys vaccinated with lipid encapsulated poly C (n=4) were challenged IV with $10^5$ P. falciparum infected RBC. H indicates treatment for low hemoglobin, P indicates treatment for high parasitemia.

Immunized monkeys generated antibody responses that plateaued after the second injection (FIG. 5A). Control monkeys had significantly higher parasitemia than monkeys immunized with PfGARP-A on day 12 (P<0.009) with a 4.6-fold higher parasitemia on day 13, the final day with complete follow-up of all monkeys (P<0.001, FIG. 5B). All control monkeys met pre-specified criteria for anti-malaria treatment on day 13 due to hyperparasitemia (parasitemia>7.5%). One PfGARP-A vaccinated monkey was treated for hyperparasitemia on day 16 and one was treated on day 17. One monkey was treated for anemia, a common complication in the Aotusl *P. falciparum* model 28, on day 17 and the remaining 2 monkeys were treated for anemia on day 18, despite controlling their parasitemias (FIG. 21). Notably, the three monkeys which controlled their parasitemia and required treatment for anemia had higher antibody titers (16,000, 16,000 and 32,000) compared to the monkeys which required treatment for their parasitemias (8,000 and 4,000).

Figure 22A:
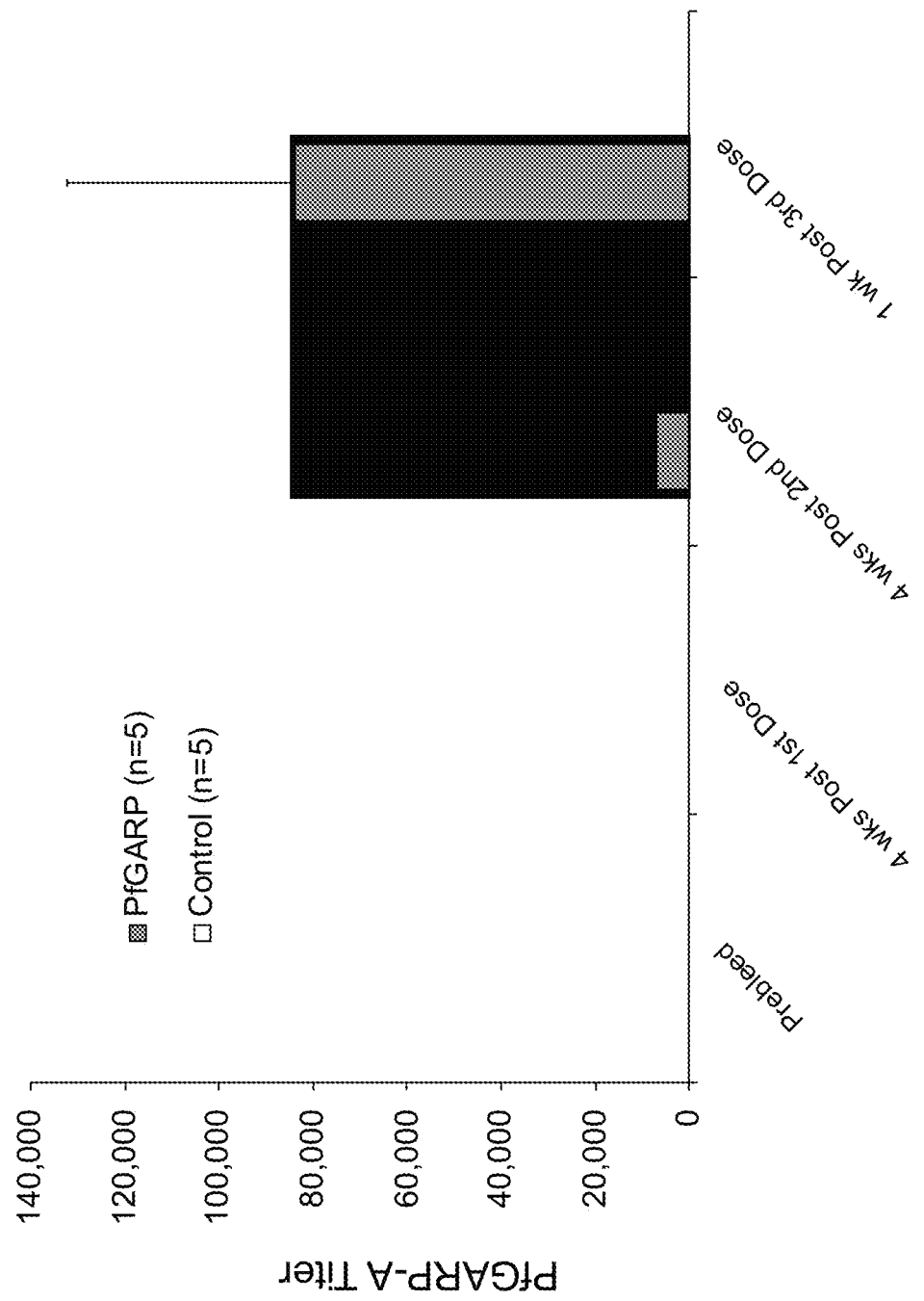
Figure 22B:
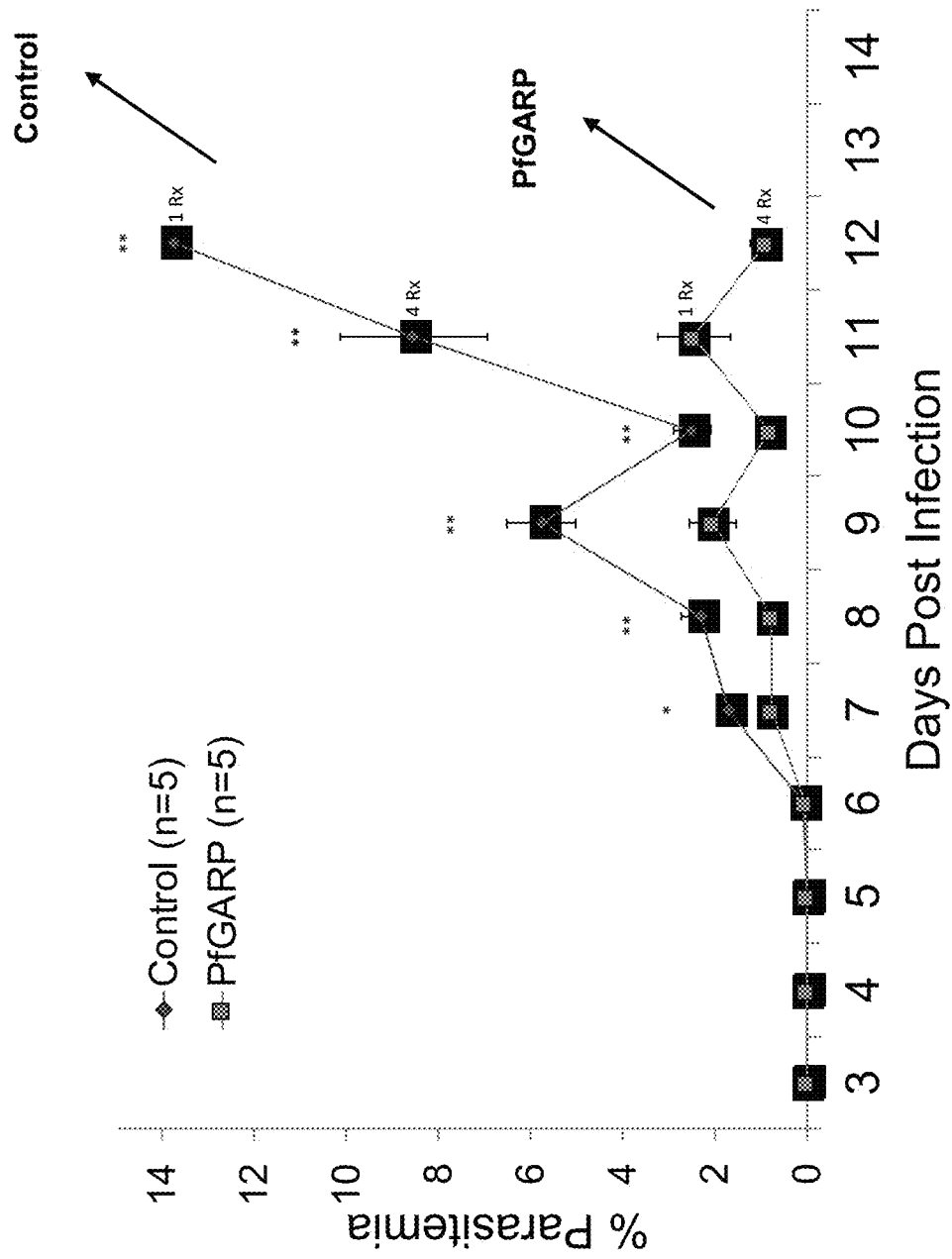

Vaccination with PfGARP-A in Ribi Adjuvant Partially Protects Monkeys from *P. Falciparum* Challenge A trial using *E. coli* expressed recombinant PfGARP-A (aa 410-673) emulsified in Ribi adjuvant as the immunogen in the *P. falciparum*/Aotus model was conducted. Monkeys were immunized (n=5 monkeys) with 50 μg of PfGARP-A in Ribi adjuvant or Ribi alone (n=5) sub-cutaneously. Monkeys received 3 doses at 3-week intervals. Prior to each dose, sera were obtained for antibody assays. On day 63, monkeys were challenged with $10^4$ *P. falciparum* FVO strain blood stage parasites by IV injection followed by daily blood films. Immunized monkeys generated antibody responses that rose after the third injection (FIG. 22A). Importantly, control monkeys had significantly higher parasitemia on days 7-12 compared to PfGARP-A vaccinated animals (all P<0.05, FIG. 22B). On day 11, the final day with complete follow-up of all monkeys, controls had 3.5 fold higher parasitemia compared to PfGARP-A vaccinated monkeys (P<0.01). Four control monkeys met pre-specified criteria (parasitemia>7.5%, hematocrit<25%, or evidence of clinical illness) for drug treatment on day 11 and the final control monkey met criteria on day 12. On Day 11, one PfGARP vaccinated monkey was drug treated despite not meeting pre-specified criteria.

Antibodies to PfGARP Kill *Plasmodium falciparum* Malaria Parasites and Protect against Infection and Severe Disease Malaria remains a leading cause of childhood mortality, and vaccines are urgently needed to attenuate this public health threat. A vaccine antigen discovery method was utilized to identify novel vaccine candidates recognized by antibodies expressed in relatively resistant, but not susceptible children. Using the optimized phage-display based approach, PfGARP was identified, a novel blood stage vaccine candidate which localizes to the exofacial surface of the RBC membrane in trophozoite infected RBCs.

PfGARP was identified based on screening a *P. falciparum* cDNA expression library with uncharacterized sera obtained from adults living in Papua New Guinea (Pardi, N. et al. *Nature* 543, 248-251(2017)). Interestingly, in the same Tanzanian birth cohort used to clone and validate PfGARP in the present study, PfGARP was identified by RNAseq as one of only four parasite transcripts specifically upregulated in parasites infecting children compared to adults 30. The expression of PfGARP was higher in parasite isolates that bind the host receptor CD36 compared to parasites that bind CSA and expression was higher in freshly isolated field parasites than in reference strains adapted to long-term in vitro culture, suggesting that the function of this protein is not required in culture. More recently, the short lysine-rich tandemly repeated sequences of PfGARP have been identified as critical localization signals that traffic the protein to the RBC membrane (Vignali, M. et al. *The Journal of Clinical Investigation* 121, 1119-1129(2011)).

Antibodies to PfGARP significantly attenuate parasite growth by arresting and killing trophozoite infected RBCs in the absence of immune effector cells or complement. These antibodies generate marked alterations in the morphology of the food vacuole of trophozoite-infected RBCs. Importantly, anti-PfGARP antibodies have a profound killing effect on both lab-adapted as well as freshly-isolated parasites from both children and adults and this effect is mediated by relatively low concentrations of specific antibody.

This *P. falciparum*-specific antibody kills intraerythrocytic parasites in the absence of complement or immune effector cells.

The mechanisms by which anti-PfGARP mediates parasite killing without engaging immune effector functions was probed. Parasites treated with anti-PfGARP displayed several canonical features of programed cell death (PCD) including: 1) shrunken, pyknotic nuclei, 2) loss of mitochondrial membrane integrity, 3) activation of caspase-like proteases, 4) activation of DNA fragmentation, and 5) release of calcium from intracellular stores. *P. falciparum* lacks canonical caspases, but does encode three meta-caspases (Vandana, Dixit, et a. *Frontiers in Pharmacology* 10, 790(2019)) and activation of PfMCA1 functions as an upstream activator of a caspase-like enzyme leading to parasite PCD (Meslin, B., et al. *PloS one* 6, e23867(2011)). While PCD has been reported in *Plasmodium* in response to protease and proteasome inhibitors, heat stress and drug treatment (Rathore, S., et al. *Cell Death & Disease* 6, e1803(2015), Meslin, B., et al. *PloS one* 6, e23867(2011), Ch'ng, J. H. et al. *Cell Death & Disease* 1, e26, (2010), Rathore, S. et al. *Cell Death & Disease* 2, e231, (2011), Matthews, H. et al. *Malaria Journal* 11, 297, (2012), Engelbrecht, D. & Coetzer, T. L. *Cell Death & Disease* 4, e971, (2013), Lang, E. & Lang, F. *BioMed Research International* 2015, 513518, (2015), and Gunjan, S. et al. *Apoptosis: an international journal on programmed cell death* 21, 955-964 (2016)), anti-PfGARP is the first example of an antimalarial antibody that is able to activate parasite PCD. Because PfGARP is located on the exofacial surface of the RBC and antibody engagement of PfGARP leads to activation of parasite PCD, PfGARP may function in the density dependent regulation of parasitemia by sensing parasite or host factors (Mutai, B. K. & Waitumbi, J. N. *Malaria Journal* 9 Suppl 3, S6, (2010), Engelbrecht, D. & Coetzer, T. L. *Parasitology International* 65, 715-727, (2016), and Chou, E. S. et al. *The FEBS journal* 285, 848-870, (2018)).

In a vaccine-challenge experiment in non-human primates, immunization with a PfGARP-A-encoding nucleoside-modified mRNA-LNP vaccine conferred marked protection against parasitemia following a heterologous challenge with *P. falciparum* compared with controls with 2 out of 5 monkeys controlling their parasitemias. Similar results in non-human primates vaccinated with recombinant PfGARP protein were also obtained. These data demonstrate protection against *P. falciparum* following vaccination with an mRNA based vaccine.

In a longitudinal cohort of Kenyan adolescents and adults, individuals with undetectable anti-PfGARP antibodies had 2.0-fold higher parasite density over 18 weeks of weekly blood films compared to individuals with detectible anti-PfGARP. In an independent longitudinal cohort of Tanzanian children, individuals with undetectable anti-PfGARP antibodies had 2.5-fold higher risk of severe malaria over 2.5 years of follow-up compared to individuals with detectible anti-PfGARP antibodies.

The data define PfGARP as a rationally identified vaccine candidate for *P. falciparum* malaria indicate that the recombinant monoclonal anti-PfGARP antibody could serve as a platform for developing therapeutic and prophylactic antibody-based interventions and function in high-throughput drug screens targeting PfGARP-induced PCD. By killing trophozoite infected RBCs, immunization with PfGARP can be used with other vaccines targeting hepatocyte invasion (Daily, J. P. et al. *The Journal of Infectious Diseases* 191, 1196-1203, (2005)) and red cell invasion (Ralph, S. A. et al. *Genome Biology* 6, R93, (2005)) or egress (Raj, D. K. et al. *Science* 344, 871-877, (2014)) to achieve a synergistic effect.

The following materials and methods were used to generate the data described herein.

Tanzanian Birth Cohort
  Study Population
  Subjects participated in the Mother-Offspring Malaria Studies (MOMS) project, which is based at Muheza Designated District Hospital (DDH), in north eastern Tanzania. Mothers presenting at Muheza DDH for delivery were enrolled and provided signed, informed consent prior to participation of themselves and their newborns in the study. The entomologic inoculation rate in the study site exceeds 400 infectious mosquito bites per person per year (Ellman, R., et al. *Annals of tropical medicine and parasitology* 92, 741-753 (1998)). Details of the MOMS study design, enrolment methods, and exclusion criteria have been published elsewhere (Mutabingwa, T. K. et al. *PLoS medicine* 2, e407, doi:10.1371/journal.pmed.0020407 (2005) and Kabyemela et al *J. Infect. Dis.* 198, 163-166, doi: 10.1086/589512 (2008)).
  Inclusion Criteria and Clinical Monitoring
  785 children were monitored (N=785 children) for *P. falciparum* infection from birth up to 3.5 years of age. Children were evaluated at routine, well-child visits by a clinician every two weeks from birth to one year of age, and monthly thereafter, including blood smear analysis. Routine blood samples were collected once every 6 months from 1.5 to 3.5 years of life. Blood smears and blood samples were also collected any time the child became sick. Sick children were examined by a medical officer upon presentation to the hospital or mobile clinic. Treatment outside the study was minimized by active, weekly surveillance by the mobile clinics.
  Clinical malaria was defined as asexual *P. falciparum* parasitemia by blood smear coupled with symptoms suggestive of malaria such as temperature >37.5° C., nausea or vomiting, irritability, and poor feeding. Prompt treatment was provided to sick children according to the guidelines of the Tanzanian Ministry of Health, and study participants were instructed to obtain all medications including antimalarial through the project staff.
  Sample Collection and Processing
  Venous blood was collected and stored at 4° C. until processing. Following centrifugation, plasma was stored at −80° C. *P. falciparum* parasitemia was determined by Giemsa-stained thick blood smears prepared from the capillary or venous blood. Parasite density was expressed as the number of asexual stage parasites/200 white blood cells in the thick smear. Sickle cell trait was determined by electrophoresis (Helena Laboratories, Beaumont, Tex. USA). Hemograms were obtained on an impedance-based analyzer (Abbott Cell Dyne® 1200).
  Case Definitions
  Mild malaria was defined as a positive blood smear and one or more of the following: 1) anemia defined by Hgb <8 g/dL; 2) vomiting; 3) diarrheal disease or gastroenteritis; 4) lower respiratory infection, or 5) oral temperature >=38 deg C.
  Severe malaria was defined as a positive blood smear and one or more of the following: 1) respiratory distress defined by respiratory rate of >40/min for children older than two months of age or a respiratory rate of >50/min for children less than two months of age; 2) a history of one or more convulsions in the twenty-four hours prior to or during hospitalization; 3) prostration defined by inability to sit unaided; 4) hypoglycemia defined by glucose <2.2 mmol/L; 5) severe anemia defined by Hgb <6 g/dL; or 6) oral temperature >40 deg C.
  Malaria-associated mortality was defined as death with a positive blood film obtained during the terminal illness. One child who died of bacterial meningitis, but had a positive blood film was adjudicated as a non-malarial death.
Kenyan Cohort
  Study Population
  To generalize the protective nature of anti-PfGARP antibodies, anti-PfGARP antibody levels were measured in an entirely distinct longitudinal cohort using epidemiologic data and blood samples that were collected in 1997 as part of a treatment-reinfection study (Kurds, J. D., et al. *Infect. Immun.* 67, 3424-3429 (1999) and Kurds, et al. *Infect. Immun.* 69, 123-128, (2001)). Volunteers were residents of subsistence farming; *falciparum* endemic villages in western Kenya north of Lake Victoria, The entomological inoculation rate in this area can exceed 300 infectious bites per year (Beier, J. C. et al. *Am J Prop Med Hyg* 50, 529-536 (1994)). After obtaining informed consent, 144 males aged 12 to 35 years were entered into the study at the beginning of the high transmission season in April 1997.
  Detectable parasitemia was eradicated in 143 of the 144 participants with quinine sulfate (10 mg/kg twice daily for 3 days) and doxycycline (100 mg twice daily for 7 days). One volunteer remained parasitemic during the week following treatment and was removed from the analysis, and five volunteers did not have available serum samples, thus the analytic sample size of n=138. Immunologic and epidemiologic analyses of this cohort have been reported elsewhere (Kurds, et al *Infect. Immun.* 67, 3424-3429 (1999), Kurds, J. D., et al *Infect. Immun.* 69, 123-128 (2001), Friedman, J. F. et al. *J. Infect. Dis.* 188, 449-457, (2003), and Gourley, I. et al. *J. Infect. Dis.* 186, 1007-1012, 947 (2002)).
  Malaria assessment: Thick and thin blood smears were obtained from each volunteer prior to treatment and then weekly for 18 weeks after treatment to quantify reinfection. Each smear was interpreted by two microscopists and the mean of the two values recorded.
  Entomology measurements: The intra-domiciliary female anopheline abundance was measured weekly for 18 weeks in each volunteer's domicile using the Daytime Resting Indoors (DRI) method (Gunasekaran, K., et al. *Acta Prop* 58, 1-11 (1994)) as previously described (Kurds, J. D., et al. *Infect. Immun.* 67, 3424-3429 (1999)).
  Blood collection. Two weeks after treatment with quinine and doxycycline, volunteers donated 66 ml of blood into heparinized tubes. Within four hours of collection, samples were centrifuged, and plasma was aliquoted and stored at −80° C. for subsequent analysis.
  Clinical assays: Sickle cell trait was determined by electrophoresis (Helena Laboratories, Beaumont, Tex. USA).
Differential Screening and Characterization of PfGARP
  Selection of Resistant and Susceptible Individuals for Differential Screening Assays
  The overall purpose was to identify acquired differences in antibody repertoire that mediate resistance to parasitemia. In the cohort, parasitemia does not decline until after the age of 2 years (Raj, D. K. et al. *Science* 344, 871-877, (2014)). Any differences in parasitemia between groups that are detectable in the first 2 yrs of life, are unlikely due to differences in acquired antibody repertoire—the children have made relatively little specific antibody by this age. Therefore, the susceptibility to parasitemia is similar (and high) between the resistant and susceptible groups in the first two years of life and then diverges after 2 yrs of age was ensured. The divergence after age two is unlikely due to a constitutive (i.e. genetic) feature, but rather more likely due to an acquired phenomena (i.e. antibody repertoire). Thus, children for the two groups were selected (resistant vs susceptible) to have similar parasitemias in the first two years of life, and then to have very divergent parasitemias from age 2-4 yrs.

From the Tanzanian Birth Cohort, individuals with less than 9 of the total n=18 scheduled monthly blood smears collected between the ages of 2-3.5 yrs, individuals with less than 200 µl of plasma available from the plasma sample obtained at age 2 (+/−2 weeks), and individuals who were parasitemic when the 2 yrs (+/−2 weeks) plasma sample was obtained were excluded.

The individuals were then rank ordered based on the mean parasite density on all blood films collected between ages 2 and 3.5 yrs. This mean parasite density included the scheduled monthly blood smears as well as positive blood smears obtained during sick visits. Individuals from the low and high extremes of this distribution were chosen to comprise the Resistant (N=12) and Susceptible (N=14) groups. To minimize differential exposure as a possible confounder, Resistant individuals were selected from those children who did not sleep under bed nets, while Susceptible individuals were selected from those children who did sleep under bed nets. Selections were made with matching based on the village of residence and sex. Potential confounders examined included: Hgb phenotype, the presence of placental malaria, maternal age, birth season, and # of previous pregnancies (Table 1). By matching and demonstrating that potential non-immunologic variables influencing resistance (i.e., HbS) were not differentially distributed between the resistant and susceptible groups, the chance that these covariates were confounding the relationship between antibody specificities discovered and the outcome of resistance or susceptibility was dramatically reduced.

Whole Blood-Stage Proteome Differential Screening

A *P. falciparum* blood-stage cDNA expression library prepared in T7Select 10-3b vector (Invitrogen) was constructed using RNA prepared from freshly isolated parasites collected in the Tanzanian field site. This vector displays 5-15 copies of the cloned gene on the surface of phage capsids as a fusion with phage 10B protein.

Immulon 4HB (Thermo Fisher, USA) ELISA wells were bound with 100 µl of 1:100 dilution of sera pooled from malaria resistant children (n=12, see Table 1) for one hour at room temperature. Wells were washed five times with 1×TBST (10 mM Tris HCL, 150 mM NaCl, 0.05% Tween 20, pH 7.4) and blocked with 2% BSA in 1×TBST for one hour at room temperature. Wells were probed with 108 phage in 100 µl of 1×TBST and incubated for one hour at room temperature. Unbound phage were removed and the wells were washed five times with 1×TBST. Bound phages were then eluted in 100 µl of 5 M NaCl. Eluted phage were amplified and titered using BLT5403 bacteria according to manufacturer's instructions. Amplified eluted phage were used as input phage for 3 additional rounds of amplification. After four rounds of positive selection, eluted phage were titered and diluted to 105/ml in 1×TBST buffer. For negative selection, Immulon 4HB (Thermo Fisher, USA) ELISA wells were bound with 100 µl of 1:100 dilution of sera pooled from malaria susceptible children (n=14, see Table 1) for one hour at room temperature. 100 µli of the diluted phage (10,000 total phage) were added to the well, incubated for one hour at room temperature, and the unbound phage were collected. Unbound phage were transferred to an additional well coated with sera pooled from susceptible children, incubated for one hour at room temperature, and unbound phage collected. This process was repeated a total of five times. Following negative selection, phage were titered and 100 individual plaques were isolated and their cDNA inserts were amplified by PCR using the vector specific T7SelectUP (5'-GGAGCTGTCGTATTCCAGTC-3' (SEQ ID NO: 10)) and T7Select Down (5'-AACCCCTCAA-GACCCGTTTA-3'(SEQ ID NO: 11)) and the PCR products were sequenced.

PfGARP Expression and Purification

The ORF encoding aa 410-673 of PfGARP was subcloned into pET30 (Novagen) and transformed the resulting plasmid into the expression host *E. coli* BL21(DE3) (Novagen). The pET30 vector encodes a His tag at both the amino and carboxy ends of the recombinant protein, thus facilitating purification by metal chelate chromatography. Transformants were grown in Terrific broth supplemented with 100 µg/mL kanamycin, at 37° C. in a 10 L fermenter with oxygen sparging (10 L/min) until OD600=8.0. Isopropyl-b-D-thiogalactopyranoside was added to a final concentration of 1 mmol/L, and the culture was fed continuously with 0.3 g/ml glucose, 0.09 g/ml yeast extract at 50 ml/hr for 12 h. Cultures were harvested by centrifugation and 750 gr of wet cell paste was resuspended in 10 L of 10 mmol/L potassium phosphate, 150 mmol/L NaCl, 10 mmol/L imidazole, 0.5% Tween 20, and 0.5% Triton X 100, (pH 8.0) and lysed by high-pressure disruption at 20,000 PSI (Microfluidics, Model 110-T). The lysate was clarified by tangential flow microfiltration (filter area 1 m$^2$, pore size 1 µm, Millipore) and 8 L of clarified lysate was recovered. Protein purification was achieved by a 4-step process on BioPilot chromatography equipment (Pharmacia). Briefly, clarified lysate was applied to a LineLine Pilot 35 (GE 129 Healthcare) column containing 90 mL of Ni-NTA Superflow Resin (Novagen). The protein of interest was eluted with a stepped gradient containing increasing concentrations 130 of imidazole. Fractions containing the protein of interest were pooled, adjusted to 400 mmol/L ammonium sulfate, 10 mmol/L DTT and further purified, by hydrophobic-interaction chromatography on a Fine Line Pilot 35 (GE Healthcare) column containing 150 ml of Source 15PHE (GE Healthcare). Recombinant proteins were eluted with a linear gradient of elution buffer (10 mmol/L Tris, 1 mmole/L DTT, 1 mmol/L EDTA [pH 8.0]). Fractions containing the protein of interest were pooled and further purified, by anion exchange chromatography on a Line Line Pilot 35 (GE Healthcare) column containing 130 ml of MacroPrep High Q (BioRad). Recombinant proteins were eluted with a linear gradient of elution buffer (10 mmol/L Tris, 1 mole/L NaCl, 1 mmole/L DTT, 1 mmol/L EDTA [pH 8.0]). Final purification was achieved by ceramic hydroxyapatite chromatography on a LineLine Pilot 35 (GE Healthcare) column containing 70 ml of CHT type 1 (BioRad). Recombinant proteins were eluted with a linear gradient of elution buffer (500 mmoles/L potassium phosphate, and 1 millimole/L DTT, pH 7.4)

Purified recombinant protein, designated rPfGARP-A, was buffer exchanged into 10 mmol/L sodium phosphate, 0.05% Tween 20, 3% sucrose and concentrated to 500 µg/ml by tangential flow ultrafiltration (filter area 50 cm$^2$, pore size 5 kDa, Pall). rPfGARP was lyophilized at 500 µg/vial and stoppered under nitrogen. Endotoxin levels were less than 2 EU/mg protein as determined by an EDA cleared assay (Lonza). Typical yields are >50 mg rPfGARP per 750 gr of wet cell paste.

Figure 6C:
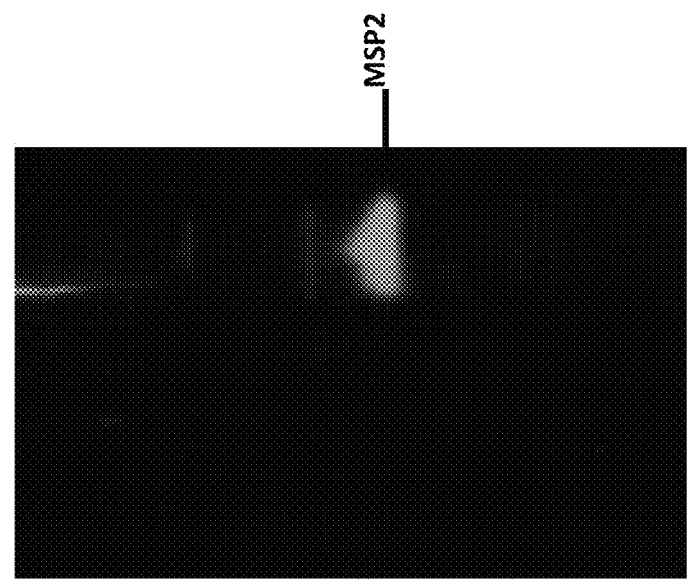
FIGS. 6A-6C are images showing that 3D7 parasites express PfGARP.
Figure 6B:
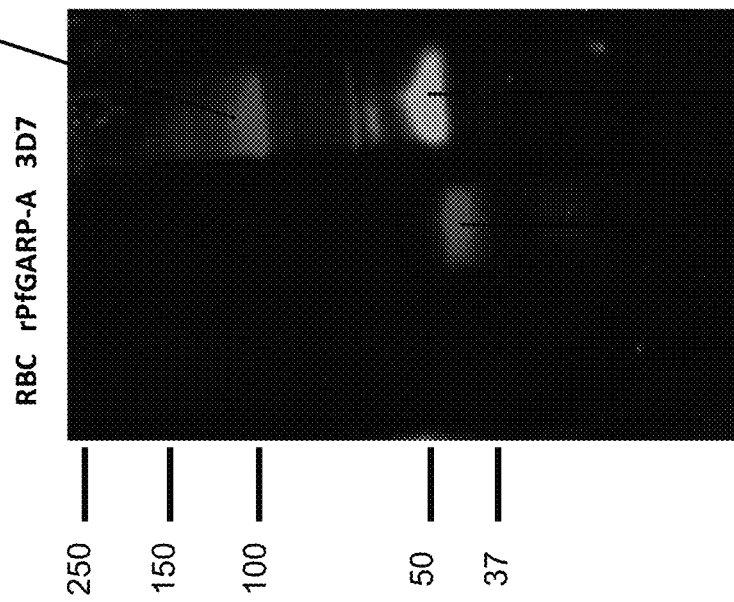
Figure 6A:
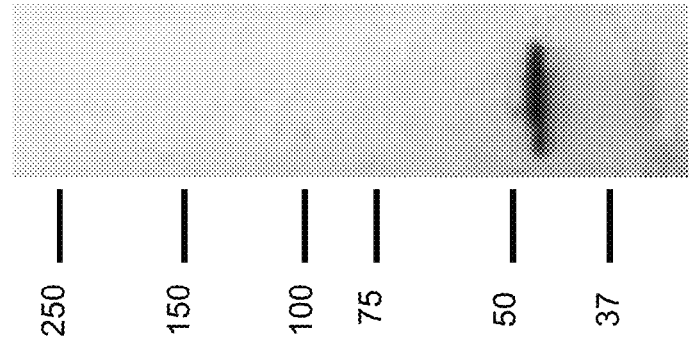
Figure 7A:
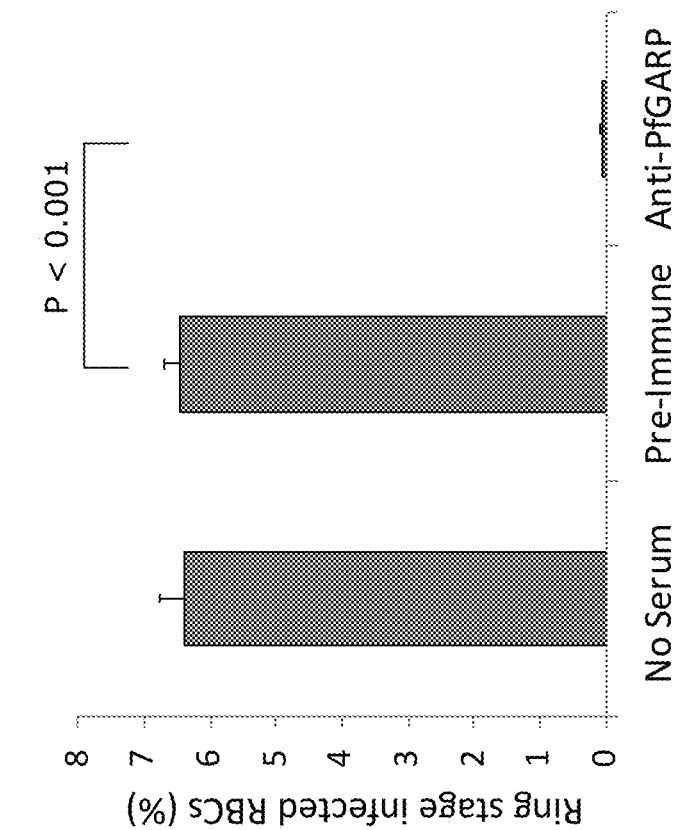
FIGS. 7A-7D are graphs showing growth inhibition assays (GIA) performed on parasites collected from the Muheza, Tanzania field site following short term culture adaptation. Assays were performed using polyclonal anti-PfGARP-A antibodies generated by recombinant protein immunization in mice (FIGS. 7A, 7B, 7C, and 7D). Ring stage malaria parasites adapted from adults, FIG. 7A (NIH 00710) and FIG. 7B (NIH 00918), and children, FIG. 7C (NIH 408551) and FIG. 7D (NIH4122821) were cultured in the presence of anti-PfGARP mouse sera at 1:10 dilution. Negative controls included no anti-sera and pre-immune mouse sera. Parasites were cultured for 48 hours at 37° C. and ring and early trophozoite stage parasites were enumerated by microscopy. Bars represent the mean of 3 independent replicates with each replicate performed in triplicate. Error bars represent SEMs. P value were calculated by non-parametric Mann-Whitney U test are indicated.
Figure 7B:
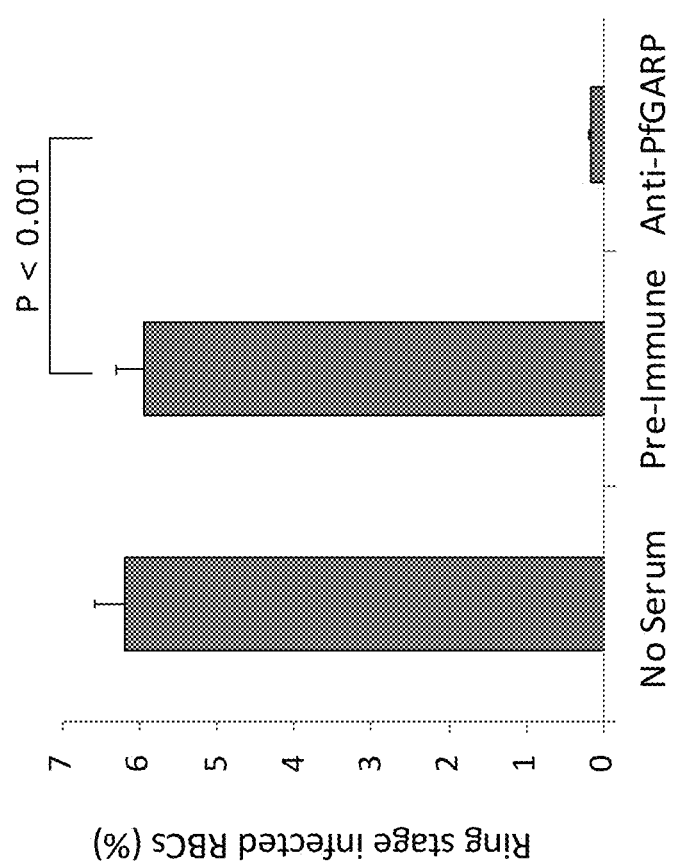
Figure 7C:
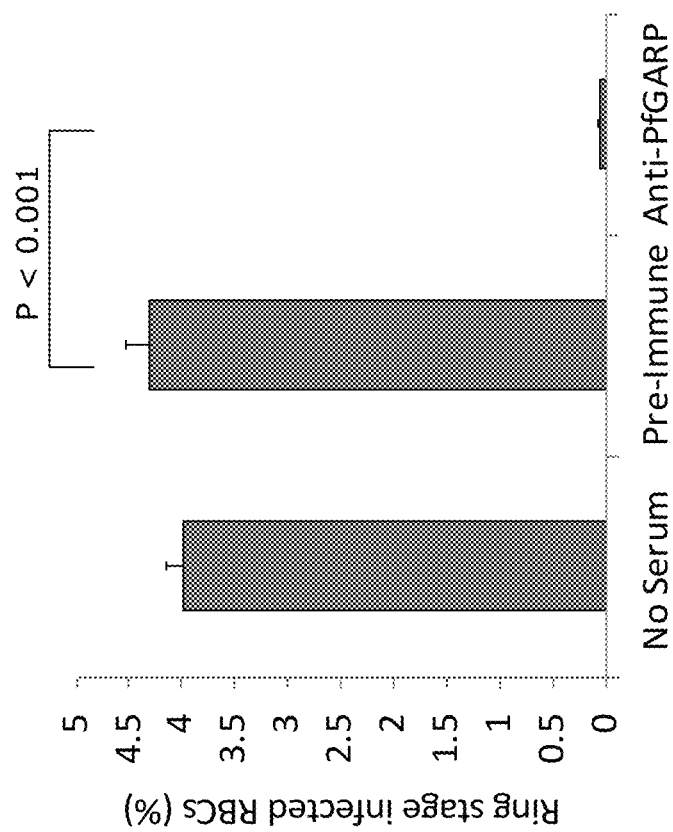
Figure 7D:
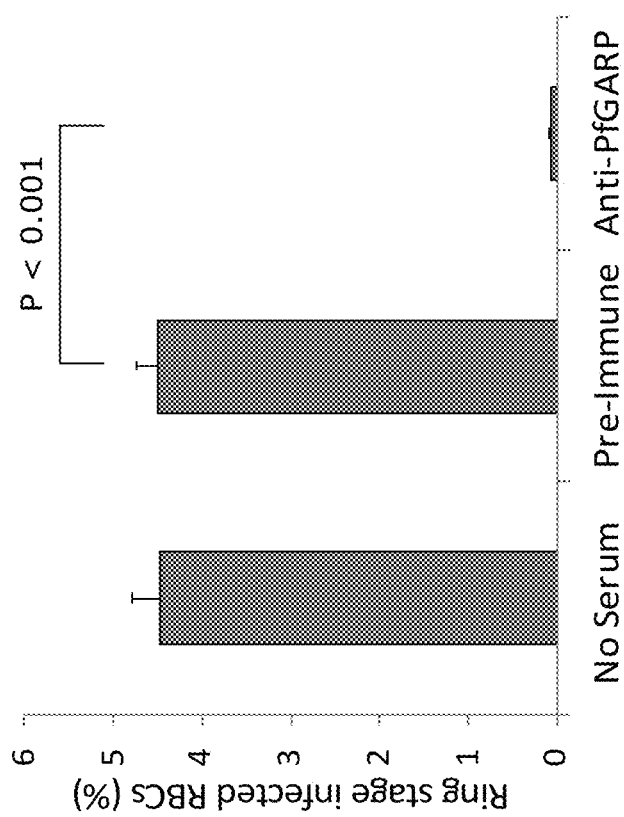

Importantly, rPfGARP-A expressed immuno-relevant epitopes, which generated functional polyclonal antibodies that block and kill trophozoites (FIGS. 1A-1K), arrest Trophozoite (FIGS. 3A-3D) and recognize native PfGARP by western blot (FIGS. 6A-6C).

Parasite Strains and Culture

*P. falciparum* strains (3D7, Dd2, and D10) were obtained from MR4. Two parasite isolates from adults and two parasite isolates from children were collected from the Tanzanian field site and culture adapted. The parasites were cultured in vitro according to the methods of Trager and Jensen with minor modifications (Trager, W. & Jensen, J. B. *Science* 193, 673-675 (1976)). Briefly, parasites were maintained in RPMI 1640 medium containing 25 mm HEPES, 5% human O+ erythrocytes, 5% Albumax II (Invitrogen), 24 mm sodium bicarbonate, and 10 μg/ml gentamycin at 37° C. with 5% $CO_2$, 1% $O_2$, and 94% $N_2$.

Anti-PfGARP Antisera

Mouse anti-PfGARP antisera were produced by either DNA or recombinant protein immunization. For DNA immunization, ORF encoding aa 410-673 of PfGARP was subcloned into VR2001, transformed into the host *E. coli* NovaBlue (Novagen), and purified endotoxin-free plasmid (Endofree Giga, Qiagen). BAFB/c mice were immunized with 100 μg of plasmid (25 μg intramuscular injection in each hind leg and 50 μg intradermal injection at the base of tail) followed by 50 μg intradermal injections at the base of tail every two weeks for a total of four doses.

For protein immunization, rPfGARP-A was emulsified in an equal volume of TiterMax adjuvant (CytRx Corporation) and injected 50 μg of rPfGARP-A intraperitoneally at two-week intervals for a total of four doses.

Affinity Purification of Anti-PfGARP Antisera

To purify polyclonal mouse and human anti-PfGARP IgG, 6 mg of rPfGARP-A was coupled to one ml of NHS-activated Sepharose 4 Fast Flow (GE Health Sciences) according to the manufacturer's instructions. For mouse anti-PfGARP IgG, plasma pooled from rPfGARP-A immunized mice was used. For Human anti-PfGARP IgG, plasma pooled from placental blood collected from women delivering in the Tanzanian birth cohort was used.

rPfGARP-A coupled resin was incubated with 600 μl of pooled mouse or human plasma diluted in 6 ml of PBS. After extensive washing in PBS, 0.05% Tween 20, bound antibody was eluted in 0.1M glycine, pH 2.5 and immediately neutralized with 1M Tris HCl, pH8. Eluted antibodies were buffer exchanged into PBS by diafiltration in spin columns (Centricon) and sterilized prior to use in immunoblot and in vitro growth assays.

Western Blot

Parasite pellets were prepared by treatment of parasitized RBCs with 0.15% saponin in phosphate buffered saline (PBS), pH 7.4 on ice for 10 min followed by centrifugation (3,000×g, 5 min), and resuspension in cold PBS, and centrifugation (3,000×g, 5 min). Parasite pellets or rPfGARP-A were dissolved in SDS sample loading buffer (Bio-Rad), heated to 95 deg C. for 10 min, and proteins were separated in 4-11% gradient SDS-PAGE gels. Separated proteins were transferred to nitrocellulose membranes which were blocked in 5% milk PBS (pH 7.4) and 0.05% Tween 20 for 1 h. Membranes were probed with polyclonal anti-PfGARP or pre-immune mouse sera, detected by use of anti-mouse IgG antibody conjugated to fluorescent tagged secondary antibodies and imaged on a LI-COR (Odyssey Imaging Systems).

Growth Inhibition Assays

Growth inhibition assays (GIA) were carried out with anti-PfGARP polyclonal serum or IgG monoclonal and polyclonal antibodies, control anti-fluorescein monoclonal antibodies, control mouse serum or IgG as described with minor modifications (Bejon, P. et al. *The Journal of infectious diseases* 204, 9-18, (2011), Malkin, E. M. et al. *Infection and immunity* 73, 3677-3685, 2005), and Long, C. Growth Inhibition Assay Proceedure. http://www.niaid.nih.gov/labsandresources/labs/aboutlabs/lmvr/malariaimmunologysection/Pages/long.aspx#niaid_inlineNav_Anchor (2013)). Briefly, anti-PfGARP antibodies or control were dialyzed overnight in PBS, pH 7.4, heat inactivated at 56° C. for 30 min and pre-incubated with human RBC for 1 hour before use in GIA assays. GIA assays were carried out using W2, 3D7, D10 or 4 newly adapted isolates of *P. falciparum* collected at the Tanzanian field site. Parasites were synchronized to the ring stage by treatment with 5% sorbitol (Lambros, C. & Vanderberg, J. P. *The Journal of parasitology* 65, 418-420 (1979)) for three successive replication cycles and cultured to the ring stage. Parasites at 0.3-0.4% parasitemia and 2% hematocrit were incubated with anti-sera or IgG, in a final volume of 100 μl in microtiter wells. Cultures were performed in triplicate with five replicates (comprising a total of 15 individual wells) prepared for each treatment condition.

After 48 hr, blood films were prepared from each replicate, stained with Giemsa, a microscopist blinded to the treatment conditions enumerated RBCs infected with ring stage parasites, and the results from the three wells were averaged. The relationship between the treatment group and parasitemia outcome of the five replicates was analyzed by Mann-Whitney U test.

In some GIA assays (FIG. 1H), parasites were plated at 0.08% parasitemia and were incubated with anti-sera, in a final volume of 100 μl in microtiter wells. Cultures were examined by microscopy daily for 7 days. Media (with appropriate anti-sera) was changed daily. Cultures were performed in triplicate with five replicates (comprising a total of 15 individual wells) prepared for each treatment condition.

Monoclonal Antibody Production and Epitope Mapping

BALB/cJ IP mice were immunized three times at two-week intervals with 25 ug of rPfGARP-A emulsified in TiterMax and boosted with 25 ug of rPfGARP-A IV three days prior to fusion of splenocytes with P3X63Ag8.653 myeloma cells (ATCC) according to the published method (Kurtis, J. D. et al. *Infect. Immun.* 67, 3424-3429 (1999)).

Hybridomas were culture and cloned by limited dilutions. Hybridomas producing anti-PfGARP antibodies were screened and used for large-scale production of monoclonal antibodies.

The heavy and light chain variable regions of hybridoma clone 7899 (IgG1 kappa) were sequenced, and recombinant plasmids constructed and used for the production of recombinant mAh in HEK293 cells according to manufacturer's protocols (Absolute Antibody). Recombinant mAh expressing the variable heavy and light chains from clone 7899 on a murine IgG1 framework 217 were purified by Protein A chromatography. Recombinant mAh expressing the variable heavy and light chains from clone 7899 on a murine IgG1 Fab framework (monovalent) were purified by Ni-NTA chromatography.

For epitope mapping, a custom 15-mer peptide microarray was designed and printed. The array contained 264 different peptides which spanned the PfGARP-A sequence (aa 410-673). The peptides overlapped by a single amino acid and were printed in duplicate, framed by HA control peptides. The array was probed with rec mAb7899 (red) and anti-HA (green) and imaged on a LI-COR Odyssey according to the manufacturer's protocol (PepperPrint). A duplicate array was probed with polyclonal, monospecific anti-PfGARP-A mouse antibodies (red).

Epitope Mapping Material and Methods

Micro: N- and C-terminus to avoid truncated peptides. The elongated antigen sequence was translated into overlapping peptides with a length of 15 amino acids and max. peptide-peptide overlap of 14 amino acids. The resulting GARP peptide microarray contained 264 different peptides printed in duplicate (528 peptide spots) and was framed additional HA (YPYDVPDYAG, 76 spots) control peptides.

Sample: GARP mouse monoclonal antibody

Washing Buffer: PBS, pH 7.4 with 0.05% Tween 20 (3×10 sec after each incubation step)

Blocking Buffer: Rockland blocking buffer MB-070 (30 min before the first assay)

Incubation Buffer: Washing buffer with 10% blocking buffer

Assay Conditions: Antibody concentration of 1 µg/ml in incubation buffer; incubation for 16 h at 4° C. and shaking at 140 rpm Secondary Antibody: Goat anti-mouse IgG (H+L) DyLight680 (0.2 µg/ml); 45 min staining in incubation buffer at RT Control Antibody: Mouse monoclonal anti-HA (12CA5) DyLight800 (0.5 µg/ml); 45 min staining in incubation buffer at RT Scanner: LI-COR Odyssey Imaging System; scanning offset 0.65 mm, resolution 21 µm, scanning intensities of 111 (red=700 nm/green=800 nm)

Microarray Data: Microarray Data GARP Mouse Monoclonal Antibody

Microarray Identifier: 002122_04 (five array copies for one-by-one assays)

Array Content: The sequence of glutamic acid-rich protein (GARP) was elongated with neutral GSGSGSG linkers Epitope Mapping. Experimental and Data Analysis Pre-staining of a linear GARP peptide microarray copy was done with secondary goat anti-mouse IgG (H+L) DyLight680 antibody in incubation buffer to investigate background interactions with the antigen-derived peptides that could interfere with the main assay. Subsequent incubation of another GARP peptide microarray copy with GARP mouse monoclonal antibody at a concentration of 1 µg/ml in incubation buffer was followed by staining with the secondary antibody and read-out at scanning intensities of 7/7 (red/green). The additional HA control peptides framing the peptide microarray were subsequently stained with the control antibody as internal quality control to confirm the assay quality and the peptide microarray integrity.

Quantification of spot intensities and peptide annotation were based on the 16-bit gray scale tiff files that exhibit a higher dynamic range than the 24-bit colorized tiff files. Microarray image analysis was done with PepSlide® Analyzer and summarized. A software algorithm breaks down fluorescence intensities of each spot into raw, foreground and background signal, and calculates averaged median foreground intensities and spot-to-spot deviations of spot duplicates (see "Mapping Summary" tab). Based on averaged median foreground intensities, an intensity map is generated and interactions in the peptide map highlighted by an intensity color code with red for high and white for low spot intensities. A maximum spot-to-spot deviation of 40%, was tolerated, otherwise the corresponding intensity value was zeroed. The averaged spot intensities of the assay were plotted with the mouse monoclonal antibody against the antigen sequence from the N-terminus to the C-terminus of glutamic acid-rich protein to visualize overall spot intensities and signal-to-noise ratio ("Intensity Plot"). The intensity plot was correlated with peptide and intensity maps as well as with visual inspection of the microarray scan to identify the epitope of GARP mouse monoclonal antibody.

Epitope Mapping Pre-Staining, Secondary Antibody

After 15 min pre-swelling in washing buffer and 30 min incubation in blocking buffer, a GARP peptide microarray copy was initially incubated with the secondary antibody for 45 min at room temperature to analyze background interactions with the antigen-derived peptides that could interfere with the main assay.

Figure 25A:
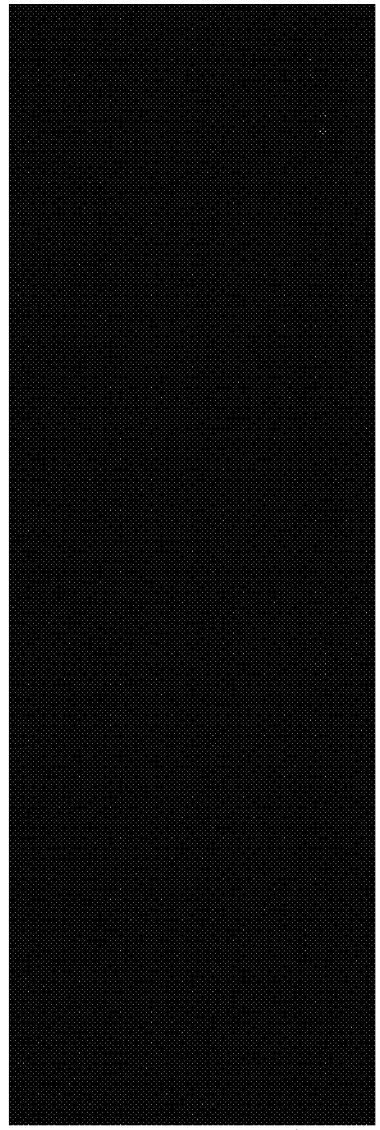
FIGS. 25A-25B are images of epitope mapping of the binding site of PfGARP, with a pre-staining and secondary antibody.
Figure 25B:
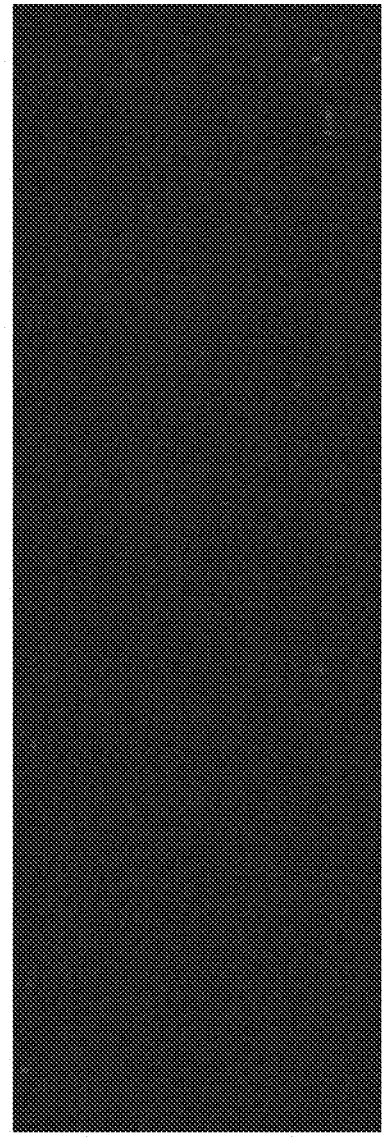

At scanning intensities of 111 (red/green), no background interaction of the secondary antibody was observed with the linear peptides even upon significant increase of brightness and contrast (see FIG. 25B). Data quantification with PepSlide® Analyzer was hence omitted.

Epitope Mapping, GARP Mouse Monoclonal Antibody

Figure 26A:
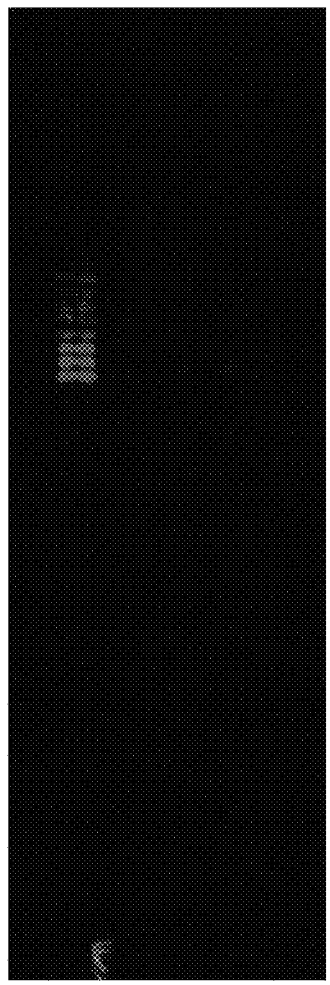
FIGS. 26A-26C are images of epitope mapping of the binding site of PfGARP, GARP mouse monoclonal antibody.
Figure 26B:
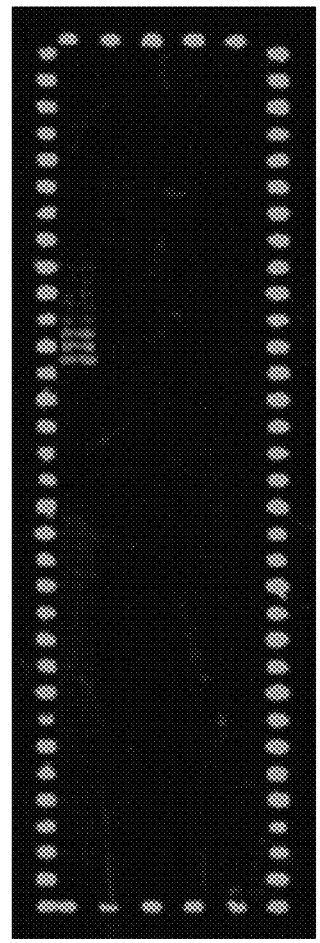
Figure 26C:
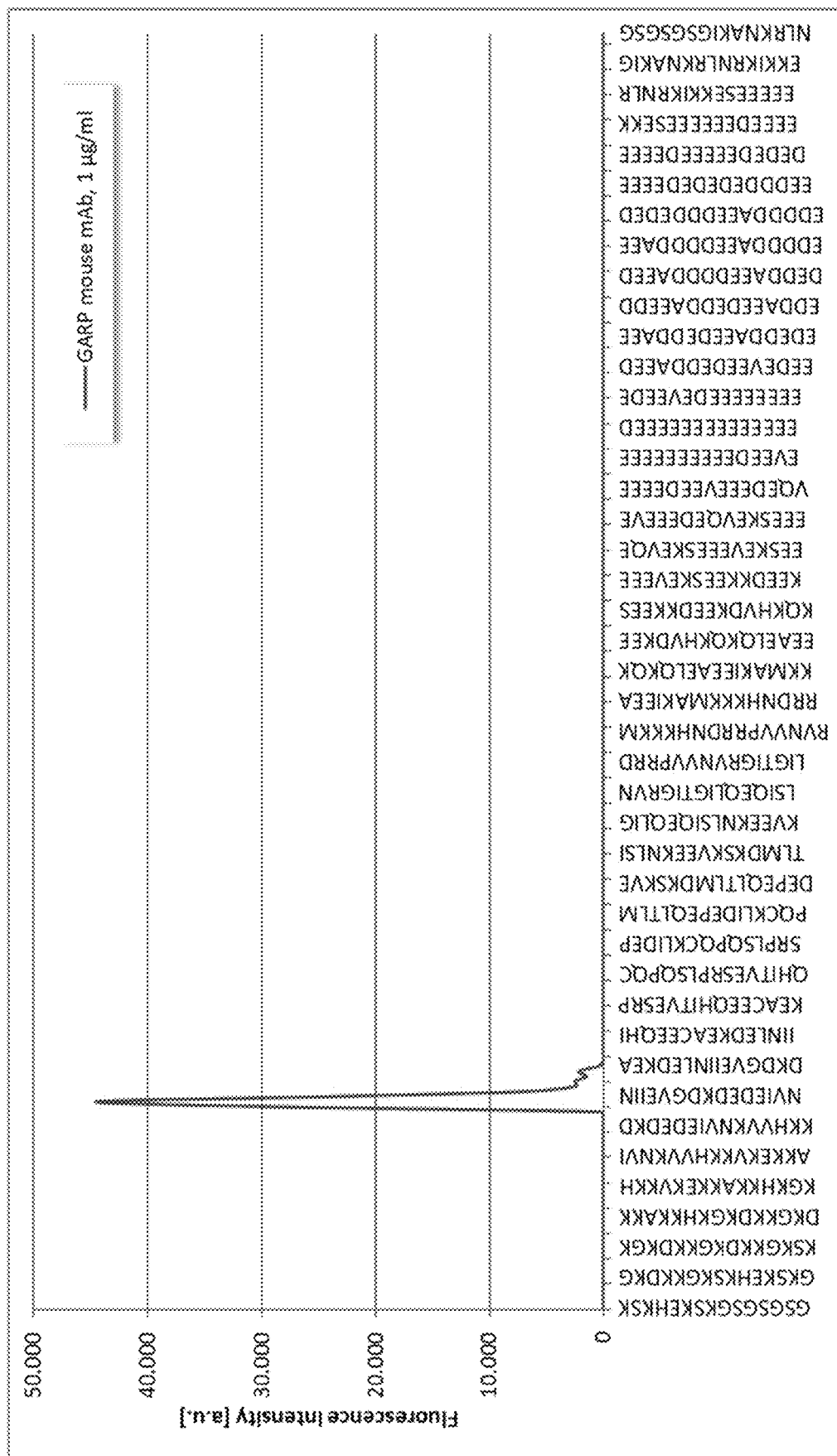

Incubation of a GARP peptide microarray with GARP mouse monoclonal antibody at a concentration of 1 µg/ml was followed by staining with secondary and control antibodies as well as read-out at scanning intensities of 7/7 (red/green). A very strong monoclonal antibody response against a single epitope-like spot pattern formed by adjacent peptides was observed with the consensus motif EDKDGVEI (SEQ ID NO: 1). A high signal-to-noise ratio was observed (FIG. 26C). The well-defined subsequent control staining of HA control peptides is shown in green (FIG. 26B).

The PEPperMAP® Epitope Mapping of GARP mouse monoclonal antibody was performed against glutamic acid-rich protein translated into linear 15 amino acid peptides with a peptide-peptide overlap of 14 amino acids. The resulting GARP peptide microarray was incubated with GARP mouse monoclonal antibody at a concentration of 1 µg/ml in incubation buffer followed by staining with secondary and control antibodies as well as read-out with a LI-COR Odyssey Imaging System. Quantification of spot intensities and peptide annotation were done with PepSlide® Analyzer.

Pre-staining of a linear GARP peptide microarray with the secondary antibody did not show any background interaction with the antigen-derived peptides that could interfere with the main assay. In contrast, a clear and very strong antibody response of GARP mouse monoclonal antibody was observed against adjacent GARP peptides with the consensus motif EDKDGVEI (SEQ ID NO: 1) at high signal-to-noise ratios.

To further investigate the proposed epitope of GARP mouse monoclonal antibody, a PEPperMAP® Epitope Substitution Scan of the underlying wild type peptide NVIEDEDKDGVEIIN (SEQ ID NO: 12) with an exchange of all amino acid positions with the 20 main amino acids. Thus, to identify essential, conserved and variable amino acid positions, analyze the actual epitope length and also assess possible cross-reactions based on the conserved core motif.

Another option for a cross-reactivity analysis of GARP mouse monoclonal antibody is an interaction profiling with the PEPperCHIP® Human Epitome Microarray or the HuProt™ Protein Microarray with ~20,000 human proteins. On request, PEPperPRINT can also validate the proposed epitope by ELISA tests with synthetic peptides or by affinity determination with fluorescence polarization.

Mitochondrial Membrane Potential

Mitochondrial membrane potential was assessed with the dye JC1, a cationic dye that exhibit potential-dependent accumulation in mitochondria. Ring stage infected RBC from *P. falciparum* in vitro cultures were harvested at 5-10% parasitemia and incubated with anti-glycophorin A antibodies (Invitrogen) for 30 minutes at room temperature followed by Hoechst 33342 dye at 1 µg/ml. JC1 staining was performed at a final concentration of 2 µM for 30 minutes at 370 C in the dark with constant agitation and analyzed by flow cytometry.

Caspase Activation Assay

The activation of caspase-like proteases was quantified using a cell permeable, FITC-conjugated pan-caspase inhibitor (FITC-VAD-FMK, ApoStat, R&D Systems) which irreversibly binds and labels activated cysteine proteases. Antibody treated *P. falciparum* infected RBCs (treated with anti-PfGARP or control) were incubated with FITC-VAD-FMK, at a final concentration of 1%, 1 hr before harvest. Samples were washed with PBS to remove unbound reagent, followed by staining with anti-glycophorin A antibodies (Invitrogen) and Hoeehst 33342 (Thermo Scientific) dye as above. Samples were analyzed by flow cytometry.

TUNNEL Assay

Fragmentation of intracellular DNA in the cultured *P. falciparum* parasites was evaluated by TUNEL (terminal deoxynucleotidyl transferase dUTP nick-end labeling) assay, using the APO-DIRECT™ Kit (BD Biosciences). Antibody treated *P. falciparum* infected RBCs (treated with anti-PfGARP or control) were harvested, washed and stored in ice cold 70% ethanol for at least 18 hrs before staining with 50 µl of DNA labeling solution, prepared as per manufacturer's instructions. After about 1 hr incubation with the DNA labeling solution, samples were stained with anti-glycophorin A antibodies (Invitrogen) and Hoeehst 33342 (Thermo Scientific) dye as above and analyzed by flow cytometry.

Lactate Assay

The spent media from 3D7 parasites incubated with recombinant anti-PfGARP monoclonal antibody or control recombinant anti-fluorescein in GIA assays was collected and assayed for lactate levels (Lactate assay kit II, Sigma-Aldrich, MAK065) according to the manufacturer's protocol.

Generation of PfGARPsmV5-Tet Knock Down Parasite Line

Approximately 100 µg of pRR203 was linearized with EcoRV, purified, and co-transfected with 100 ug pRR183 into 3D7 parasites. Parasites were maintained on 500 nM ATc. One day post-transfection, drug pressure was applied with 2.5 nM WR99210 (Jacobus Pharmaceuticals) and the PfDHODH241 inhibitor N-(3-Chloro-4-methylphenyl)-5-methyl-2-(trifluoromethyl)[1,2,4]triazolo[1,5-a]pyrimidin-7-amine (MMV665874 or AD1) at 150 nM. Five days after transfection, AD1 selection was removed.

Transgenic parasites were cloned by limiting dilution and integration of the targeting construct was confirmed by PCR with oligos oJDD1027/oJDD4507 (control), oJDD1027/oJDD2933 (integration), and oJDD4279/4280 (locus size). Tet aptamer size was confirmed by amplifying the aptamer with oligos oJDD3560/oJDD44 and digesting the PCR fragment with PspOMI and KpnI.

Construction of PfGARP Homology-Directed Repair Plasmid

A gene fragment was first synthesized, 3HA-MCS, (gBlock from Integrated DNA Technologies) with three HA epitope tags and a multiple cloning site (MCS), and subcloned it into pSAB01 with NotI and KpnI to generate pVAS70 44. Next, the 10x-Tet Aptamer from pMG62 45 was subcloned into the MCS with ApaI and XmaI (pVAS71). To facilitate future cloning, a second MCS containing AvrII ClaI, BsiWI, and PstI was added using oligos oJDD3541/oJDD3542 to an EcoRI site in the plasmid, generating pRR65.

To add TetR-DOZI to the hDHFR cassette, TetR-DOZI was amplified from pMG62 with oligos oJDD3481/oJDD3253, the Pfhsp86 promoter with oligos oJDD3480/oJDD3482, the coding sequence for hDHFR and the PfhrpII terminator with oligos oJDD3254/oJDD3483. PCR splicing was used by overhang extension (SOE) to generate an hsp86-TetR-DOZI-2A-hDHFR-hrpII cassette where TetR258 DOZI and hDHFR are joined by the 2A ribosomal skip peptide. This cassette was cloned into pRR65 with AflIII and AvrII (pRR67). To add spaghetti monster V5 46 for 3' tagging the coding sequence from pCAG_smFP-V5 (a gift from Loren Looger, Addgene 260 plasmid #59758) was amplified with oligos oJDD3484/oJDD3485 and cloned into pRR67 with NcoI/PspOMI to generate pRR69.

To prevent homology directed repair from occurring between the Cas9-directed cut site and the 3' end of PfGARP, a string (caPfGARP) was generated where the last 438 bp of PfGARP are codon altered. This string was amplified with oligos oJDD4506/oJDD3566, and the 500 bp preceding the codon altered region from 3D7 genomic DNA with oligos oJDD3563/oJDD4507. 500 bp was amplified from the 3' end of PfGARP for the 3' homology region with oligos oJDD3561/oJDD3562 from 3D7 gDNA. PCR SOE was used to create a PfGARP 3'HR-EcoRV-PfGARP 5'HR-caPfGARP fusion. This fusion was cloned into pRR69 with NotI and NcoI to generate pRR203.

Construction of PfGARP-Targeting Cas9 Vector and Generation of Knock Down Parasite Line pUF1-Cas9 47 was used as a starting plasmid to engineer the targeting plasmid. The BbsI type II endonuclease sites were removed from pUF1-Cas9 by amplifying sections of the plasmid with oligos oJDD2959/oJDD2960, oJDD2961/oJDD2962, and oJDD2963/oJDD2964 and Gibson cloning the fragments together to form pBAM200. The *P. falciparum* U6 cassette containing a U6 promoter was then introduced, BbsI sites for guide cloning, the scaffold guide RNA, and U6 terminator. Oligos oJDD3036/oJDD3037 were used to amplify the U6 promoter and oJDD3038/oJDD2789 were used to amplify the guide RNA and U6 terminator. These fragments were fused by PCR SOE and cloned into pBAM200 with EcoRI and AvrII to generate pBAM202.

Next, the rep20 sequence 48 with oligos oJDD3039/oJDD3040 were amplified and cloned into a NotI site in pBAM203. A PfGARP-targeting guide was cloned into the U6 cassette by PCR SOE. The U6 promoter with guide was amplified by oJDD3058/oJDD4088 and gRNA and U6 terminator with guide amplified with oJDD3059/oJDD4089. The cassette was cloned into pBAM203 with EcoRI and AvrII to generate pRR183. The 3D7 parasites were transfected with pRR183 and genome integrated parasites were selected by serial dilution.

Immunofluorescence Assays

Blood smears of asynchronous 3D7 strain parasite cultures were prepared, fixed in cold methanol for 15 minutes, and probed with anti-PfGARP prepared by DNA vaccination, rabbit anti-PfMSP-4 (MR4) or anti-rabbit glycophorin A were diluted 1:200 in PBS, 5% BSA, pH 7.4. Blood smears were incubated with primary antibodies for 1 hr at 25 deg C., washed three times in PBS, 0.05% Tween-20 and incubated with goat anti-mouse IgG conjugated with Alexa fluor 488 (Molecular Probes) and goat anti rabbit IgG conjugated with Alexa Fluor 594 (Molecular Probes). Blood smears were incubated for 10 minutes in 1 µg/ml of 4',6'-diamino-2-phenylindole (DAPI, Sigma) to label nuclei and cover-slipped with ProLong Gold anti-fade reagent (Invitrogen). Blood smears were imaged using a confocal microscope (Leica SP2, Leica Microsystems, Exton, Pa.)

equipped with a 100× oil immersion objective and sequential Z-sections of the infected RBC were collected. Immunofluorescence assays were also performed using Anti-smV5 monoclonal antibodies and control IgG as described above.

To assess co-localization of PfGARP with the food vacuole membrane, parasites were probed with both anti-PfGARP as well as anti-PfCRT, a protein which localizes to the food vacuolar membrane (Pulcini, S. et al. Mutations in the *Plasmodium falciparum* chloroquine resistance transporter, PfCRT, enlarge the parasite's food vacuole and alter drug sensitivities. *Sci Rep* 5, 14552, doi:10.1038/srep14552 (2015)). In some experiments, parasite infected RBCs were incubated with primary antibodies prior to fixation and slide preparation to ensure that the methanol used for fixation did not permeabilize the RBC membrane.

Transmission Electron Microscopy

To assess the impact of anti-PfGARP on parasite ultrastructure, TEM was performed on parasites after 24 hr incubation with anti-PfGARP or control antibodies. 3D7 strain parasites were grown to high parasitemia (10%) consisting of predominantly trophozoites. Parasites were incubated with anti-PfGARP prepared by DNA or rPfGARP-A vaccination at 10% serum concentration for 24 hr at 37° C. Pre-immune mouse sera at 10% serum concentration were used as a negative control.

Parasites were washed three times in 1×PBS, and were fixed for 30 min at 4° C. with 2% glutaraldehyde, 1% paraformaldehyde in 0.1 M sodium cacodylate buffer. Samples were dehydrated, embedded in Epon (EMS), sectioned on an ultra-microtome, counter stained for 10 min in 5% aqueous uranyl acetate and examined on a Philips CM10 electron microscope.

For immunoelectron microscopy, live cell staining was performed followed by fixation. Parasitized RBCs were blocked for 1 hour at 25° C. in 1×PBS containing 2% BSA. Samples were incubated with anti-PfGARP prepared by DNA or rPfGARP-A vaccination (diluted 1:200 in PBS) for 3 hr at 25° C. Pre-immune mouse sera were used as a negative control. The samples were washed three times in 1×PBS and probed with gold conjugated anti-mouse antibodies for 1 hour at 25° C. at 1:2 dilution (Invitrogen). Samples were washed three times in 1×PBS, fixed and processed as described above.

Assessment of Food Vacuole Integrity

The impact of anti-PfGARP antibodies on food vacuole integrity was further evaluated by confocal microscopy using the calcium binding dye Fluo-4-AM, which specifically labels the food vacuole. Ring stage 3D7 parasites were incubated with culture media (negative control), 1 µM chloroquine (positive control), or anti-PfGARP prepared by rPfGARP-A immunization for 24 hours. Parasites were washed with 1×PBS three times and incubated with Fluo-4-AM (a cell-permeable calcium-sensing dye that fluoresces green when bound with $Ca^{+2}$) at a final concentration of 2 µM and DAPI for 30 minutes, at 37° C. The parasites were washed with 1×PBS and observed under a fluorescent microscope. Under these conditions, Fluo-4-AM localizes to the food vacuole as a punctate structure, while chloroquine disrupts the food vacuole leading to dispersion of the dye into the parasite's cytosol.

Serial Block Face Scanning Electron Microscopy (SBF-SEM)

To further assess the impact of anti-PfGARP on parasite ultrastructure, SBF-SEM was performed on parasite infected RBCs that had been treated with anti-PfGARP antisera or preimmune antisera. Ring stage 3D7 strain parasites were grown to 5% parasitemia and incubated with anti-PfGARP antisera (prepared by DNA vaccination) or preimmune sera (10% final serum concentration) for 30 hr at 37° C. Parasites were washed three times in 1×PBS, and fixed for 1 hour at 4° C. with 2% glutaraldehyde in 0.1 M sodium cacodylate buffer containing 1 mM $CaCl_2$ and 1 mM $MgCl_2$. Samples were washed 5 times with sodium cacodylate buffer. Samples were incubated at 4° C. for 1 hour with 1% osmium tetroxide and 1.5% potassium ferrocyanide in sodium cacodylate buffer followed by 5 washes with deionized water. Samples were incubated in 1% aqueous thiocarbohydrazide for 20 min followed by 5 washes with deionized water. Samples were incubated in 1% aqueous osmium tetroxide for 30 min, followed by overnight incubation at 4° C. in 1% uranyl acetate in 70% ethanol followed by 5 washes with deionized water. Samples were finally incubated in 0.2% aqueous lead citrate for 30 min before being dehydrated, treated with propylene oxide, and embedded in Epon resin (EMS). Once cured, samples were cut and mounted on a 6.6 mm specimen mount with conductive silver epoxy (MG Chemicals). Specimens were coated with gold palladium using an Emitech K550 sputter coater before being sectioned and imaged with a Thermo Apreo Volume Scope SEM under high vacuum. Acquired images were processed and the final three-dimensional reconstruction was performed with Amira 2019.2 software Processing of PfGARP PfGARP encodes a predicted amino terminal signal sequence/transmembrane region (aa 1-22) and an 334 appropriately located PEXEL element (aa 48-52). To determine whether parasites process and cleave the PEXEL element, Western blots were probed of parasite extracts and recombinant PfGARP-A using peptide specific antisera generated against peptides that flank the PEXEL element (aa 31-48 and aa 504-522).

Trophozoite Arrest Assays

Trophozoite arrest assay (TAA) were carried out with anti-PfGARP mouse sera or controls. Sera were dialyzed overnight in PBS, pH7.4, heat inactivated at 56° C. for 30 min and pre-incubated with human RBC for 1 hour before use in TAA assays. TAA assays were carried out using 3D7, Dd2, D10 lab strains or 4 newly adapted isolates of *P. falciparum* collected at the Tanzanian field site. Parasites were synchronized to the ring stage by treatment with 5% sorbitol (Lambros, C. & Vanderberg, J. P. *The Journal of parasitology* 65, 418-420 (1979)) for three successive replication cycles. Parasites at 5% parasitemia and 2% hematocrit, consisting mainly of early rings were incubated with anti-sera at a final concentration of 10% or mAbs at 0-1000 µg/ml in a final volume of 100 µl in microtiter wells. Cultures were performed in triplicate with five replicates (comprising a total of 15 individual wells) prepared for each treatment condition. After 36 hr, blood films were prepared from each replicate, stained with Giemsa, a microscopist blinded to the treatment conditions enumerated trophozoite stage parasites, calculated the percentage of trophozoites that were arrested, and the results from the three wells were averaged. Note, the parasites in the anti-PfGARP treated wells displayed a markedly dysmorphic, pyknotic appearance. The relationship between the treatment group and parasitemia outcome of the five replicates was analyzed by Mann-Whitney U test.

Anti-PfGARP Antibody Assays

Initial, confirmatory antibody assays were performed with rPfGARP coated ELISA plates according to published methods. To measure IgG anti-rPfGARP antibody levels in the Kenyan cohort; a bead-based assay was developed according to published methods (Cham, G. K. et al. *Malar J* 7, 108, (2008)). Briefly, 100 µg of rPfGARP-A or 100 µg of BSA was conjugated to 1.25×107 microspheres (Luminex), and conjugated rPfGARP and BSA beads were pooled and lyophilized in single-use aliquots. Reconstituted beads were incubated for 30 min at 37 deg C. with human plasma samples at 1:80 dilution in Assay Buffer E (ABE, PBS pH 7.4 containing 0.1% BSA, 0.05% Tween-20, and 0.05% sodium azide) in microtiter filter bottom plates (Millipore). Beads were washed three times in ABE by vacuum filtration and incubated for 30 min at 37 deg C. with biotinylated anti-human IgG (Pharmingen) diluted 1:1000 in ABE. Beads were washed three times in ABE by vacuum filtration and incubated for 10 min at 37 deg C. with phycoerythrin-conjugated streptavidin (Pharmingen) diluted 1:500 in ABE. Beads were washed three times in ABE by vacuum filtration, resuspended in ABE and analyzed on a BioPlex 200 multi-analyte analyzer. Fluorescence values for BSA beads were subtracted from rPfGARP beads. The cut-off for detectable anti-PfGARP antibody levels was defined as fluorescence values greater than the mean+2SD fluorescence level of 22 healthy North American adults.

To measure IgG anti-rPfGARP antibody levels in the Tanzanian cohort, bead-based assays were performed using aa 23-673 of PfGARP expressed and purified from COS-7 cells as the target antigen. Amino acids 23-673 of PfGARP (excluding initial signal sequence/transmembrane domain) were expressed and purified in a eukaryotic expression system (COS-7 cells) according to published methods (Oleinikov, A. V. et al. *PLoS Pathog* 5, e1000386. Epub 129 Apr. 1000317. (2009), Oleinikov, A. V. et al. *J Infect Dis* 196, 155-164. Epub 2007 May 2023. (2007), and Oleinikov, A. V. et al. *PLoS ONE* 7, e31011, (2012)). Briefly, the coding sequence for aa 23-673 of PfGARP was PCR amplified with primers which encoded BamH1 and EcoR1 restriction sites, gel purified, digested with BamH1 and EcoR1 and ligated into BamH1 and EcoR1 digested vector pAdEx 51-53. Integrity of the PfGARP construct was verified by sequencing on both strands. Transfection of COS-7 cells, expression, extraction, and immobilization of recombinant PfGARP protein and control AdEx protein on the surface of BioPlex beads have been described in detail in previous publications (Oleinikov, A. V. et al. *PLoS Pathog* 5, e1000386. Epub 1002009 April 1000317. (2009), Oleinikov, A. V. et al. *J Infect Dis* 196, 155-164. Epub 2007 May 2023. (2007), and Oleinikov, A. V. et al. *PLoS ONE*1, e31011(2012)).

Immobilization of recombinant PfGARP on beads was verified by reactivity with mouse anti-PfGARP antibodies. PfGARP and AdEx only beads were incubated for 30 min at 37 deg C. with human plasma samples at 1:80 dilution in Assay Buffer E (ABE, PBS pH 7.4 containing 0.1% BSA, 0.05% Tween-20, and 0.05% sodium azide) in microtiter filter bottom plates (Millipore). Beads were washed three times in ABE by vacuum filtration and incubated for 30 min at 37 deg C. with biotinylated anti-human IgG (Pharmingen) diluted 1:1000 in ABE. Beads were washed three times in ABE by vacuum filtration and incubated for 10 min at 37 deg C. with phycoerythrin-conjugated streptavidin (Pharmingen) diluted 1:500 in ABE. Beads were washed three times in ABE by vacuum filtration, resuspended in ABE and analyzed on a BioPlex 200 multi-analyte analyzer. Fluorescence values for AdEx beads were subtracted from rPfGARP beads. The cut-off for detectable anti-PfGARP9 antibody levels was defined as fluorescence values for rPfGARP beads exceeding the value for AdEx beads.

Role of Anti-PfGARP Antibodies in Resistance to Malaria—Statistical Analyses
Tanzanian Birth Cohort
To assess the relationship between anti-PfGARP antibody responses and resistance 394 to clinical malaria outcomes, GEE was developed based repeated measures models with antibody levels as a continuous variable (SAS version 9.3, Cary, N.C.). These models were used to evaluate the relationship between anti-PfGARP antibody levels (log transformed) and risk of malaria outcomes.

Potential confounders and effect modifiers, including hemoglobin phenotype, birthweight, and transmission season at birth, were evaluated and retained in the model if their P value was less than 0.1 or their inclusion altered the beta coefficient for the anti-PfGARP term by more than 10%. Only hemoglobin phenotype met the pre-specified criteria for inclusion (P<0.1). Both the unadjusted results as well as the model adjusted for hemoglobin phenotype are reported.
Kenyan Cohort
To assess the relationship between anti-PfGARP antibody responses and resistance to *P. falciparum* parasitemia, GEE was developed based repeated measures models using JMP version 10 (Cary, N.C.). The relationship between detectable anti-PfGARP IgG antibodies and parasite density was measured on 18 post-treatment blood films. Several potential confounders and effect modifiers were assessed, including age, week of follow-up, exposure to *Anopheles* mosquitoes, and hemoglobin phenotype. Variables, including the week of monitoring, were retained in the model if their P value was less than 0.1 or they changed the parameter estimate for the antibody of interest by >10%. Age, exposure and hemoglobin phenotype were retained for face validity, though they did not meet the pre-specified criteria for inclusion, and PfGARP antibodies remained a significant predictor of parasite density with their exclusion.
PfGARP-A mRNA Production
mRNAs were produced as previously described 54 using T7 RNA polymerase (Megascript, Ambion) on a linearized plasmid encoding codon-optimized (Thess, A. et al. *Mol Ther* 23, 1456-1464 (2015)) PfGARP-A. mRNAs were transcribed to contain 101 nucleotide-long poly(A) tails. One-methylpseudouridine (m1Ψ-5'-triphosphate (TriLink) instead of UTP was used to generate modified nucleoside-containing mRNA. RNAs were capped using the m7G capping kit with 2'-O-methyl transferase (ScriptCap, CellScript) to obtain cap1. mRNA was purified by Fast Protein Liquid Chromatography (FPLC) (Akta Purifier, GE Healthcare), as described (Weissman, D., et al. *Methods in molecular biology* 969, 43-54(2013)). All mRNAs were analyzed by denaturing or native agarose gel electrophoresis and were stored frozen at −20° C.
LNP Formulation of the mRNA
Poly(C) RNA (Sigma) and FPLC-purified m1Ψ-containing mRNAs were encapsulated in LNPs using a self-assembly process in which an aqueous solution of mRNA at pH=4.0 is rapidly mixed with a solution of lipids dissolved in ethanol (Maier, M. A. et al. Biodegradable lipids enabling rapidly eliminated lipid nanoparticles for systemic delivery of RNAi therapeutics. *Molecular therapy: the journal of the American Society of Gene Therapy* 21, 1570-1578, doi: 10.1038/mt.2013.124 (2013)), LNPs used in this study were similar in composition to those described previously (Jayaraman, M. et al. *Angewandte Chemie* 51, 8529-8533, (2012)), which contain an ionizable cationic lipid (proprietary to Acuitas)/phosphatidylcholine/cholesterol/PEG-lipid (50:10:38.5:1.5 mol/mol) and were encapsulated at an RNA to total lipid ratio of ~0.05 (wt/wt). They had a diameter of ~80 nm as measured by dynamic light scattering using a Zetasizer Nano ZS (Malvern Instruments Ltd, Malvern, UK) instrument. mRNA LNP formulations were stored at −80° C. at a concentration of mRNA of ~1 µg/µl.

LNP-mRNA Based Aotus Monkey Vaccination Studies

Monkeys were immunized (n=5 monkeys) intradermally with 50 µg of PfGARP-A as mRNA-LNP or 50 µg Poly(C) (n=5) intradermally on four sites of the shaved back. Monkeys received 3 doses at weeks 0, 3, and 6. Prior to each immunization, sera were obtained for antibody assays. At week 9, animals were challenged with $10^4$ P. falciparum FVO strain (a heterologous challenge as the sequence for rPfGARP was derived from the 3D7 strain) blood-stage parasites by IV injection followed by daily blood films. Antibody assays were performed with PfGARP-A coated beads according to published methods (Cham, G. K. et al. Malar J7, 108 (2008)) using biotin-conjugated anti-monkey IgG antibody (Invitrogen) for detection of bound anti-PfGARP. Monkeys were monitored daily from day 4 post-challenge with blood samples to quantify parasitemia and hemoglobin concentration. Monkeys with parasitemia greater than 7.5%, hematocrit <25%, or exhibiting signs of illness (fever, immobility, decreased food intake, etc.) were treated with oral Mefloquine in accordance with the animal protocol.

Recombinant PfGARP-A Based Aotus Monkey Vaccination Studies

Monkeys were immunized (n=5 monkeys) intradermally with 50 µg of recombinant, E. coli produced PfGARP-A (aa 410-673) emulsified in Ribi adjuvant or Ribi adjuvant alone as controls (n=5). Monkeys received 3 doses at weeks 0, 3, and 6. Prior to each immunization, sera were obtained for antibody assays. At week 9, animals were challenged with $10^4$ P. falciparum FVO strain (a heterologous challenge as the sequence for rPfGARP was derived from the 3D7 strain) blood-stage parasites by IV injection followed by daily blood films. Antibody assays were performed with PfGARP-A coated beads according to published methods (Cham, G. K. et al. Malar J 7, 108 (2008)) using biotin-conjugated anti-monkey IgG antibody (Invitrogen) for detection of bound anti-PfGARP. Monkeys were monitored daily from day 4 post-challenge with blood samples to quantify parasitemia and hemoglobin concentration. Monkeys with parasitemia greater than 7.5%, hematocrit <25%, or exhibiting signs of illness (fever, immobility, decreased food intake, etc.) were treated with oral Mefloquine in accordance with the animal protocol.

General Definitions

The following definitions are included for the purpose of understanding the present subject matter and for constructing the appended patent claims. The abbreviations used herein have their conventional meanings within the chemical and biological arts.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

"Patient" or "subject in need thereof" refers to a living member of the animal kingdom suffering from or who may suffer from the indicated disorder. In embodiments, the subject is a member of a species comprising individuals who may naturally suffer from the disease. In embodiments, the subject is a mammal. Non-limiting examples of mammals include rodents (e.g., mice and rats), primates (e.g., lemurs, bushbabies, monkeys, apes, and humans), rabbits, dogs (e.g., companion dogs, service dogs, or work dogs such as police dogs, military dogs, race dogs, or show dogs), horses (such as race horses and work horses), cats (e.g., domesticated cats), livestock (such as pigs, bovines, donkeys, mules, bison, goats, camels, and sheep), and deer. In embodiments, the subject is a human.

The terms "subject," "patient," "individual," etc. are not intended to be limiting and can be generally interchanged. That is, an individual described as a "patient" does not necessarily have a given disease, but may be merely seeking medical advice.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

In the descriptions herein and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

It is understood that where a parameter range is provided, all integers within that range, and tenths thereof, are also provided by the invention. For example, "0.2-5 mg" is a disclosure of 0.2 mg, 0.3 mg, 0.4 mg, 0.5 mg, 0.6 mg etc. up to and including 5.0 mg.

As used in the description herein and throughout the claims that follow, the meaning of "a," "an," and "the" includes plural reference unless the context clearly dictates otherwise.

As used herein, "treating" or "treatment" of a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean inhibiting the progression of the condition, disorder or disease, slowing the progression of the condition, disorder or disease temporarily, although in some instances, it involves halting the progression of the condition, disorder or disease permanently.

As used herein, the terms "treat" and "prevent" are not intended to be absolute terms. In various embodiments, treatment can refer to a 10%, 20%, 30%, 40%, 50%, 60%, 70%, 80%, 90%, or 100% reduction in the severity of an established disease, condition, or symptom of the disease or condition. In embodiments, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. In embodiments, references to decreasing, reducing, or inhibiting include a change of 10%, 20%, 30%, 40%, 50%, 60%, 70%, 80%, 90% or greater as compared to a control level and such terms can include but do not necessarily include complete elimination. In embodiments, the severity of disease is reduced by at least 10%, as compared, e.g., to the individual before administration or to a control individual not undergoing treatment. In some aspects the severity of disease is reduced by at least 25%, 50%, 75%, 80%, or 90%, or in some cases, no longer detectable using standard diagnostic techniques.

The terms "effective amount," "effective dose," etc. refer to the amount of an agent that is sufficient to achieve a desired effect, as described herein. In embodiments, the term "effective" when referring to an amount of cells or a therapeutic compound may refer to a quantity of the cells or the compound that is sufficient to yield an improvement or a desired therapeutic response without undue adverse side effects (such as toxicity, irritation, or allergic response) commensurate with a reasonable benefit/risk ratio when used in the manner of this disclosure. In embodiments, the term "effective" when referring to the generation of a desired cell population may refer to an amount of one or more compounds that is sufficient to result in or promote the production of members of the desired cell population, especially compared to culture conditions that lack the one or more compounds.

As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Such purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (ribonucleic acid (RNA) or deoxyribonucleic acid (DNA)) or polypeptide is free of the amino acid sequences or nucleic acid sequences that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated.

A "control" sample or value refers to a sample that serves as a reference, usually a known reference, for comparison to a test sample. For example, a test sample can be taken from a test subject, e.g., a subject with malaria, and compared to samples from known conditions, e.g., a subject (or subjects) that does not have malaria (a negative or normal control), or a subject (or subjects) who does have malaria (positive control). A control can also represent an average value gathered from a number of tests or results. One of skill in the art will recognize that controls can be designed for assessment of any number of parameters. One of skill in the art will understand which controls are valuable in a given situation and be able to analyze data based on comparisons to control values. Controls are also valuable for determining the significance of data. For example, if values for a given parameter are variable in controls, variation in test samples will not be considered as significant.

The term, "normal amount" with respect to a compound (e.g., a protein or mRNA) refers to a normal amount of the compound in an individual who does not have malaria in a healthy or general population. The amount of a compound can be measured in a test sample and compared to the "normal control" level, utilizing techniques such as reference limits, discrimination limits, or risk defining thresholds to define cutoff points and abnormal values (e.g., for malaria or a symptom thereof). The normal control level means the level of one or more compounds or combined compounds typically found in a subject known not suffering from malaria. Such normal control levels and cutoff points may vary based on whether a compounds is used alone or in a formula combining with other compounds into an index. Alternatively, the normal control level can be a database of compounds patterns from previously tested subjects who did not develop malaria or a particular symptom thereof (e.g., in the event the malaria develops or a subject already having malaria is tested) over a clinically relevant time horizon.

The level that is determined may be the same as a control level or a cut off level or a threshold level, or may be increased or decreased relative to a control level or a cut off level or a threshold level. In some aspects, the control subject is a matched control of the same species, gender, ethnicity, age group, smoking status, body mass index (BMI), current therapeutic regimen status, medical history, or a combination thereof, but differs from the subject being diagnosed in that the control does not suffer from the disease (or a symptom thereof) in question or is not at risk for the disease.

Relative to a control level, the level that is determined may an increased level. As used herein, the term "increased" with respect to level (e.g., protein or mRNA level) refers to any % increase above a control level. In various embodiments, the increased level may be at least or about a 5% increase, at least or about a 10% increase, at least or about a 15% increase, at least or about a 20% increase, at least or about a 25% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, at least or about a 95% increase, relative to a control level.

Relative to a control level, the level that is determined may a decreased level. As used herein, the term "decreased" with respect to level (e.g., protein or mRNA level) refers to any % decrease below a control level. In various embodiments, the decreased level may be at least or about a 5% decrease, at least or about a 10% decrease, at least or about a 15% decrease, at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, at least or about a 95% decrease, relative to a control level.

The terms "polypeptide," "peptide" and "protein" are used interchangeably herein to refer to a polymer of amino acid residues, wherein the polymer may in embodiments be conjugated to a moiety that does not consist of amino acids. The terms also apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed or chemically synthesized as a single moiety.

"Polypeptide fragment" refers to a polypeptide that has an amino-terminal and/or carboxy-terminal deletion, in which the remaining amino acid sequence is usually identical to the corresponding positions in the naturally-occurring sequence. Fragments typically are at least 5, 6, 8 or 10 amino acids long, at least 14 amino acids long, at least 20 amino acids long, at least 50 amino acids long, or at least 70 amino acids long.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. In embodiments, the percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "identical" or percent "identity," in the context of two or more nucleic acids or polypeptide sequences, refer to two or more sequences or subsequences that are the same or have a specified percentage of amino acid residues or nucleotides that are the same (e.g., 50%, 55%, 60%, 65%, 70%, 75%, 80%, 85%, 90%, 91%, 92%, 93%, 94%, 95%, 96%, 97%, 98%, 99%, or more identity over a specified region, e.g., of an entire polypeptide sequence or an individual domain thereof), when compared and aligned for maximum correspondence over a comparison window, or designated region as measured using a sequence comparison algorithm or by manual alignment and visual inspection. In embodiments, two sequences are 100% identical. In embodiments, two sequences are 100% identical over the entire length of one of the sequences (e.g., the shorter of the two sequences where the sequences have different lengths). In embodiments, identity may refer to the complement of a test sequence. In embodiments, the identity exists over a region that is at least about 10 to about 100, about 20 to about 75, about 30 to about 50 amino acids or nucleotides in length. In embodiments, the identity exists over a region that is at least about 50 amino acids or nucleotides in length, or more preferably over a region that is 100 to 500, 100 to 200, 150 to 200, 175 to 200, 175 to 225, 175 to 250, 200 to 225, 200 to 250 or more amino acids or nucleotides in length.

For sequence comparison, typically one sequence acts as a reference sequence, to which test sequences are compared. In embodiments, when using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window" refers to a segment of any one of the number of contiguous positions (e.g., least about 10 to about 100, about 20 to about 75, about 30 to about 50, 100 to 500, 100 to 200, 150 to 200, 175 to 200, 175 to 225, 175 to 250, 200 to 225, 200 to 250) in which a sequence may be compared to a reference sequence of the same number of contiguous positions after the two sequences are optimally aligned. In embodiments, a comparison window is the entire length of one or both of two aligned sequences. In embodiments, two sequences being compared comprise different lengths, and the comparison window is the entire length of the longer or the shorter of the two sequences. In embodiments relating to two sequences of different lengths, the comparison window includes the entire length of the shorter of the two sequences. In embodiments relating to two sequences of different lengths, the comparison window includes the entire length of the longer of the two sequences.

Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad.

Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Non-limiting examples of algorithms that are suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 may be used, with the parameters described herein, to determine percent sequence identity for nucleic acids and proteins. Software for performing BLAST analyses is publicly available through the National Center for Biotechnology Information (NCBI), as is known in the art. An exemplary BLAST algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. In embodiments, the NCBI BLASTN or BLASTP program is used to align sequences. In embodiments, the BLASTN or BLASTP program uses the defaults used by the NCBI. In embodiments, the BLASTN program (for nucleotide sequences) uses as defaults: a word size (W) of 28; an expectation threshold (E) of 10; max matches in a query range set to 0; match/mismatch scores of 1,-2; linear gap costs; the filter for low complexity regions used; and mask for lookup table only used. In embodiments, the BLASTP program (for amino acid sequences) uses as defaults: a word size (W) of 3; an expectation threshold (E) of 10; max matches in a query range set to 0; the BLOSUM62 matrix (see Henikoff & Henikoff, Proc. Natl. Acad. Sci. USA 89:10915 (1992)); gap costs of existence: 11 and extension: 1; and conditional compositional score matrix adjustment.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

"Nucleic acid" refers to nucleotides (e.g., deoxyribonucleotides, ribonucleotides, and 2'-modified nucleotides) and polymers thereof in either single-, double- or multiple-stranded form, or complements thereof. The terms "polynucleotide," "oligonucleotide," "oligo" or the like refer, in the usual and customary sense, to a linear sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides contemplated herein include any types of RNA, e.g. mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness.

Nucleic acids, including e.g., nucleic acids with a phosphorothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent, or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235, 033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences As may be used herein, the terms "nucleic acid," "nucleic acid molecule," "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides and/or ribonucleotides, and/or analogs, derivatives or modifications thereof. Different polynucleotides may have different three-dimensional structures, and may perform various functions, known or unknown. Non-limiting examples of polynucleotides include genomic DNA, a genome, mitochondrial DNA, a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

The term "amino acid residue," as used herein, encompasses both naturally-occurring amino acids and non-naturally-occurring amino acids. Examples of non-naturally occurring amino acids include, but are not limited to, D-amino acids (i.e. an amino acid of an opposite chirality to the naturally-occurring form), N-α-methyl amino acids, C-α-methyl amino acids, β-methyl amino acids and D- or L-β-amino acids. Other non-naturally occurring amino acids include, for example, β-alanine (β-Ala), norleucine (Nle), norvaline (Nva), homoarginine (Har), 4-aminobutyric acid (γ-Abu), 2-aminoisobutyric acid (Aib), 6-aminohexanoic acid (ε-Ahx), ornithine (orn), sarcosine, α-amino isobutyric acid, 3-aminopropionic acid, 2,3-diaminopropionic acid (2,3-diaP), D- or L-phenylglycine, D-(trifluoromethyl)-phenylalanine, and D-p-fluorophenylalanine.

As used herein, "peptide bond" can be a naturally-occurring peptide bond or a non-naturally occurring (i.e. modified) peptide bond. Examples of suitable modified peptide bonds are well known in the art and include, but are not limited to, —$CH_2NH$—, —$CH_2S$—, —$CH_2CH_2$—, —$CH=CH$— (as or tram), —$COCH_2$—, —$CH(OH)CH_2$—, —$CH_2SO$—, —$CS$—$NH$— and —$NH$—$CO$— (i.e. a reversed peptide bond) (see, for example, Spatola, Vega Data Vol. 1, Issue 3, (1983); Spatola, in *Chemistry and Biochemistry of Amino Acids Peptides and Proteins*, Weinstein, ed., Marcel Dekker, New York, p. 267 (1983); Morley, J. S., *Trends Pharm. Sci.* pp. 463-468 (1980); Hudson et al, *Int. J. Pept. Prot. Res.* 14:177-185 (1979); Spatola et al, *Life Sci.* 38:1243-1249 (1986); Hann, *J. Chem. Soc. Perkin Trans. 1* 307-314 (1982); Almquist et al., *J. Med. Chem.* 23:1392-1398 (1980); Jennings-White et al., *Tetrahedron Lett.* 23:2533 (1982); Szelke et al, EP 45665 (1982); Holladay et al., *Tetrahedron Lett.* 24:4401-4404 (1983); and Hruby, *Life Sci.* 31:189-199 (1982))

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All references, e.g., U.S. patents, U.S. patent application publications, PCT patent applications designating the U.S., published foreign patents and patent applications cited herein are incorporated herein by reference in their entireties. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

While this invention has been particularly shown and described with references to preferred embodiments thereof, it will be understood by those skilled in the art that various changes in form and details may be made therein without departing from the scope of the invention encompassed by the appended claims.

What is claimed:

1. A recombinant, humanized, anti-*Plasmodium falciparum* (*P. falciparum*) PfGARP antibody comprising a heavy chain variable region comprising the amino acid sequences set forth in SEQ ID NO: 13 (complementary determining region (CDR)1), SEQ ID NO: 2 (CDR2), and SEQ ID NO: 3 (CDR3); and a light chain variable region comprising the amino acid sequences set forth in SEQ ID NO: 4 (CDR1), SEQ ID NO: 5 (CDR2), and SEQ ID NO: 6 (CDR3).

2. The anti-*P. falciparum* PfGARP antibody of claim 1, wherein said heavy chain variable region comprises the amino acid sequence set forth in SEQ ID NO: 7 and said light chain variable region comprises the amino acid sequence set forth in SEQ ID NO: 8 or wherein said heavy chain variable region comprises an amino acid sequence that is at least 50% identical to the amino acid sequence of SEQ ID NO: 7 and wherein said light chain variable region comprises an amino acid sequence that is at least 50% identical to the amino acid sequence of SEQ ID NO: 8.

3. The anti-*P. falciparum* PfGARP antibody of claim 1, wherein the amino acid sequence of said heavy chain variable region is SEQ ID NO: 7 and the amino acid sequence of said light chain variable region is SEQ ID NO: 8.

4. An anti-malarial composition comprising the anti-*Plasmodium falciparum* PfGARP antibody of claim 1 in a pharmaceutically acceptable carrier.

5. A method of treating, reducing the severity of *P. falciparum* malaria, killing *P. falciparum*, or inhibiting *P. falciparum* growth in a subject comprising administering to said subject an effective amount of said anti-*P. falciparum* PfGARP antibody of claim 1.

6. The method of claim 5, wherein said subject is a mammal.

7. The method of claim 5, wherein said subject is a human.

8. The method of claim 7, wherein said subject is at least about 6-8 weeks of age.

9. The method of claim 7, wherein said subject is an adolescent female or a female of childbearing age.

10. The method of claim 5, further comprising administering said anti-*P. falciparum* PfGARP antibody or to said subject in combination with a secondary therapy or a secondary agent.

11. The method of claim 10, wherein said secondary agent comprises an inhibitor of parasite liver invasion, RTS,S, an inhibitor of parasite red blood cell invasion, or MSP-1.

12. The anti-*P. falciparum* PfGARP antibody of claim 1, wherein the antibody has a binding specificity to an epitope of PfGARP comprising or consisting of the amino acid sequence, EDKDGVEI (SEQ ID NO: 1).

* * * * *